United States Patent
Das et al.

(10) Patent No.: US 10,189,775 B2
(45) Date of Patent: Jan. 29, 2019

(54) CARBOCYCLIC COMPOUNDS AS ROR GAMMA MODULATORS

(71) Applicant: Glenmark Pharmaceuticals S.A., La Chaux-de-Fonds (CH)

(72) Inventors: Sanjib Das, West Bengal (IN); Laxmikant A. Gharat, Maharashtra (IN); Rajendra L. Harde, Maharashtra (IN); Dnyaneshwar E. Shelke, Maharashtra (IN); Shailesh R. Pardeshi, Maharashtra (IN); Abraham Thomas, Maharashtra (IN); Neelima Khairatkar-Joshi, Maharashtra (IN); Daisy M. Shah, Maharashtra (IN); Malini Bajpai, Uttar Pradesh (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days.

(21) Appl. No.: 15/754,037

(22) PCT Filed: Aug. 26, 2016

(86) PCT No.: PCT/IB2016/055104
§ 371 (c)(1),
(2) Date: Feb. 21, 2018

(87) PCT Pub. No.: WO2017/037595
PCT Pub. Date: Mar. 9, 2017

(65) Prior Publication Data
US 2018/0237382 A1 Aug. 23, 2018

(30) Foreign Application Priority Data

Aug. 28, 2015 (CH) .................. 3299/MUM/2015

(51) Int. Cl.
C07C 237/42 (2006.01)
A61P 11/06 (2006.01)
A61P 11/08 (2006.01)
A61P 11/14 (2006.01)
A61P 17/06 (2006.01)

(52) U.S. Cl.
CPC ............ *C07C 237/42* (2013.01); *A61P 11/06* (2018.01); *A61P 11/08* (2018.01); *A61P 11/14* (2018.01); *A61P 17/06* (2018.01); *C07C 2601/16* (2017.05)

(58) Field of Classification Search
None
See application file for complete search history.

(56) References Cited

FOREIGN PATENT DOCUMENTS

| WO | WO-2012027965 A1 | 3/2012 |
|---|---|---|
| WO | WO-2012028100 A1 | 3/2012 |
| WO | WO-2012064711 A2 | 5/2012 |
| WO | WO-2012100732 A1 | 8/2012 |
| WO | WO-2012100734 A1 | 8/2012 |
| WO | WO-2012139775 A1 | 10/2012 |
| WO | WO-2013171729 A2 | 11/2013 |
| WO | WO-2015008234 A1 | 1/2015 |

OTHER PUBLICATIONS

Aloisi et al., Lymphoid Neogenesis in Chronic Inflammatory Diseases, Nat. Rev. Immunol., 2006, 6:205-217.
Barnes et al., Immunology of Asthma and Chronic Obstructive Pulmonary Disease, Nat. Rev. Immunol., 2008, 8:183-192.
Buonocore, et al., Innate Lymphoid Cells Drive Interluekin-23-Dependent Innate Intestinal Pathology, Letters, 2010, 464:1371-1375.
Eberl, et al., An Essential Function for the Nuclear Receptor ROR?t in the Generation of Fetal Lymphoid Tissue Inducer Cells, Nature Immunology, 2004, 5:1:64-73.
Hueber, et al., Cutting Edge: Mast Cells Express IL-17A in Rheumatoid Arthritis Synovium, The Jouranl of Immunology, 2010, 184:3336-3340.
Ivanov, et al., The Orphan Nuclear Receptor Ror?t Directs The Differentiation Program of Proinflammatory IL-17+ T Helper Cells, Cell, 2006, 126:1121-1133.
Jager, et al., Th1, Th17 and Th9 Effector Cells Induce Experimental Autoimmune Encephalomyelitis with Different Pathological Phenotypes, The Journal of Immunology, 2009, 183:7169-7177.
Jetten et al., Retinoid-related Orphan Receptors (RORs): Critical Roles in Development, Immunity, Circadian Rhythm, and Cellular Metabolism, Nucl. Recept. Signal, 2009, 7:e003.
Jetten, et al., Retinoid-Related Orphan Receptors (RORs): Roles In Cellular diVerentiation and Development, Advances in Developmental Biology, 2006, 16:314-355.
Korn, et al., IL-17 and Th17 Cells, Annu. Rev. Immunol., 2009, 27:485-517.
Leung, et al., The Cytokine Milieu in The Interplay of Pathogenic Th1/Th17 Cells and Regulatory T Cells in Autoimmune Disease, Cellular & Molecular Immunology, 2010, 7:182-189.
Louten, et al., Development and Function of Th17 Cells in Healthy and Disease, J Allergy Clin Immunol, 2009, 123:5:1004-1011.

(Continued)

*Primary Examiner* — Alicia L Otton
(74) *Attorney, Agent, or Firm* — Blank Rome LLP

(57) ABSTRACT

The present disclosure is directed to novel carbocyclic compounds of formula (I) and pharmaceutically acceptable salts thereof, wherein $R^1$, $R^2$, $R^3$, $R^4$, $R^5$, $R^6$, $R^a$, $R^b$, n, m and p are as defined herein, which are active as modulators of retinoid-related orphan receptor gamma t (RORγt). These compounds prevent, inhibit, or suppress the action of RORγt and are therefore useful in the treatment of RORγt mediated diseases, disorders, syndromes or conditions such as, e.g., pain, inflammation, COPD, asthma, rheumatoid arthritis, colitis, multiple sclerosis, psoriasis, neurodegenerative diseases and cancer.

(I)

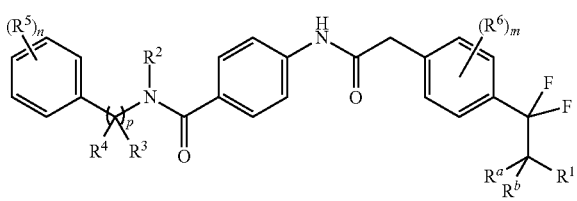

15 Claims, No Drawings

(56) References Cited

OTHER PUBLICATIONS

Magliozzi, et al., Meningeal B-cell Follicles in Secondary Progressive Multiple Sclerosis Associate with Early Onset of Disease and Severe Cortical Pathology, Brain, 2007, 130:1089-1104.
Manel, et al., The Differentiation of Human Th-17 Cells Requires Transforming Growth Factor-ß and Induction of the Nuclear Receptor ROR?t, Nature Immunology, 2008, 9:6:641-649.
Meier, et al., Ectopic Lymphoid-Organ Development Occurs Through Interluekin 7-Mediated Enhanced Survival of Lymphoid-Tissue-Inducer Cells, Immunity, 2007, 26:643-654.
Serafini, et al., Detection of Ectopic B-cell Follicles with Germinal Centers in the Meninges of Patients with Secondary Progressive Multiple Sclerosis, Brain Pathol, 2004, 14:164-174.
Steinman, et al., A Rush to Judgement of Th17, J. Exp. Med., 2008, 205:7:1517-1522.
Sun et al., Requirement for ROR? in Thymocyte Survival and Lymphoid Organ Development, Science, 2000, 288:2369-2372.
Sutton, et al., Interluekin-1 and IL-23 Induce Innate IL-17 Production from γδ T Cells, Amplifying Th17 Responses and Autoimmunity, Immunity, 2009, 31:331-341.
Fresno, et al., Novel Oxasolidinone-Based Peroxisome Proliferator Activated Receptor Agonists: Molecular Modeling, Synthesis, and Biological Evaluation, Journal of Medicinal Chemistry, 2015, 58:16:6639-6652.
International Search Report issued in PCT/IB2016/055104 dated Jan. 3, 2017.

CARBOCYCLIC COMPOUNDS AS ROR GAMMA MODULATORS

RELATED APPLICATIONS

This application is a national stage of International Patent Application No. PCT/IB2016/055104, filed Aug. 26, 2016, which claims the benefit of Indian Provisional Application No. 3299/MUM/2015 filed on Aug. 28, 2015, which is hereby incorporated by reference in its entirety.

TECHNICAL FIELD

The present patent application is directed to novel carbocyclic compounds which may be useful as retinoid-related orphan receptor gamma t (RORγt) modulators.

BACKGROUND OF THE INVENTION

Retinoid-related orphan receptors (RORs) are transcription factors which belong to the steroid hormone nuclear receptor super family. The ROR family consists of three members, ROR alpha (RORα), ROR beta (RORβ) and ROR gamma (RORγ), also known as NR1F1, NR1F2 and NR1F3 respectively (and each encoded by a separate gene RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ, RORγ1 and RORγt (also known as RORγ2) have been identified.

RORγt is a truncated form of RORγ, lacking the first N-terminal 21 amino acids and is exclusively expressed in cells of the lymphoid lineage and embryonic lymphoid tissue inducers (Sun et al., *Science*, 2000, 288, 2369-2372; Eberl et al., *Nat Immunol.*, 2004, 5: 64-73) in contrast to RORγ which is expressed in multiple tissues (heart, brain, kidney, lung, liver and muscle).

RORγt has been identified as a key regulator of Th17 cell differentiation. Th17 cells are a subset of T helper cells which produce IL-17 and other proinflammatory cytokines and have been shown to have key functions in several mouse autoimmune disease models including experimental autoimmune encephalomyelitis (EAE) and collagen-induced arthritis (CIA). In addition, Th17 cells have also been associated in the pathology of a variety of human inflammatory and autoimmune disorders including multiple sclerosis, rheumatoid arthritis, psoriasis, Crohn's disease and asthma (Jetten et al., *Nucl. Recept. Signal*, 2009, 7:e003; Manel et al., *Nat. Immunol.*, 2008, 9, 641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman et al., *J. Exp. Med.*, 2008, 205: 1517-1522; Leung et al., *Cell. Mol. Immunol.*, 2010 7: 182-189). Th17 cells are activated during the disease process and are responsible for recruiting other inflammatory cell types, especially neutrophils, to mediate pathology in the target tissues (Korn et al., *Annu. Rev. Immunol.*, 2009, 27:485-517) and RORγt has been shown to play a critical role in the pathogenic responses of Th17 cells (Ivanov et al., *Cell*, 2006 126: 1121-1133). RORγt deficient mice have shown no Th17 cells and also resulted in amelioration of EAE. The genetic disruption of RORγ in a mouse colitis model also prevented colitis development (Buonocore et al., *Nature*, 2010, 464: 1371-1375). The role of RORγt in the pathogenesis of autoimmune or inflammatory diseases has been well documented in the literature. (Jetten et al., *Adv. Dev. Biol.*, 2006, 16:313-355; Meier et al. *Immunity*, 2007, 26:643-654; Aloisi et al., *Nat. Rev. Immunol.*, 2006, 6:205-217; Jager et al., *J. Immunol.*, 2009, 183:7169-7177; Serafmi et al., *Brain Pathol.*, 2004, 14: 164-174; Magliozzi et al., *Brain*, 2007, 130: 1089-1104; Barnes et al., *Nat. Rev. Immunol.*, 2008, 8: 183-192).

In addition, RORγt is also shown to play a crucial role in other non-Th17 cells, such as mast cells (Hueber et al., *J Immunol.*, 2010, 184: 3336-3340). RORγt expression and secretion of Th17-type of cytokines has also been reported in NK T-cells (Eberl et al., *Nat. Immunol.*, 2004, 5: 64-73) and gamma-delta T-cells (Sutton et al, *Nat. Immunol.*, 2009, 31: 331-341; Louten et al., *J Allergy Clin. Immunol.*, 2009, 123: 1004-1011), suggesting an important function for RORγt in these cells.

PCT Publication Nos. WO 2012/139775, WO 2012/027965, WO 2012/028100, WO 2012/100732, WO 2012/100734, WO2012/064744, WO 2013/171729 and WO 2015/008234 disclose heterocyclic compounds which are modulators of retinoid-related orphan receptor gamma (RORγ) receptor activity.

In view of the above, a need exists for new therapeutic agents that modulate the activity of RORγt and thus will provide new methods for treating diseases or conditions associated with the modulation of RORγt.

The present application is directed to compounds that are modulators of the RORγt receptor.

SUMMARY OF THE INVENTION

In one aspect, the present invention relates to a compound of formula (I)

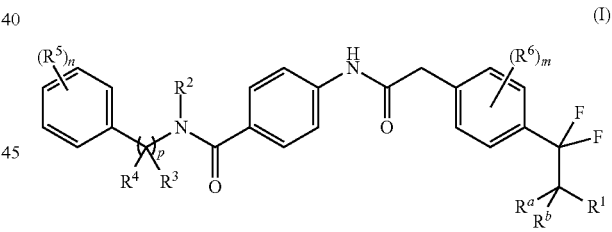

or a tautomer thereof, stereoisomer thereof or pharmaceutically acceptable salt thereof, wherein $R^1$ is selected from amino, hydroxyl, $C_{1-8}$alkyl and $C_{1-8}$alkoxy;

$R^2$ is selected from $C_{1-8}$alkyl, halo$C_{1-8}$alkyl, hydroxy$C_{1-8}$alkyl, $C_{3-6}$cycloalkyl and $C_{3-6}$cycloalkyl$C_{1-8}$alkyl;

$R^3$ is selected from hydrogen, $C_{1-8}$alkyl, halo$C_{1-8}$alkyl and hydroxy$C_{1-8}$alkyl;

$R^4$ is selected from $C_{1-8}$alkyl, $C_{1-8}$alkoxy, halo$C_{1-8}$alkyl, hydroxy$C_{1-8}$alkyl, $C_{3-6}$cycloalkyl and $C_{3-6}$cycloalkyl$C_{1-8}$alkyl;

each occurrence of $R^5$ is independently selected from halogen, hydroxyl, cyano, $C_{1-8}$ alkyl, $C_{1-8}$alkoxy, halo$C_{1-8}$alkyl, halo$C_{1-8}$alkoxy, hydroxy$C_{1-8}$alkyl, $C_{3-6}$cycloalkyl and optionally substituted $C_{6-14}$aryl, wherein the substitution on $C_{6-14}$aryl is halogen;

each occurrence of $R^6$ is independently selected from halogen, cyano, hydroxyl, $C_{1-8}$ alkyl and $C_{3-6}$cycloalkyl;

$R^a$ and $R^b$, which may be same or different, are each independently selected from hydrogen and $C_{1-8}$alkyl; or $R^a$ and $R^b$ together may form an oxo group;

'n' is 1, 2, 3 or 4;
'm' is 0, 1 or 2; and
'p' is 0 or 1.

The compounds of formula (I) may involve one or more embodiments. Embodiments of compounds of formula (I) include compounds of formula (II) as described hereinafter. It is to be understood that the embodiments below are illustrative of the present invention and are not intended to limit the claims to the specific embodiments exemplified. It is also to be understood that the embodiments defined herein may be used independently or in conjunction with any definition and any other embodiment defined herein. Thus the invention contemplates all possible combinations and permutations of the various independently described embodiments. For example, the invention provides compounds of formula (I) as defined above wherein $R^2$ is methyl or 2,2,2-trifluoroethyl (according to an embodiment defined below); $R^3$ is hydrogen (according to another embodiment defined below); and 'm' is 0 (according to yet another embodiment defined below).

According to one embodiment, specifically provided are compounds of formula (I), in which $R^1$ is amino (—NH$_2$), hydroxyl (—OH), $C_{1-8}$alkyl (e.g. methyl) or $C_{1-8}$alkoxy (e.g. methoxy or ethoxy).

According to another embodiment, specifically provided are compounds of formula (I), in which $R^1$ is amino, hydroxyl, methyl, methoxy or ethoxy.

According to yet another embodiment, specifically provided are compounds of formula (I), in which $R^2$ is $C_{1-8}$alkyl (e.g. methyl) or halo$C_{1-8}$alkyl (e.g. 2,2,2-trifluoroethyl).

According to yet another embodiment, specifically provided are compounds of formula (I), in which $R^2$ is methyl or 2,2,2-trifluoroethyl.

According to yet another embodiment, specifically provided are compounds of formula (I), in which $R^3$ is hydrogen.

According to yet another embodiment, specifically provided are compounds of formula (I), in which $R^4$ is $C_{1-8}$alkyl (e.g. methyl) or $C_{3-6}$cycloalkyl (e.g. cyclopropyl).

According to yet another embodiment, specifically provided are compounds of formula (I), in which $R^4$ is methyl or cyclopropyl.

According to yet another embodiment, specifically provided are compounds of formula (I), in which $R^3$ is hydrogen; $R^4$ is methyl or cyclopropyl and 'p' is 1.

According to yet another embodiment, specifically provided are compounds of formula (I), in which each occurrence of $R^5$ is halogen (e.g. fluoro or chloro), $C_{1-8}$alkyl (e.g. methyl), $C_{3-6}$cycloalkyl (e.g. cyclopropyl) or optionally substituted $C_{6-14}$aryl (e.g. 2-fluorophenyl).

According to yet another embodiment, specifically provided are compounds of formula (I), in which each occurrence of $R^5$ is fluoro, chloro, methyl, cyclopropyl or 2-fluorophenyl.

According to yet another embodiment specifically provided are compounds of formula (I), in which $R^a$ and $R^b$ are hydrogen.

According to yet another embodiment, specifically provided are compounds of formula (I), in which one of $R^a$ and $R^b$ is hydrogen and the other is $C_{1-8}$alkyl (e.g. methyl).

According to yet another embodiment specifically provided are compounds of formula (I), in which one of $R^a$ and $R^b$ is hydrogen and the other is methyl.

According to yet another embodiment specifically provided are compounds of formula (I), in which $R^a$ and $R^b$ are $C_{1-8}$alkyl (e.g. methyl).

According to yet another embodiment specifically provided are compounds of formula (I), in which $R^a$ and $R^b$ are methyl.

According to yet another embodiment specifically provided are compounds of formula (I), in which $R^a$ and $R^b$ together forms oxo group.

According to yet another embodiment, specifically provided are compounds of formula (I), in which 'm' is 0.

According to yet another embodiment, specifically provided are compounds of formula (I), in which 'n' is 1, 2 or 3.

According to yet another embodiment, specifically provided are compounds of formula (I), in which 'p' is 0.

According to yet another embodiment, specifically provided are compounds of formula (I), in which 'p' is 1.

According to yet another embodiment, specifically provided are compounds of formula (I), in which

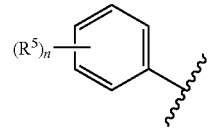

is 2-chlorophenyl, 3-chlorophenyl, 4-chlorophenyl, 2'-fluoro-5-methyl-[1,1'-biphenyl]-3-yl, 2-chloro-4-cyclopropylphenyl, 2-chloro-5-cyclopropylphenyl, 3-chloro-2-fluorophenyl, 3-chloro-5-fluorophenyl, 2-chloro-4-methylphenyl, 2-chloro-5-methylphenyl, 2-chloro-6-methylphenyl, 4-chloro-2-methylphenyl, 2-cyclopropyl-4-methylphenyl, 5-cyclopropyl-2-methylphenyl, 2,4-dichlorophenyl, 2,5-dichlorophenyl, 3,5-dichlorophenyl, 3,5-dimethylphenyl, 2-fluoro-5-methylphenyl, 2-chloro-4,6-dimethylphenyl, 4-chloro-2-fluoro-5-methylphenyl or mesityl.

According to yet another embodiment, specifically provided are compounds of formula (I), in which
$R^1$ is amino, hydroxyl, methyl, methoxy or ethoxy;
$R^2$ is methyl or 2,2,2-trifluoroethyl;
$R^3$ is hydrogen; $R^4$ is methyl or cyclopropyl;
$R^5$ is fluoro, chloro, methyl, cyclopropyl or 2-fluorophenyl;
$R^a$ is hydrogen or methyl;
$R^b$ is hydrogen or methyl; or $R^a$ and $R^b$ together forms oxo group;
'm' is 0;
'n' is 1, 2 or 3; and
'p' is 0 or 1.

According to yet another embodiment, specifically provided are compounds of formula (I), in which
$R^1$ is amino, hydroxyl, methyl, methoxy or ethoxy;
$R^2$ is methyl or 2,2,2-trifluoroethyl;
$R^3$ is hydrogen; $R^4$ is methyl or cyclopropyl;

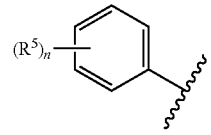

is 2-chlorophenyl, 3-chlorophenyl, 4-chlorophenyl, 2'-fluoro-5-methyl-[1,1'-biphenyl]-3-yl, 2-chloro-4-cyclopropylphenyl, 2-chloro-5-cyclopropylphenyl, 3-chloro-2-fluorophenyl, 3-chloro-5-fluorophenyl, 2-chloro-4-methylphenyl, 2-chloro-5-methylphenyl, 2-chloro-6-methylphenyl, 4-chloro-2-methylphenyl, 2-cyclopropyl-4-methylphenyl, 5-cyclopropyl-2-methylphenyl, 2,4-dichlorophenyl, 2,5-dichlorophenyl, 3,5-dichlorophenyl, 3,5-dimethylphenyl, 2-fluoro-5-methylphenyl, 2-chloro-4,6-dimethylphenyl, 4-chloro-2-fluoro-5-methylphenyl or mesityl;

'm' is 0;
'n' is 1, 2 or 3; and
'p' is 0 or 1.

According to yet another embodiment, the definition of "compounds of formula (I)" inherently includes all stereoisomers of the compound of formula (I) either as pure stereoisomer or as a mixture of two or more stereomers. The word stereoisomers includes enantiomers, diasteroisomers, racemates, cis isomers, trans isomers and mixture thereof.

According to yet another embodiment, the compounds of formula (I) is a compound that may exist in the form of one or more stereoisomers, wherein one or more of those steroisomers is therapeutically active.

According to yet another embodiment, the compounds of formula (I) comprises a therapeutically active stereoisomer that is substantially free of other stereoisomers.

According to yet another embodiment, compounds of formula (I) comprises a therapeutically active stereoisomer that has less than about 50%, less than about 40%, less than about 30%, less than about 20%, less than about 10%, less than about 5%, or less than about 1% by weight of other steroisomers.

According to an embodiment, specifically provided are compounds of formula (I) with an $IC_{50}$ value of less than 500 nM, preferably less than 100 nM, more preferably less than 50 nM, with respect to RORγt activity.

Further embodiments relating to groups $R^1$, $R^2$, $R^4$, $R^5$, $R^a$, $R^b$, m, n, p (and groups defined therein) are described hereinafter in relation to the compounds of formula (II) and formula (III). It is to be understood that these embodiments are not limited to use in conjunction with formula (II) or formula (III), but apply independently and individually to the compounds of formula (I). For example, in an embodiment described hereinafter, the invention specifically provides compounds of formula (II) or formula (III), wherein $R^2$ is methyl or 2,2,2-trifluoroethyl and consequently there is also provided a compound of formula (I) in which $R^2$ is methyl or 2,2,2-trifluoroethyl.

The invention also provides a compound of formula (II), which is an embodiment of a compound of formula (I).

Accordingly the invention provides a compound of formula (II)

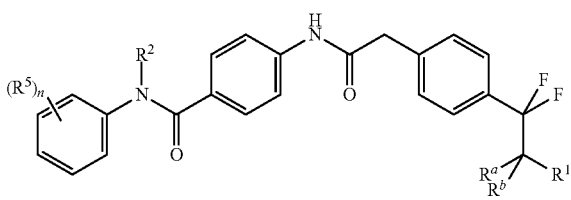

(II)

or a tautomer thereof, stereoisomer thereof or pharmaceutically acceptable salt thereof, wherein $R^1$ is selected from amino, hydroxyl, $C_{1-8}$alkyl and $C_{1-8}$alkoxy;

$R^2$ is selected from $C_{1-8}$alkyl, halo$C_{1-8}$alkyl, hydroxy$C_{1-8}$alkyl, $C_{3-6}$cycloalkyl and $C_{3-6}$cycloalkyl$C_{1-8}$alkyl;

each occurrence of $R^5$ is independently selected from halogen, hydroxyl, cyano, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl and optionally substituted $C_{6-14}$aryl, wherein the substitution on $C_{6-14}$aryl is halogen;

$R^a$ and $R^b$, which may be same or different, are each independently selected from hydrogen and $C_{1-8}$alkyl; or $R^a$ and $R^b$ together may form an oxo group; and 'n' is 1, 2, 3 or 4;

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (II) as defined above wherein, $R^a$ and $R^b$ are hydrogen (according to an embodiment defined below), $R^1$ is amino, hydroxyl, methyl, methoxy or ethoxy (according to another embodiment defined below) and $R^2$ is methyl or 2,2,2-trifluoroethyl (according to yet another embodiment defined below).

According to one embodiment, specifically provided are compounds of formula (II), in which $R^1$ is amino (—NH$_2$), hydroxyl (—OH), $C_{1-8}$alkyl (e.g. methyl) or $C_{1-8}$alkoxy (e.g. methoxy or ethoxy).

According to another embodiment, specifically provided are compounds of formula (II), in which $R^1$ is amino, hydroxyl, methyl, methoxy or ethoxy.

According to yet another embodiment, specifically provided are compounds of formula (II), in which $R^2$ is $C_{1-8}$alkyl (e.g. methyl) or halo$C_{1-8}$alkyl (e.g. 2,2,2-trifluoroethyl).

According to yet another embodiment, specifically provided are compounds of formula (II), in which $R^2$ is methyl or 2,2,2-trifluoroethyl.

According to yet another embodiment, specifically provided are compounds of formula (II), in which each occurrence of $R^5$ is halogen (e.g. fluoro or chloro), $C_{1-8}$alkyl (e.g. methyl), $C_{3-6}$cycloalkyl (e.g. cyclopropyl) or optionally substituted $C_{6-14}$aryl (e.g. 2-fluorophenyl).

According to yet another embodiment, specifically provided are compounds of formula (II), in which each occurrence of $R^5$ is fluoro, chloro, methyl, cyclopropyl or 2-fluorophenyl.

According to yet another embodiment specifically provided are compounds of formula (II), in which $R^a$ and $R^b$ are hydrogen.

According to yet another embodiment, specifically provided are compounds of formula (II), in which one of $R^a$ and $R^b$ is hydrogen and the other is $C_{1-8}$alkyl (e.g. methyl).

According to yet another embodiment specifically provided are compounds of formula (II), in which one of $R^a$ and $R^b$ is hydrogen and the other is methyl.

According to yet another embodiment specifically provided are compounds of formula (II), in which $R^a$ and $R^b$ are $C_{1-8}$alkyl (e.g. methyl).

According to yet another embodiment specifically provided are compounds of formula (II), in which $R^a$ and $R^b$ are methyl.

According to yet another embodiment specifically provided are compounds of formula (II), in which $R^a$ and $R^b$ together forms oxo group.

According to yet another embodiment, specifically provided are compounds of formula (II), in which 'n' is 1, 2 or 3.

According to yet another embodiment, specifically provided are compounds of formula (II), in which

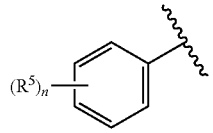

is 2-chlorophenyl, 3-chlorophenyl, 4-chlorophenyl, 2'-fluoro-5-methyl-[1,1'-biphenyl]-3-yl, 2-chloro-4-cyclopropylphenyl, 2-chloro-5-cyclopropylphenyl, 3-chloro-2-fluorophenyl, 3-chloro-5-fluorophenyl, 2-chloro-4-methylphenyl, 2-chloro-5-methylphenyl, 2-chloro-6-methylphenyl, 4-chloro-2-methylphenyl, 2-cyclopropyl-4-methylphenyl, 5-cyclopropyl-2-methylphenyl, 2,4-dichlorophenyl, 2,5-dichlorophenyl, 3,5-dichlorophenyl, 3,5-dimethylphenyl, 2-fluoro-5-methylphenyl, 2-chloro-4,6-dimethylphenyl, 4-chloro-2-fluoro-5-methylphenyl or mesityl.

According to yet another embodiment, specifically provided are compounds of formula (II), in which
$R^1$ is amino, hydroxyl, methyl, methoxy or ethoxy;
$R^2$ is methyl or 2,2,2-trifluoroethyl;
$R^5$ is fluoro, chloro, methyl, cyclopropyl or 2-fluorophenyl;
$R^a$ is hydrogen or methyl;
$R^b$ is hydrogen or methyl; or $R^a$ and $R^b$ together forms oxo group; and
'n' is 1, 2 or 3.

According to yet another embodiment, specifically provided are compounds of formula (II), in which
$R^1$ is amino, hydroxyl, methyl, methoxy or ethoxy;
$R^2$ is methyl or 2,2,2-trifluoroethyl;
$R^a$ is hydrogen or methyl;
$R^b$ is hydrogen or methyl; or $R^a$ and $R^b$ together forms oxo group; and

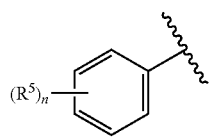

is 2-chlorophenyl, 3-chlorophenyl, 4-chlorophenyl, 2'-fluoro-5-methyl-[1,1'-biphenyl]-3-yl, 2-chloro-4-cyclopropylphenyl, 2-chloro-5-cyclopropylphenyl, 3-chloro-2-fluorophenyl, 3-chloro-5-fluorophenyl, 2-chloro-4-methylphenyl, 2-chloro-5-methylphenyl, 2-chloro-6-methylphenyl, 4-chloro-2-methylphenyl, 2-cyclopropyl-4-methylphenyl, 5-cyclopropyl-2-methylphenyl, 2,4-dichlorophenyl, 2,5-dichlorophenyl, 3,5-dichlorophenyl, 3,5-dimethylphenyl, 2-fluoro-5-methylphenyl, 2-chloro-4,6-dimethylphenyl, 4-chloro-2-fluoro-5-methylphenyl or mesityl.

According to an embodiment, specifically provided are compounds of formula (II) with an $IC_{50}$ value of less than 500 nM, preferably less than 100 nM, more preferably less than 50 nM, with respect to RORγt activity.

The invention also provides a compound of formula (III), which is an embodiment of a compound of formula (I).

Accordingly the invention provides a compound of formula (III)

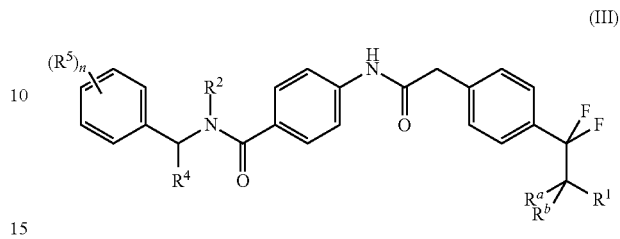

or a tautomer thereof, stereoisomer thereof or pharmaceutically acceptable salt thereof, wherein
$R^1$ is selected from amino, hydroxyl, $C_{1-8}$alkyl and $C_{1-8}$alkoxy;
$R^2$ is selected from $C_{1-8}$alkyl, halo$C_{1-8}$alkyl, hydroxy$C_{1-8}$alkyl, $C_{3-6}$cycloalkyl and $C_{3-6}$cycloalkyl$C_{1-8}$alkyl;
$R^4$ is selected from $C_{1-8}$alkyl, $C_{1-8}$alkoxy, halo$C_{1-8}$alkyl, hydroxy$C_{1-8}$alkyl, $C_{3-6}$cycloalkyl and $C_{3-6}$cycloalkyl$C_{1-8}$ alkyl;
each occurrence of $R^5$ is independently selected from halogen, hydroxyl, cyano, $C_{1-8}$ alkyl, $C_{1-8}$alkoxy, halo$C_{1-8}$alkyl, halo$C_{1-8}$alkoxy, hydroxy$C_{1-8}$alkyl, $C_{3-6}$cycloalkyl and optionally substituted $C_{6-14}$aryl, wherein the substitution on $C_{6-14}$aryl is halogen;
$R^a$ and $R^b$, which may be same or different, are each independently selected from hydrogen and $C_{1-8}$alkyl; or $R^a$ and $R^b$ together may form an oxo group; and
'n' is 1, 2, 3 or 4;

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (III) as defined above wherein $R^1$ is hydroxyl, methyl or methoxy (according to an embodiment defined below), $R^4$ is methyl or cyclopropyl (according to another embodiment defined below) and 'n' is 1 (according to yet another embodiment defined below).

According to one embodiment, specifically provided are compounds of formula (III), in which $R^1$ is hydroxyl (—OH), $C_{1-8}$alkyl (e.g. methyl) or $C_{1-8}$alkoxy (e.g. methoxy).

According to another embodiment, specifically provided are compounds of formula (III), in which $R^1$ is hydroxyl, methyl or methoxy.

According to yet another embodiment, specifically provided are compounds of formula (III), in which $R^2$ is $C_{1-8}$alkyl (e.g. methyl).

According to yet another embodiment, specifically provided are compounds of formula (III), in which $R^2$ is methyl.

According to yet another embodiment, specifically provided are compounds of formula (III), in which $R^4$ is $C_{1-8}$alkyl (e.g. methyl) or $C_{3-6}$cycloalkyl (e.g. cyclopropyl).

According to yet another embodiment, specifically provided are compounds of formula (III), in which $R^4$ is methyl or cyclopropyl.

According to yet another embodiment specifically provided are compounds of formula (III), in which each occurrence of $R^5$ is halogen (e.g. chloro).

According to yet another embodiment, specifically provided are compounds of formula (III), in which each occurrence of $R^5$ is chloro.

According to yet another embodiment, specifically provided are compounds of formula (III), in which each occurrence of $R^5$ is chloro and 'n' is 1.

According to yet another embodiment specifically provided are compounds of formula (III), in which $R^a$ and $R^b$ are hydrogen.

According to yet another embodiment, specifically provided are compounds of formula (III), in which one of $R^a$ and $R^b$ is hydrogen and the other is $C_{1-8}$alkyl (e.g. methyl).

According to yet another embodiment specifically provided are compounds of formula (III), in which one of $R^a$ and $R^b$ is hydrogen and the other is methyl.

According to yet another embodiment, specifically provided are compounds of formula (III), in which 'n' is 1.

According to yet another embodiment, specifically provided are compounds of formula (III), in which

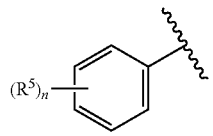

is 4-chlorophenyl.

According to yet another embodiment, specifically provided are compounds of formula (III), in which
$R^1$ is hydroxyl, methyl or methoxy;
$R^2$ is methyl;
$R^4$ is methyl or cyclopropyl;
$R^5$ is chloro;
$R^a$ is hydrogen;
$R^b$ is hydrogen or methyl; and
'n' is 1.

According to yet another embodiment, specifically provided are compounds of formula (III), in which
$R^1$ is hydroxyl, methyl or methoxy;
$R^2$ is methyl;
$R^4$ is methyl or cyclopropyl;
$R^a$ is hydrogen;
$R^b$ is hydrogen or methyl; and

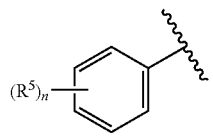

is 4-chlorophenyl.

According to an embodiment, specifically provided are compounds of formula (III) with an $IC_{50}$ value of less than 500 nM, preferably less than 100 nM, more preferably less than 50 nM, with respect to RORγt activity.

Compounds of the present invention include the compounds in Examples 1-40. It should be understood that the formulas (I), (II) and (III) structurally encompasses all geometrical isomers, stereoisomers, enantiomers and diastereomers, N-oxides, and pharmaceutically acceptable salts that may be contemplated from the chemical structure of the genera described herein.

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a tablet, capsule, sachet, paper or other container.

The compounds and pharmaceutical compositions of the present invention are useful for inhibiting the activity of RORγt. Thus, the present invention further provides a method of inhibiting RORγt in a subject in need thereof by administering to the subject one or more compounds described herein in an amount effective to cause inhibition of such receptor.

In a further aspect, the present invention relates to a method of treating a disease, disorder or condition modulated by RORγt, such as an autoimmune disease, inflammatory disease, respiratory disorder, pain and cancer comprising administering to a subject in need thereof a compound according to any of the embodiments described herein.

In another aspect, the present invention relates to a method of treating a disease, disorder or condition modulated by RORγt, such as chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease, comprising administering to a subject in need thereof a compound according to any of the embodiments described herein.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, such as, but not limited to, methyl, ethyl, n-propyl, 1-methylethyl (isopropyl), n-butyl, n-pentyl, and 1,1-dimethylethyl (t-butyl). The term "$C_{1-8}$alkyl" refers to an alkyl chain having 1 to 8 carbon atoms. The term "$C_{1-4}$alkyl" refers to an alkyl chain having 1 to 4 carbon atoms.

Unless set forth or recited to the contrary, all alkyl groups described or claimed herein may be straight chain or branched.

The term "alkoxy" denotes an alkyl group attached via an oxygen linkage to the rest of the molecule (e.g. $C_{1-8}$ alkoxy). Representative examples of such groups are —$OCH_3$ and —$OC_2H_5$. Unless set forth or recited to the contrary, all alkoxy groups described or claimed herein may be straight chain or branched.

The term "haloalkyl" refers to at least one halo group (selected from F, Cl, Br or I), linked to an alkyl group as defined above (i.e. halo$C_{1-8}$alkyl). Examples of such haloalkyl groups include, but are not limited to, trifluoromethyl, difluoromethyl and fluoromethyl groups. The term "haloC$_{1-8}$alkyl" refers to at least one halo group linked an alkyl chain having 1 to 8 carbon atoms. Unless set forth or recited to the contrary, all haloalkyl groups described herein may be straight chain or branched.

The term "haloalkoxy" refers to an alkoxy group substituted with one or more halogen atoms (i.e. haloC$_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy. Unless set forth or recited to the contrary, all haloalkoxy groups described herein may be straight chain or branched.

The term "hydroxyC$_{1-8}$alkyl" refers to an C$_{1-8}$alkyl group as defined above wherein one to three hydrogen atoms on different carbon atoms are replaced by hydroxyl groups (i.e. hydroxyC$_{1-4}$alkyl). Examples of hydroxyC$_{1-8}$alkyl moieties include, but are not limited to —CH$_2$OH and —C$_2$H$_4$OH.

The term "cycloalkyl" denotes a non-aromatic mono or multicyclic ring system of 3 to about 12 carbon atoms, (i.e. C$_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "C$_{3-6}$cycloalkyl" refers to the cyclic ring having 3 to 6 carbon atoms. Examples of "C$_{3-6}$cycloalkyl" include but are not limited to cyclopropyl, cyclobutyl, cyclopentyl, or cyclohexyl.

The term "cycloalkylalkyl" refers to a cyclic ring-containing radical having 3 to about 6 carbon atoms directly attached to an alkyl group (e.g. C$_{3-6}$cycloalkylC$_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "aryl" refers to an aromatic radical having 6 to 14 carbon atoms (i.e. C$_{6-14}$aryl), including monocyclic, bicyclic and tricyclic aromatic systems, such as phenyl, naphthyl, tetrahydronapthyl, indanyl, and biphenyl.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds of formula (I), (II) or (III) may contain asymmetric or chiral centers, and, therefore, exist in different stereoisomeric forms. It is intended that all stereoisomeric forms of the compounds of formula (I), (II) or (III) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by the reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centers of the present invention can have the S or R configuration as defined by the IUPAC 1974.

Pharmaceutical Compositions

The compounds of the invention are typically administered in the form of a pharmaceutical composition. The pharmaceutical compositions described herein comprise one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifyingu agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical compositions described herein may also include one or more pharmaceutically acceptable auxiliary agents, wetting agents, suspending agents, preserving agents, buffers, sweetening agents, flavouring agents, colorants or any combination of the foregoing.

Administration of the compounds of the invention, in pure form or in an appropriate pharmaceutical composition, can be carried out using any route of administration, such as orally or parenterally. The route of administration may be any route which effectively transports the active compound of the patent application to the appropriate or desired site of action.

Methods of Treatment

The compounds of the present invention are particularly useful because they inhibit the activity of retinoid-related orphan receptor gamma, particularly retinoid-related orphan receptor gamma t (RORγt), i.e., they prevent, inhibit, or suppress the action of RORγt, and/or may elicit a RORγt modulating effect. Compounds of the invention are therefore useful in the treatment of those conditions in which inhibition of ROR gamma activity, and particularly RORγt, is beneficial.

The compounds of the present patent application are modulators of RORγt and can be useful in the treatment of diseases or disorder mediated by RORγt. Accordingly, the compounds and the pharmaceutical compositions of this invention may be useful in the treatment of inflammatory, metabolic and autoimmune diseases mediated by RORγt.

The term "autoimmune diseases" will be understood by those skilled in the art to refer to a condition that occurs when the immune system mistakenly attacks and destroys healthy body tissue. An autoimmune disorder may result in the destruction of one or more types of body tissue, abnormal growth of an organ, and changes in organ function. An autoimmune disorder may affect one or more organ or tissue types which include, but are not limited to, blood vessels, connective tissues, endocrine glands such as the thyroid or pancreas, joints, muscles, red blood cells, and skin. Examples of autoimmune (or autoimmune-related) disorders include multiple sclerosis, arthritis, rheumatoid arthritis, psoriasis, Crohn's disease, gastrointestinal disorder, inflammatory bowel disease, irritable bowel syndrome, colitis, ulcerative colitis, Sjorgen's syndrome, atopic dermatitis, optic neuritis, respiratory disorder, chronic obstructive pulmonary disease (COPD), asthma, type I diabetes, neuromyelitis optica, Myasthenia Gavis, uveitis, Guillain-Barre syndrome, psoriatic arthritis, Gaves' disease, allergy, osteoarthritis, Kawasaki disease, mucosal leishmaniasis, Hashimoto's thyroiditis, Pernicious anemia, Addison's disease, Systemic lupus erythematosus, Dermatomyositis, Sjogren syndrome, Lupus erythematosus, Myasthenia gravis, Reactive arthritis, Celiac disease—sprue (gluten-sensitive enteropathy), Graves's disease, thymopoiesis and Lupus.

Compounds of the present patent application may also be useful in the treatment of inflammation. The term "inflammation" will be understood by those skilled in the art to include any condition characterized by a localized or a systemic protective response, which may be elicited by physical trauma, infection, chronic diseases, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this present patent application, inflammatory pain, pain generally and/or fever.

The compounds of the present invention may be used for treatment of arthritis, including, but are not limited to, rheumatoid arthritis, osteoarthritis, psoriatic arthritis, septic arthritis, spondyloarthropathies, gouty arthritis, systemic lupus erythematosus and juvenile arthritis, osteoarthritis, collagen-induced arthritis (CIA) and other arthritic conditions.

The compounds of the present invention may be used for treatment of respiratory disorders including, but are not limited to, chronic obstructive pulmonary disease (COPD), asthma, bronchospasm, and cough.

Other respiratory disorders include, but are not limited to, bronchitis, bronchiolitis, bronchiectasis, acute nasoparyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, and mediastinitis.

The compounds of the present invention may also be used for treatment of pain conditions. The pain can be acute or chronic pain. Thus, the compounds of the present invention may be used for treatment of e.g., inflammatory pain, arthritic pain, neuropathic pain, post-operative pain, surgical pain, visceral pain, dental pain, premenstrual pain, central pain, cancer pain, pain due to burns, migraine or cluster headaches, nerve injury, neuritis, neuralgias, poisoning, ischemic injury, interstitial cystitis, viral, parasitic or bacterial infection, post-traumatic injury, or pain associated with irritable bowel syndrome.

The compounds of the present invention may further be used for treatment of gastrointestinal disorder such as, but not limited to, irritable bowel syndrome, inflammatory bowel disease, colitis, ulcerative colitis, biliary colic and other biliary disorders, renal colic, diarrhea-dominant IBS, and pain associated with gastrointestinal distension.

In addition, the compounds of the present invention may be useful in the treatment of cancer, and pain associated with cancer. Such cancers include, e.g., multiple myeloma and bone disease associated with multiple myeloma, melanoma, medulloblastoma, acute myelogenous leukemia (AML), head and neck squamous cell carcinoma, hepatocellular carcinoma, gastric cancer, bladder carcinoma and colon cancer.

The compounds of the present invention may be useful in a treatment of disease, disorder, syndrome or condition selected from the group consisting of chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease.

Any of the methods of treatment described herein comprise administering an effective amount of a compound according to Formula (I), (II) or (III), or a pharmaceutically-acceptable salt thereof, to a subject (particularly a human) in need thereof.

The present inventions further relates to the use of the compounds described herein in the preparation of a medicament for the treatment of diseases mediated by RORγt.

The compounds of the invention are effective both in the therapeutic and/or prophylactic treatment of the above-mentioned conditions. For the above-mentioned therapeutic uses the dosage administered may vary with the compound employed, the mode of administration, the treatment desired and the disorder.

The daily dosage of the compound of the invention administered may be in the range from about 0.05 mg/kg to about 100 mg/kg.

General Methods of Preparation

The compounds, described herein, including those of general formula (Ia), (Ib), (Ic), (Ib-i), (IIa), various intermediates and specific examples are prepared through the synthetic methods as depicted in Schemes 1 to 10. Furthermore, in the following schemes, where specific acids, bases, reagents, coupling reagents, solvents, etc. are mentioned, it is understood that other suitable acids, bases, reagents, coupling reagents, solvents etc. may be used and are included within the scope of the present invention. The modifications to reaction conditions, for example, temperature, duration of the reaction or combinations thereof, are envisioned as part of the present invention. The compounds obtained using the general reaction sequences may be of insufficient purity. These compounds can be purified using any of the methods for purification of organic compounds known to persons skilled in the art, for example, crystallization or silica gel or alumina column chromatography using different solvents in suitable ratios. All possible geometrical isomers and stereoisomers are envisioned within the scope of this invention.

The starting materials used herein are commercially available or were prepared by methods known in the art to those of ordinary skill or by methods disclosed herein. In general, the intermediates and compounds of the present invention can be prepared through the reaction schemes as follows. In some cases the final product may be further modified, for example, by manipulation of substituents. These manipulations may include, but are not limited to, reduction, oxidation, alkylation, acylation, hydrolysis, and cleavage of protecting groups etc., by following procedures known in the art of organic synthesis.

A general approach for the preparation of compounds of the formulae (Ia), (Ib) and (Ic) (wherein $R^1$, $R^2$, $R^3$, $R^4$, $R^5$, $R^6$, 'n', 'm' and 'p' are as defined with respect to a compound of formula (I) & $R^a$ and $R^b$ are $C_{1-8}$ alkyl in formulae (Ib) and (Ic)) is depicted in synthetic scheme 1.

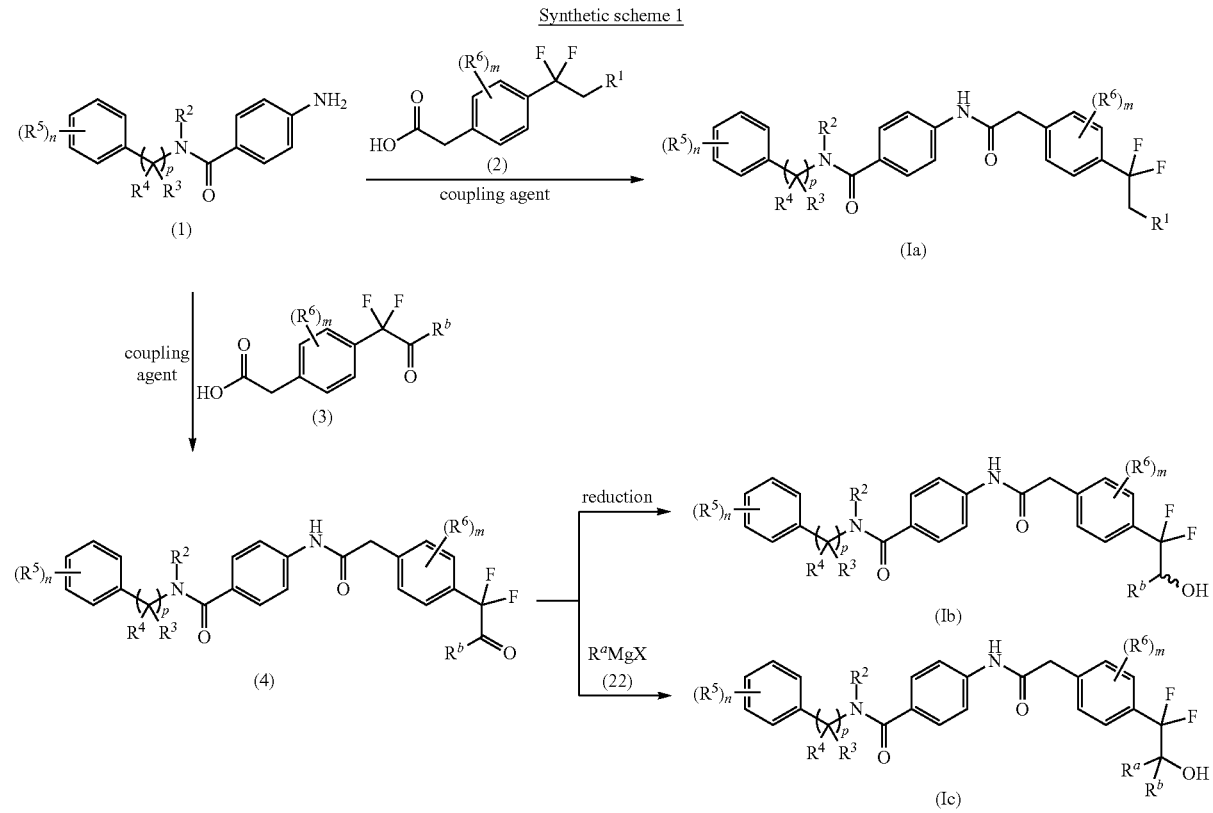

Synthetic scheme 1

The acid-amine coupling of compound of formula (1) with compound of formula (2) in the presence of a suitable coupling agent(s) and suitable base gives compound of formula (Ia). The suitable coupling agent(s) may be 1-ethyl-3-(3-dimethylaminopropyl)carbodiimide (EDCI), N,N'-dicyclohexylcarbodiimide (DCC), propyl phosphonic anhydride (T3P) or (1-[bis(dimethylamino)methylene]-1H-1,2,3-triazolo[4,5-b]pyridinium 3-oxid hexafluorophosphate) (HATU). The suitable base used in the reaction may be Et₃N, DIPEA, pyridine or DMAP. The acid amine coupling reaction may be carried out in a suitable solvent such as $CH_2Cl_2$, $CHCl_3$, DMF and THF or mixture thereof. Alternatively, coupling of compound of formula (1) with compound of formula (3) in the presence of a suitable coupling agent(s) and suitable base gives the keto compound of formula (4). The reduction of keto group of compound of formula (4) using suitable reducing agent in a suitable solvent gives the corresponding racemic hydroxyl compound of formula (Ib). The suitable reducing agent may be sodium borohydride and the suitable solvent may be methanol. Alternatively, compound of formula (4) on reaction with suitable Grignard reagent of formula (22) (wherein $R^a$ is $C_{1-8}$ alkyl and X is halogen) in a suitable solvent such as THF gives compound of formula (Ic).

An alternate approach for the preparation of compounds of the formulae (Ib) (wherein $R^2$, $R^3$, $R^4$, $R^5$, $R^6$, 'n', 'm' and 'p' are as defined with respect to a compound of formula (I) & $R^b$ is $C_{1-8}$ alkyl) is depicted in synthetic scheme 2.

The acid-amine coupling of compound of formula (1) with compound of formula (5) in the presence of a suitable coupling agent(s) and suitable base gives ester compound of formula (6). The suitable coupling agent(s) may be 1-ethyl-3-(3-dimethylaminopropyl)carbodiimide (EDCI), N,N'-dicyclohexylcarbodiimide (DCC), propyl phosphonic anhydride (T3P) or (1-[bis(dimethylamino)methylene]-1H-1,2,3-triazolo[4,5-b]pyridinium 3-oxid hexafluorophosphate) (HATU). The suitable base used in the reaction may be Et₃N, DIPEA, pyridine or DMAP. The acid amine coupling reaction may be carried out in a suitable solvent such as $CH_2Cl_2$, $CHCl_3$, DMF and THF or mixture thereof. The reaction of alkyl lithium compound of formula $R^b$—Li with the ester compound of formula (6) in the presence of suitable solvent gives the ketone compound of formula (4). The reduction of keto group of compound of formula (4) using suitable reducing agent in a suitable solvent gives the corresponding racemic hydroxyl compound of formula (Ib). The suitable reducing agent may be sodium borohydride and the suitable solvent may be methanol.

A general approach for the preparation of compounds of the formulae (Ib-i) (wherein $R^1$, $R^2$, $R^3$, $R^4$, $R^5$, $R^6$, 'n', 'm' and 'p' are as defined with respect to a compound of formula (I) & $R^b$ is $C_{1-8}$ alkyl) is depicted in synthetic scheme 3.

Synthetic scheme 2

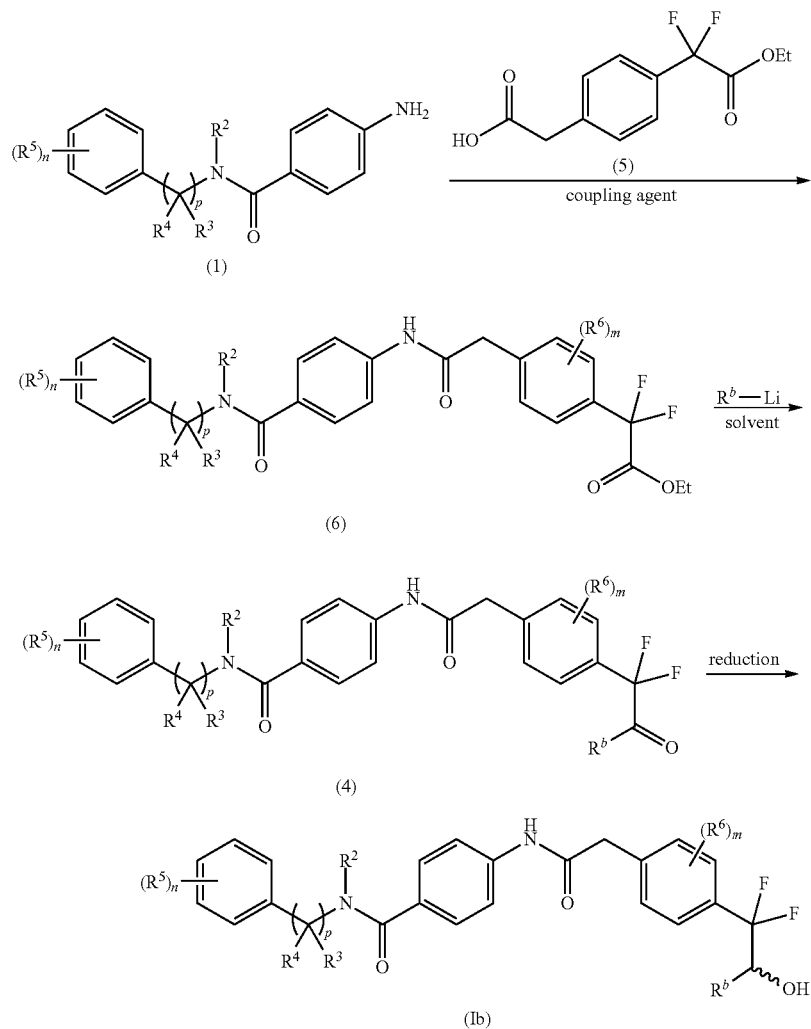

Synthetic scheme 3

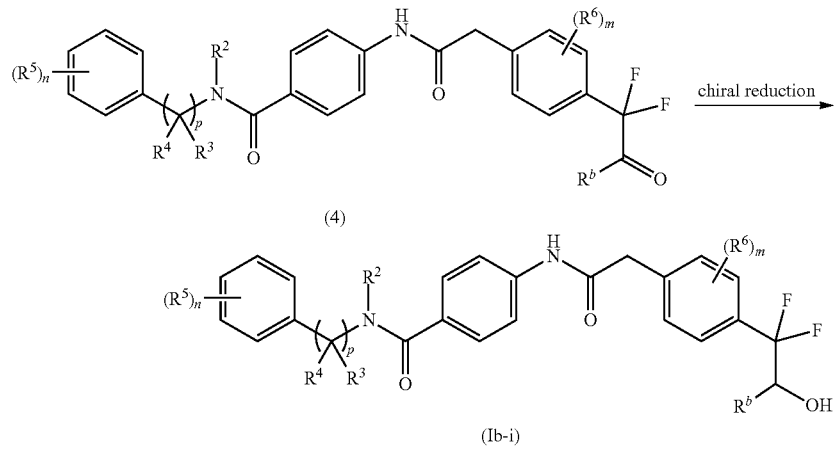

The chiral reduction of keto group of compound of formula (4) using suitable chiral reducing agent in a suitable solvent yields one of the isomer of hydroxyl compound of formula (Ib-i) as a major product. The chiral reduction may be carried out using (R or S)-2-methyl-CBS-oxazaborolidine in the presence of borane dimethyl sulfide, hydrogenation using BINAP-Ru dihalide, $H_2$/ruthenium (diphosphane)$_2$ (diamine)$_2$ complex, etc. The suitable solvent may be THF, DCM or DMF. The obtained isomer may be further purified according to various purification techniques known in the art.

An approach for the preparation of compound of formula (IIa) (wherein $R^2$, $R^5$, and 'n', are as defined with respect to a compound of formula (I)) is depicted in the synthetic scheme 4.

Synthetic scheme 4

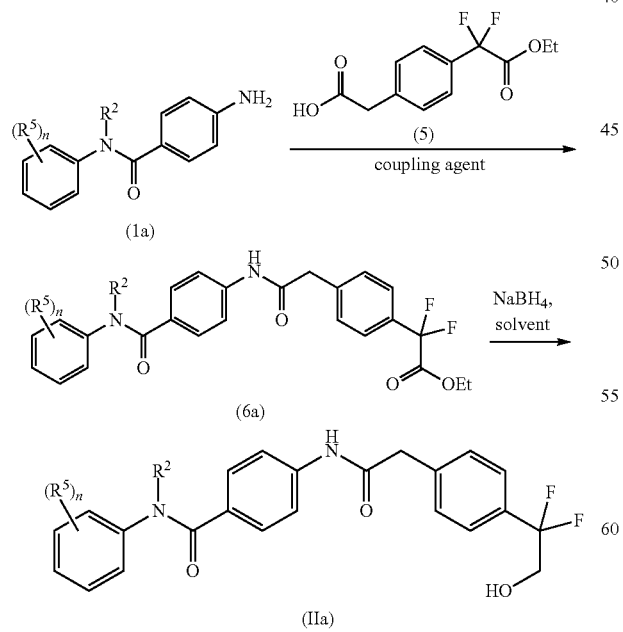

The acid-amine coupling of amine compound of formula (Ia) with carboxylic acid of formula (5) in the presence of a suitable coupling agent(s) and suitable base gives ester compound of formula (6a). The suitable coupling agent(s) may be 1-ethyl-3-(3-dimethylaminopropyl)carbodiimide (EDCI), N,N'-dicyclohexylcarbodiimide (DCC), propyl phosphonic anhydride (T3P) or (1-[Bis(dimethylamino)methylene]-1H-1,2,3-triazolo[4,5-b]pyridinium 3-oxid hexafluorophosphate) (HATU). The suitable base used in the reaction may be Et$_3$N, DIPEA, pyridine or DMAP. The reduction of the ester group of compound of formula (6a) using suitable reducing agent such as sodium borohydride in a suitable polar solvent such as methanol gives the hydroxyl compound of formula (IIa).

A general approach for the preparation of compound of formula (2) (wherein R, is as defined with respect to a compound of formula (I)) is depicted in the synthetic scheme 5.

Synthetic scheme 5

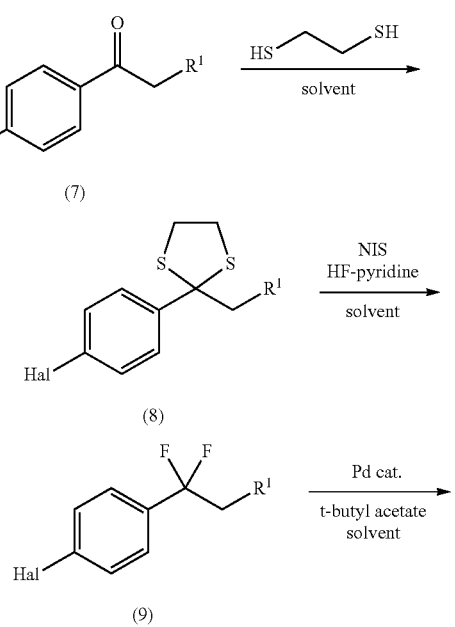

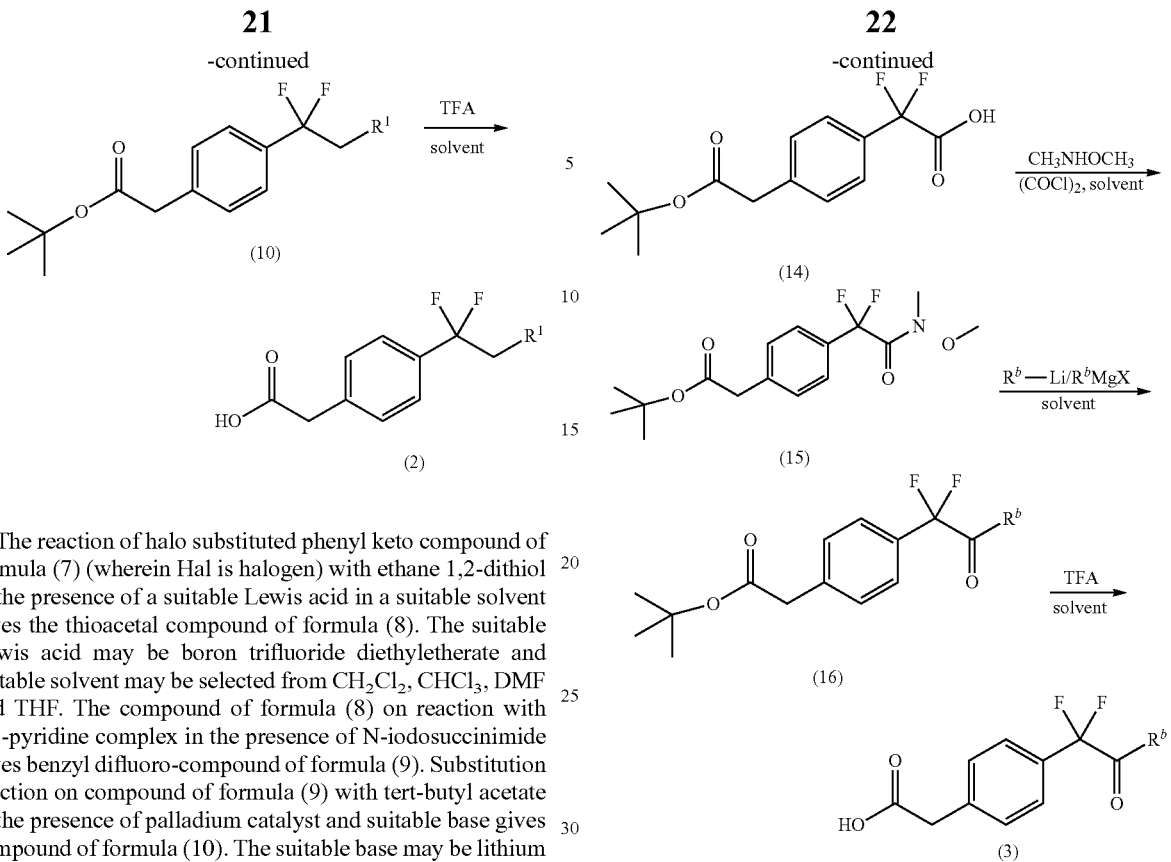

The reaction of halo substituted phenyl keto compound of formula (7) (wherein Hal is halogen) with ethane 1,2-dithiol in the presence of a suitable Lewis acid in a suitable solvent gives the thioacetal compound of formula (8). The suitable Lewis acid may be boron trifluoride diethyletherate and suitable solvent may be selected from $CH_2Cl_2$, $CHCl_3$, DMF and THF. The compound of formula (8) on reaction with HF-pyridine complex in the presence of N-iodosuccinimide gives benzyl difluoro-compound of formula (9). Substitution reaction on compound of formula (9) with tert-butyl acetate in the presence of palladium catalyst and suitable base gives compound of formula (10). The suitable base may be lithium dicyclohexylamine. The compound of formula (10) on deprotection of tert-butyl group, using trifluoroacetic acid in a suitable solvent furnishes the carboxylic acid of formula (2). The suitable solvent may be selected from $CH_2Cl_2$, $CHCl_3$, DMF and THF.

A general approach for the preparation of compound of formula (3) (wherein $R^b$ is $C_{1-8}$alkyl) is depicted in the synthetic scheme 6.

The condensation of suitably substituted halo phenyl acetic acid compound of formula (11) (wherein Hal is halogen) with ethyl bromo(difluoro)acetate gives the difluoro ester compound of formula (12). The acid group in compound of formula (12) is protected with tert-butyl bromide to give compound of formula (13). Selective hydrolysis of ethyl ester in compound of formula (13) using lithium hydroxide monohydrate in a suitable solvent gives the acid compound of formula (14). The suitable solvent may be THF, methanol, water or mixture thereof. The reaction of compound (14) with oxalyl chloride gives the corresponding acid chloride which on reaction with N,O-dimethylhydroxylamine hydrochloride in the presence of a base and in a suitable solvent gives the Weinreb amide compound of formula (15). The suitable solvent used may be $CH_2Cl_2$ or THF. The compound of formula (15) on reaction with alkyl lithium or suitable Grignard reagent in a suitable solvent such as THF gives the ketone compound of formula (16). The ester hydrolysis of compound of formula (16) using suitable reagent such as trifluoroacetic acid in a suitable solvent such as $CH_2Cl_2$ affords the carboxylic acid compound of formula (3).

An approach for the preparation of compound of formula (23) (wherein R' is $C_{1-8}$alkyl) is depicted in the synthetic scheme 7.

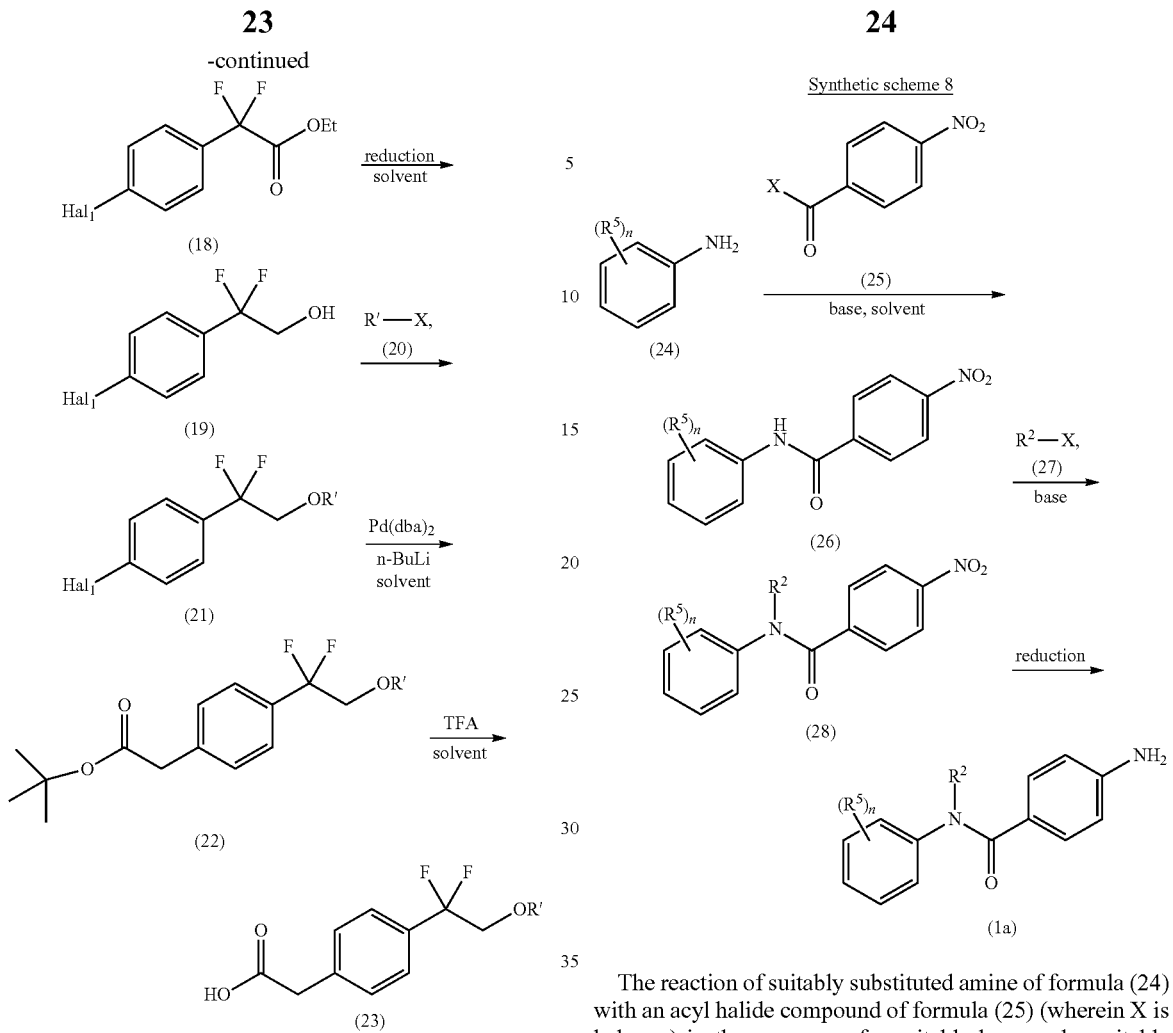

The reaction of di-halo compound of formula (17) (wherein $Hal_1$ and $Hal_2$ are halogen) with ethyl bromo (difluoro)acetate in the presence of copper powder and suitable solvent gives the difluoro ester compound of formula (18). The compound of formula (18) on reduction using suitable reducing agent in suitable conditions gives the hydroxyl compound of formula (19). The suitable reducing agent may be sodium borohydride and the solvent can be selected from methanol, IPA or ethanol. The reaction of compound of formula (19) with an alkylating compound of formula (20) (where R' is $C_{1-8}$alkyl and X is halogen) using a suitable base in a suitable solvent gives the compound of formula (21). The suitable base may be sodium hydride and the solvent may be selected from $CH_2Cl_2$, $CHCl_3$, DMF and THF or combination thereof. The halo-substitution of compound of formula (21) with tert-butyl acetate in the presence of palladium catalyst gives compound of formula (22). The compound of formula (22) on treatment with trifluoroacetic acid in a suitable solvent such as THF affords the carboxylic acid compound of formula (23).

A general approach for the preparation of compound of formula (Ia) (wherein $R^2$, $R^5$ and 'n', are as defined with respect to a compound of formula (I)) is depicted in the synthetic scheme 8.

The reaction of suitably substituted amine of formula (24) with an acyl halide compound of formula (25) (wherein X is halogen) in the presence of a suitable base under suitable reaction conditions gives the amide compound of formula (26). The suitable base may be $Et_3N$, DIPEA, pyridine or DMAP. The reaction may be carried out in a suitable solvent, selected from $CH_2Cl_2$, $CHCl_3$, DMF and THF or combination thereof. The reaction of compound of formula (26) with an alkylating agent of formula (27) (where X is halogen) using a suitable base such as sodium hydride gives compound of formula (28). The reduction of nitro group of compound of formula (28) using iron powder in the presence of aqueous acetic acid or ammonium chloride yields the corresponding amine compound of formula (Ia).

A general approach for the synthesis of compound of formula (Ib) (wherein $R^2$, $R^4$, $R^5$ and 'n', are as defined with respect to a compound of formula (I)) is depicted in synthetic scheme 9.

Synthetic scheme 9

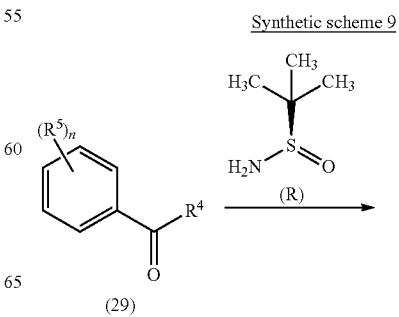

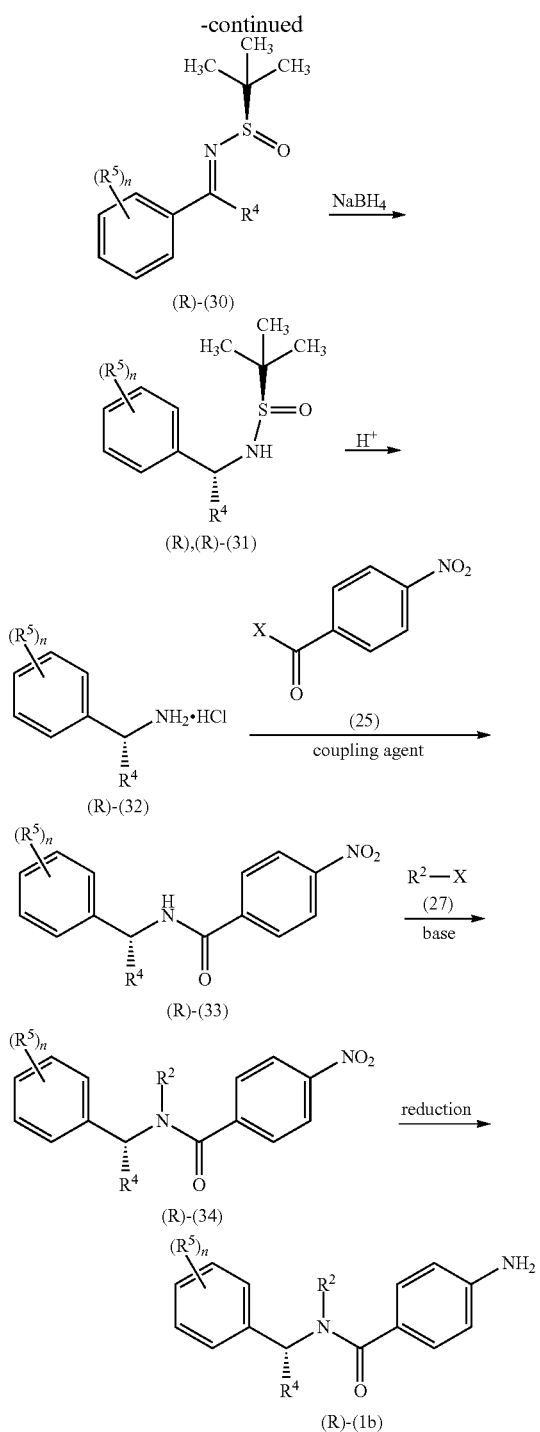

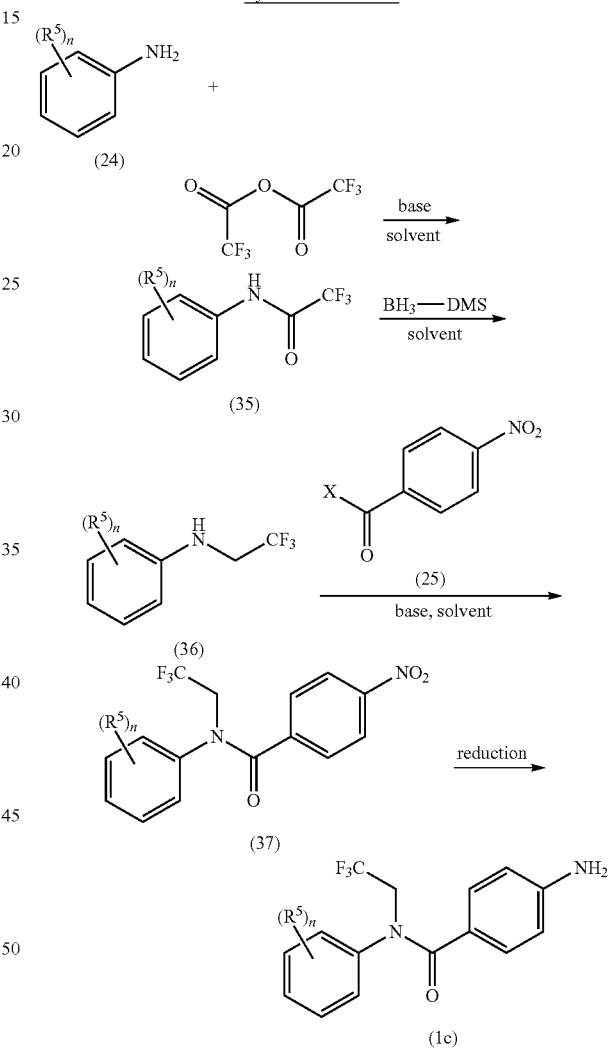

suitable base provides the amide compound of formula (33). The alkylation of compound of formula (33) using a suitable alkyl halide of formula (27) in the presence of suitable base such as sodium hydride gives the compound of formula (34). The reduction of compound of formula (34) iron powder in the presence of aqueous acetic acid or ammonium chloride affords the amine compound of formula (Ib).

A general approach for the preparation of compounds of formulae (Ic) (wherein $R^5$ and 'n', are as defined with respect to a compound of formula (I)) is depicted in the synthetic scheme 10.

A suitably substituted alkyl aryl ketone of formula (29) on reaction with (R)-2-methylpropane-2-sulfinamide in the presence of a suitable dehydrating agent gives the imine compound of formula (30). The reduction of imino group of compound of formula (30) using sodium borohydride in a suitable solvent gives predominantly the (R),(R)-diastereomer compound of formula (31). The suitable solvent may be THF. The acid catalyzed reaction of compound of formula (31) for removal of chiral auxiliary gives the amine compound of formula (32) as its acid addition salt. The coupling of amine compound of formula (32) with acid chloride compound of formula (25) in the presence of The reaction of suitably substituted amine compound of formula (24) with trifluoroacetic anhydride in the presence of suitable base gives the amide compound of formula (35). The suitable base may be triethylamine or N,N'-diisopropylethylamine. The amide compound of formula (35) on reduction using borane dimethylsulfide yields the corresponding amine compound of formula (36) which on coupling with acyl halide compound of formula (25) (wherein X is halogen) in the presence of a suitable base under suitable reaction conditions gives the nitro compound of formula (37). The suitable base may be $Et_3N$, DIPEA, pyridine or DMAP. The reaction may be carried out in a suitable solvent or mixture thereof. The suitable solvent may be selected from CH$_2$Cl$_2$, CHCl$_3$, DMF and THF or combination thereof. The reduction of nitro group of compound of formula (37) using iron powder in the presence of aqueous acetic acid or ammonium chloride yields the corresponding amine compound of formula (Ic).

Experimental Section

Unless otherwise stated, work-up includes distribution of the reaction mixture between the organic and aqueous phase indicated within parentheses, separation of layers and drying the organic layer over sodium sulfate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses.

The abbreviations, symbols and terms used in the examples and assays have the following meanings throughout: DCM: dichloromethane; DMSO-d$_6$: Hexadeuterodimethyl sulfoxide; DMSO dimethyl sulfoxide; $^1$H NMR: Proton Nuclear Magnetic Resonance; DMF: N,N-dimethyl formamide; EDCI.HCl: 1-ethyl-3-(3-dimethylaminopropyl) carbodiimide hydrochloride; HOBT: 1-hydroxybenzotriazole; NaOH: Sodium Hydroxide; KOH: Potassium Hydroxide; LiOH: Lithium Hydroxide; DIPEA: N,N-diisopropylethylamine; THF: Tetrahydofuran; HCl: hydrochloric acid; Na$_2$SO$_4$: Sodium sulfate; J: Coupling constant in units of Hz; h: hour(s); RT or rt: Room temperature (22-26° C.); o: ortho; m:meta; p: para; APCI-MS: Atmospheric Pressure Chemical Ionization Mass Spectrometry; MHz: Megahertz

INTERMEDIATES

Intermediate 1

4-Amino-N-(4-chlorophenyl)-N-methylbenzamide

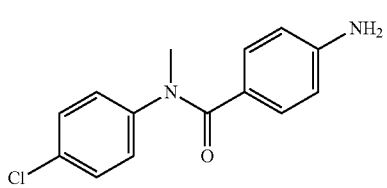 [SMILES: CN(C(=O)c1ccc(N)cc1)c1ccc(Cl)cc1]

Step 1: N-(4-Chlorophenyl)-4-nitrobenzamide

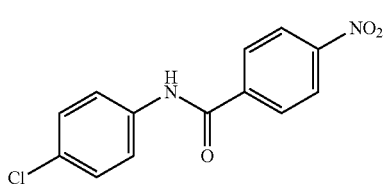 [SMILES: O=C(Nc1ccc(Cl)cc1)c1ccc([N+](=O)[O-])cc1]

To a stirred solution of 4-chloroaniline (2.5 g, 19.59 mmol) and triethylamine (8.2 mL, 58.79 mmol) in dichloromethane (20 mL) at 0° C. was added 4-nitrobenzoyl chloride (3.64 g, 19.59 mmol). The mixture was stirred for 3 h at RT. The reaction mixture was poured into water (50 mL) and extracted with ethyl acetate (150 mL×3). The combined organic layers were washed with brine (200 mL), dried over anhydrous sodium sulfate, filtered and concentrated. The crude material obtained was triturated in diethyl ether to yield 4.2 g of the titled product. $^1$H NMR (300 MHz, DMSO-d$_6$) δ 7.44 (d, J=9.0 Hz, 2H), 7.82 (d, J=9.0 Hz, 2H), 8.17 (d, J=8.7 Hz, 2H), 8.39 (d, J=8.7 Hz, 2H), 10.68 (s, 1H).

Step 2:
N-(4-Chlorophenyl)-N-methyl-4-nitrobenzamide

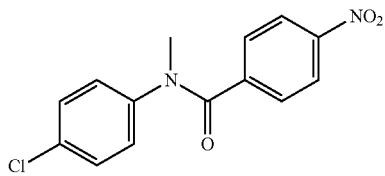 [SMILES: CN(C(=O)c1ccc([N+](=O)[O-])cc1)c1ccc(Cl)cc1]

To a stirred solution of Step 1 intermediate (4.08 g, 14.74 mmol) in DMF (20 mL) was added sodium hydride (60% w/w, 766 mg, 19.16 mmol) at 0° C. and the mixture was stirred for 10☐15 min at RT. Methyl iodide (1.1 mL, 17.69 mmol) was added to the mixture and stirred at RT for 3 h. The reaction was quenched with aqueous ammonium chloride (30 mL) and poured into water (40 mL). The aqueous mixture was extracted with ethyl acetate (150 mL×2). The combined organic layers were washed with brine (200 mL), dried over anhydrous sodium sulfate, filtered and concentrated under reduced pressure. The residue obtained was triturated in diethyl ether to yield 4.1 g of the desired compound. The intermediate was as such taken for the next step without characterization.

Step 3:
4-Amino-N-(4-chlorophenyl)-N-methylbenzamide

To a suspension of Step 2 intermediate (4.2 g, 14.45 mmol) and ammonium chloride (7.7 g, 145 mmol) in a mixture of ethanol and water (5:1, 120 mL) at 90° C. was added iron powder (2.42 g, 43.35 mmol) and the mixture was stirred at 90° C. for 1 h. The reaction mixture was cooled to RT and ethanol was distilled out under vacuum to obtain a thick residue. The residue was diluted with ethyl acetate (100 mL), washed with aqueous sodium bicarbonate (100 mL) and brine (100 mL). The organic layer was dried over anhydrous sodium sulfate, filtered and concentrated to yield 3.2 g of the titled product. $^1$H NMR (300 MHz, DMSO-d$_6$) δ 3.29 (s, 3H), 5.48 (s, 2H), 6.32 (d, J=8.4 Hz, 2H), 6.94 (d, J=8.4 Hz, 2H), 7.12 (d, J=8.1 Hz, 2H), 7.33 (d, J=8.1 Hz, 2H); ESI-MS (m/z) 261 (M+H)$^+$.

Intermediate 2

2-(4-(2-Ethoxy-1,1-difluoro-2-oxoethyl)phenyl)acetic acid

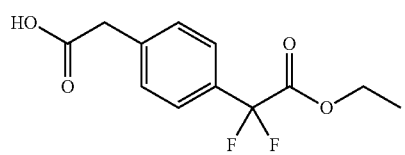 [SMILES: CCOC(=O)C(F)(F)c1ccc(CC(=O)O)cc1]

To a stirred suspension of 4-iodophenylacetic acid (203 mg, 0.76 mmol) and copper powder (193 mg, 3.05 mmol) in DMSO (8.0 mL) was added ethyl bromodifluoroacetate (196 mg, 1.52 mmol) at RT. The reaction mixture was stirred overnight at 60° C. in a sealed tube. The mixture was cooled to RT and quenched with aqueous ammonium chloride (30 mL). The aqueous mixture was further diluted with water (20 mL) and extracted with ethyl acetate (50 mL×2). The combined organic layers were dried over anhydrous sodium sulfate, filtered and concentrated under reduced pressure. The residue thus obtained was purified by silica gel column chromatography to yield 171 mg of the titled product. $^1$H NMR (300 MHz, DMSO-$d_6$) δ 1.22 (t, J=7.2 Hz, 3H), 3.67 (s, 2H), 4.31 (q, J=7.2 Hz, 2H), 7.44 (d, J=8.1 Hz, 2H), 7.53 (d, J=8.1 Hz, 2H), 12.44 (s, 1H).

Intermediate 3

2-(4-(1,1-Difluoropropyl)phenyl)acetic acid

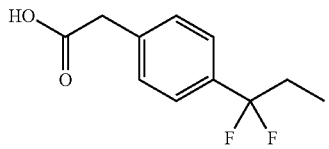

Step 1: 2-(4-Bromophenyl)-2-ethyl-1,3-dithiolane

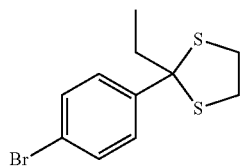

To a stirred solution of 4-bromopropiophenone (2.01 g, 9.43 mmol) in anhydrous dichloromethane (20 mL) were added boron trifluoride diethyletherate (0.49 mL, 4.71 mmol) and ethane 1,2-dithiol (1.57 mL, 18.8 mmol). The reaction mixture was stirred overnight at RT. The mixture was diluted with dichloromethane (10 mL), washed with 10% aqueous sodium hydroxide solution (10 mL), water (20 mL) followed by brine (20 mL). The organic layer was dried over anhydrous sodium sulfate, filtered and concentrated under reduced pressure to yield 2.21 g of the titled compound. $^1$H NMR (300 MHz, CDCl$_3$) δ 0.89 (t, J=7.5 Hz, 3H), 2.33 (q, J=7.5 Hz, 2H), 3.18-3.30 (m, 2H), 3.33-3.41 (m, 2H), 7.41 (d, J=8.1 Hz, 2H), 7.56 (d, J=8.1 Hz, 2H); APCI-MS (m/z) 288 (M)$^+$.

Step 2: 1-Bromo-4-(1,1-difluoropropyl)benzene

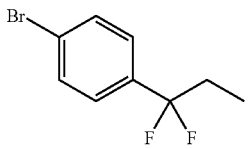

To a stirred solution of N-iodosuccinimide (704 mg, 3.13 mmol) in dichloromethane (5.0 mL) at −20° C. were added hydrogen fluoride in pyridine (70%, 0.52 mL, 20.88 mmol). After being stirred for 2 min, a solution of Step 1 intermediate (302 mg, 1.04 mmol) in dichloromethane (5.0 mL) was added and resulting mixture was stirred at −20° C. for 30 min. The reaction mixture was diluted with n-hexane (5.0 mL), filtered through basic alumina and the bed was washed with n-hexane (30 mL). The combined filtrates were concentrated and the residue obtained was diluted with ethyl acetate (50 mL). The solution was washed with 10% sodium thiosulfate (20 mL), 2% potassium permanganate (20 mL), water (20 mL) and brine (20 mL). The organic layer was dried over anhydrous sodium sulfate, filtered and concentrated. The residue obtained was purified by silica gel column chromatography to yield 203 mg of the titled product. $^1$H NMR (300 MHz, CDCl$_3$) δ 0.97 (t, J=7.5 Hz, 3H), 2.02-2.21 (m, 2H), 7.33 (d, J=8.1 Hz, 2H), 7.56 (d, J=8.1 Hz, 2H).

Step 3: tert-Butyl 2-(4-(1,1-difluoropropyl)phenyl)acetate

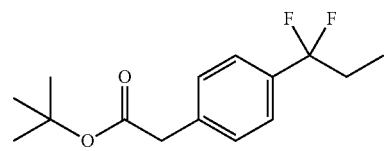 [SMILES: CCC(F)(F)c1ccc(CC(=O)OC(C)(C)C)cc1]

To a solution of dicyclohexylamine (1.8 g, 10.25 mmol) in anhydrous toluene (20 mL) at 0° C. was added n-butyl lithium (6.41 mL, 10.26 mmol, 1.6 M in hexane). After 5 min, tert-butyl acetate (1.15 mL, 8.55 mmol) was added to the mixture and stirred for 15 min at 0° C. In a separate flask, tri-tert-butylphosphonium tetrafluoroborate (248 mg, 0.85 mmol) and bis(dibenzylideneacetone) palladium (0) (245 mg, 0.42 mmol) were taken together and was evacuated and refilled with nitrogen thrice. The solid mixture was suspended in toluene (10 mL) and to this was added Step 2 intermediate (2.01 g, 8.55 mmol) followed by the first reaction mixture. The resulting mixture was stirred overnight at RT. The reaction mixture was diluted with diethyl ether (50 mL), filtered through celite bed and the bed was washed with diethyl ether (30 mL). The combined filtrates were concentrated and the residue obtained was purified by silica gel column chromatography to yield 1.43 g of the titled product. 1H NMR (300 MHz, CDCl$_3$) δ 0.98 (t, J=7.5 Hz, 3H), 1.44 (s, 9H), 2.04-2.22 (m, 2H), 3.55 (s, 2H), 7.31 (d, J=8.1 Hz, 2H), 7.41 (d, J=8.1 Hz, 2H).

Step 4: 2-(4-(1,1-Difluoropropyl)phenyl)acetic acid

To a stirred solution of Step 3 intermediate (1.42 g, 5.25 mmol) in dichloromethane (20 mL) at 0° C. was added trifluoroacetic acid (10 mL) and the mixture was stirred at RT for 1 h. The solvent was evaporated and the residue obtained was purified by silica gel column chromatography to afford 491 mg of the titled product. $^1$H NMR (300 MHz, DMSO-$d_6$) δ 0.90 (t, J=6.0 Hz, 3H), 2.11-2.28 (m, 2H), 3.63 (s, 2H), 7.33 (d, J=8.4 Hz, 2H), 7.42 (d, J=8.4 Hz, 2H), 12.42 (br s, 1H); APCI-MS (m/z) 213 (M−H)$^-$.

Intermediate 4

2-(4-(1,1-Difluoro-2-oxopropyl)phenyl)acetic acid

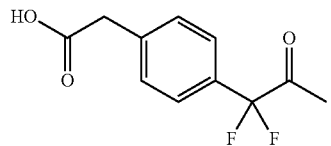 [SMILES: CC(=O)C(F)(F)c1ccc(CC(=O)O)cc1]

Step 1: Ethyl 2-(4-(2-(tert-butoxy)-2-oxoethyl)phenyl)-2,2-difluoroacetate

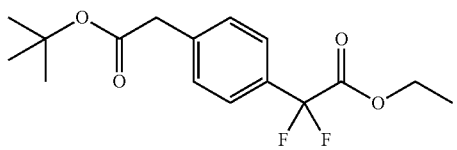 [SMILES: CCOC(=O)C(F)(F)c1ccc(CC(=O)OC(C)(C)C)cc1]

To a stirred solution of 2-(4-(2-ethoxy-1,1-difluoro-2-oxoethyl)phenyl)acetic acid (Intermediate 2) (3.3 g, 12.77 mmol) in a mixture of dichloromethane and THF (2:1, 90 mL) were added molecular sieves (3.3 g, 4 Å) and silver carbonate (10.58 g, 38.33 mmol). The reaction mixture was stirred, cooled to 0° C. and was added tert-butyl bromide (7.3 mL, 63.89 mmol) dropwise. The mixture was stirred overnight at RT. The reaction mixture was filtered through celite bed and washed with dichloromethane (100 mL). The filtrate was concentrated under reduced pressure and the residue obtained was purified by flash chromatography to yield 1.82 g of the titled product. The product was used for next step without characterisation.

Step 2: 2-(4-(2-(tert-Butoxy)-2-oxoethyl)phenyl)-2,2-difluoroacetic acid

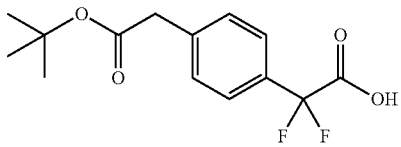 [SMILES: CC(C)(C)OC(=O)Cc1ccc(C(F)(F)C(=O)O)cc1]

To a stirred solution of Step 1 intermediate (915 mg, 2.91 mmol) in a mixture of THF, methanol and water (3:2:1, 30 mL) at 0° C. was added lithium hydroxide monohydrate (366 mg, 8.73 mmol) and the mixture was stirred for 1 h at RT. The reaction mixture was acidified with 1 N HCl till pH 2-3 and extracted with ethyl acetate (50 mL×2). The combined organic layers were dried over anhydrous sodium sulfate, filtered and concentrated under reduced pressure to afford 839 mg of the titled product. $^1$H NMR (300 MHz, DMSO-$d_6$) δ 1.40 (s, 9H), 3.64 (s, 2H), 7.40 (d, J=8.4 Hz, 2H), 7.52 (d, J=8.1 Hz, 2H).

Step 3: tert-Butyl 2-(4-(1,1-difluoro-2-(methoxy(methyl)amino)-2-oxoethyl)phenyl)acetate

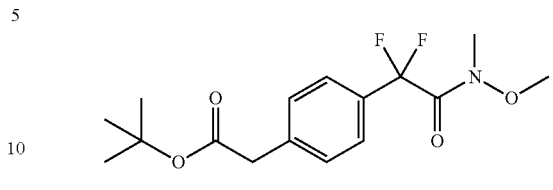

To a stirred solution of Step 2 intermediate (833 mg, 2.90 mmol) in dichloromethane (15 mL) at 0° C. were added oxalyl chloride (2.2 mL, 4.36 mmol) and 2 drops of DMF. The mixture was warmed to RT and stirred for 3 h. The mixture was concentrated under inert atmosphere to give an oily residue, which was diluted with dichloromethane (15 mL). The solution was cooled to 0° C. and was added N,O-dimethyl hydroxylamine hydrochloride (425 mg, 4.36 mmol) followed by triethylamine (1.6 mL, 11.63 mmol). The mixture was stirred overnight at RT. The mixture was diluted with dichloromethane (15 mL), washed with aqueous saturated sodium bicarbonate solution (20 mL) and brine (20 mL). The organic layer was dried over anhydrous sodium sulfate, filtered, concentrated and the residue obtained was purified by silica gel column chromatography to yield 581 mg of the desired product. $^1$H NMR (300 MHz, CDCl$_3$) δ 1.43 (s, 9H), 3.21 (s, 3H), 3.51 (s, 2H), 3.56 (s, 3H), 7.34 (d, J=7.8 Hz, 2H), 7.50 (d, J=7.8 Hz, 2H).

Step 4: tert-Butyl 2-(4-(1,1-difluoro-2-oxopropyl)phenyl)acetate

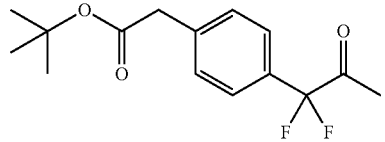 [SMILES: CC(=O)C(F)(F)c1ccc(CC(=O)OC(C)(C)C)cc1]

To a stirred solution of Step 3 intermediate (572 mg, 1.73 mmol) in THF (15 mL) at 0° C. was added methylmagnesium bromide (1.15 mL, 3.47 mmol) and the mixture was stirred at 0° C. for 2 h. The reaction was quenched with aqueous ammonium chloride solution (20 mL) and extracted with ethyl acetate (50 mL×2). The combined organic layers were washed with brine (50 mL), concentrated and the crude obtained was purified by silica gel column chromatography to yield 369 mg of the desired product. $^1$H NMR (300 MHz, CDCl$_3$) δ 1.43 (s, 9H), 2.31 (s, 3H), 3.56 (s, 2H), 7.36 (d, J=8.4 Hz, 2H), 7.50 (d, J=7.8 Hz, 2H), APCI-MS (m/z) 286 (M+H)$^+$.

Step 5: 2-(4-(1,1-Difluoro-2-oxopropyl)phenyl)acetic acid

The titled compound was prepared by the reaction of Step 4 intermediate (501 mg, 1.76 mmol) with trifluoroacetic acid (10 mL) in dichloromethane (10 mL) as per the procedure described in Step 4 of Intermediate 3 to afford 379 mg of the product. $^1$H NMR (300 MHz, DMSO-$d_6$) δ 2.36 (s, 3H), 3.66 (s, 2H), 7.43 (d, J=7.8 Hz, 2H), 7.52 (d, J=8.4 Hz, 2H), 12.22 (br s, 1H).

Intermediate 5

4-Amino-N-(2,5-dichlorophenyl)-N-methylbenzamide

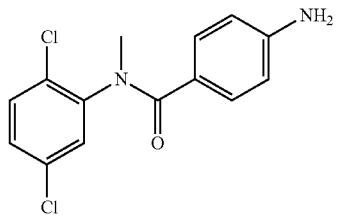 [SMILES: CN(C(=O)c1ccc(N)cc1)c1cc(Cl)ccc1Cl]

Step 1: N-(2,5-Dichlorophenyl)-4-nitrobenzamide

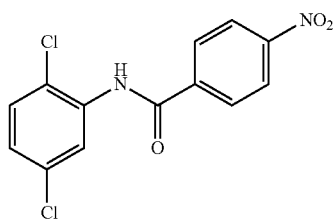 [SMILES: O=C(Nc1cc(Cl)ccc1Cl)c1ccc([N+](=O)[O-])cc1]

The titled compound was prepared by the reaction of 2,5-dichloroaniline (223 mg, 1.37 mmol) and 4-nitrobenzoyl chloride (256 mg, 1.37 mmol) in pyridine (5.0 mL) at refluxed temperature as per the procedure described in Step 1 of Intermediate 1 to yield 314 mg of the product. $^1$H NMR (300 MHz, DMSO-$d_6$) δ 7.41 (d, J=8.7 Hz, 1H), 7.62 (d, J=8.4 Hz, 1H), 7.76 (s, 1H), 8.19 (d, J=8.1 Hz, 2H), 8.39 (d, J=8.4 Hz, 2H), 10.55 (s, 1H).

Step 2: N-(2,5-Dichlorophenyl)-N-methyl-4-nitrobenzamide

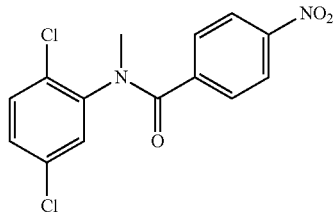

The titled compound was prepared by the reaction of Step 1 intermediate (309 mg, 0.99 mmol) with methyl iodide (93 μL, 1.48 mmol) using sodium hydride (60% w/w, 51.63 mg, 1.29 mmol) in anhydrous DMF (5.0 mL) as per the procedure described in step 2 of Intermediate 1 to yield 294 mg of the product. $^1$H NMR (300 MHz, CDCl$_3$) δ 3.40 (s, 3H), 7.19 (d, J=5.7 Hz, 2H), 7.25-7.32 (m, 1H), 7.50 (d, J=8.7 Hz, 2H), 8.04 (d, J=9.0 Hz, 2H).

Step 3: 4-Amino-N-(2,5-dichlorophenyl)-N-methylbenzamide

The titled compound was prepared by the reduction of Step 2 intermediate (286 mg, 0.87 mmol) using iron powder (245 mg, 4.39 mmol) and ammonium chloride (470 mg, 8.79 mmol) in a mixture of ethanol and water (3:1, 16 mL) as per the procedure described in step 3 of Intermediate 1 to obtain 197 mg of the product. $^1$H NMR (300 MHz, DMSO-$d_6$) δ 3.18 (s, 3H), 5.51 (s, 2H), 6.32 (d, J=8.1 Hz, 2H), 6.98 (d, J=8.1 Hz, 2H), 7.34 (d, J=8.7 Hz, 1H), 7.49 (d, J=8.4 Hz, 1H), 7.58 (s, 1H); APCI-MS (m/z) 295 (M+H)$^+$.

Intermediate 6

4-Amino-N-(2-chlorophenyl)-N-methylbenzamide

Step 1: N-(2-Chlorophenyl)-4-nitrobenzamide

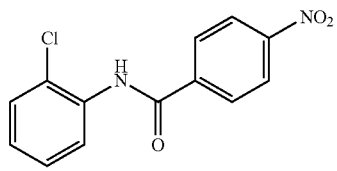 [SMILES: O=C(Nc1ccccc1Cl)c1ccc([N+](=O)[O-])cc1]

To a stirred solution of 2-chloroaniline (3.0 g, 23.51 mmol) in dichloromethane (60 mL) was added triethylamine (9.8 mL, 70.54 mmol) and cooled to 0° C. 4-Nitrobenzoyl chloride (4.36 g, 23.51 mmol) was added and the resulting mixture was stirred overnight at RT. The reaction was diluted with dichloromethane (50 mL), washed with water (50 mL) and brine (50 mL). The organic layer was dried over anhydrous sodium sulfate, filtered and concentrated to give an oily residue which was triturated with diethyl ether. The solid obtained was filtered and washed with diethyl ether (50 mL) to yield 3.8 g of the desired product. $^1$H NMR (300 MHz, DMSO-$d_6$) δ 7.31-7.43 (m, 2H), 7.58 (d, J=7.5 Hz, 2H), 8.20 (d, J=8.7 Hz, 2H), 8.38 (d, J=9.0 Hz, 2H), 10.45 (s, 1H).

Step 2: N-(2-Chlorophenyl)-N-methyl-4-nitrobenzamide

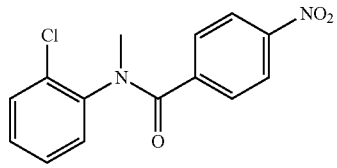 [SMILES: CN(C(=O)c1ccc([N+](=O)[O-])cc1)c1ccccc1Cl]

The titled compound was prepared by the reaction of Step 1 intermediate (2.0 g, 7.33 mmol) with methyl iodide (596 μL, 9.53 mmol) using sodium hydride (60% w/w, 352 mg, 8.80 mmol) in anhydrous DMF (20 mL) as per the procedure described in step 2 of Intermediate 1 to yield 2.1 g of the product. ¹H NMR (300 MHz, CDCl₃) δ 3.42 (s, 3H), 7.11-7.26 (m, 3H), 7.36 (d, J=7.2 Hz, 1H), 7.49 (d, J=8.7 Hz, 2H), 8.02 (d, J=9.0 Hz, 2H).

Step 3:
4-Amino-N-(2-chlorophenyl)-N-methylbenzamide

The titled compound was prepared by the reduction of Step 2 intermediate (2.05 g, 7.05 mmol) using iron powder (1.2 g, 21.15 mmol) and ammonium chloride (3.76 g, 70.51 mmol) in a mixture of ethanol and water (1:1, 50 mL) as per the procedure described in step 3 of Intermediate 1 to obtain 1.5 g of the product. ¹H NMR (300 MHz, DMSO-d₆) δ 3.18 (s, 3H), 5.45 (s, 2H), 6.28 (d, J=7.8 Hz, 2H), 6.96 (d, J=7.5 Hz, 2H), 7.28-7.33 (m, 3H), 7.46 (d, J=6.3 Hz, 1H).

Intermediate 7

2-(4-(1,1-Difluoro-2-methoxyethyl)phenyl)acetic acid

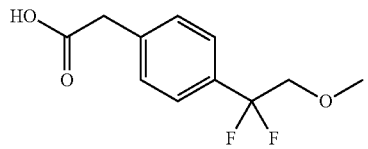 [SMILES: COCC(F)(F)c1ccc(CC(=O)O)cc1]

Step 1: Ethyl (4-bromophenyl)(difluoro)acetate

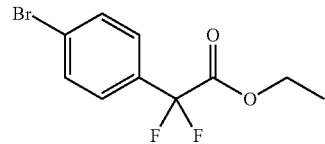

The titled compound was prepared by the reaction of 1-bromo-4-iodobenzene (1.0 g, 3.55 mmol) with ethyl bromo difluoroacetate (1.43 g, 7.06 mmol) using copper powder (903 mg, 14.2 mmol) in DMSO (10 mL) as per the procedure described in Intermediate 2 to yield 623 mg of the product. ¹H NMR (300 MHz, CDCl₃) δ 1.30 (t, J=7.2 Hz, 3H), 4.29 (q, J=7.2 Hz, 2H), 7.47 (d, J=8.4 Hz, 2H), 7.59 (d, J=8.4 Hz, 2H).

Step 2: 2-(4-Bromophenyl)-2,2-difluoroethanol

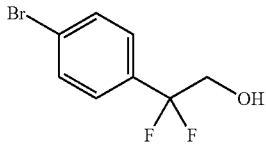 [SMILES: OCC(F)(F)c1ccc(Br)cc1]

To a stirred solution of Step 1 intermediate (206 mg, 0.73 mmol) in ethanol (4.0 mL) at −10° C. was added calcium chloride (25 mg, 0.22 mmol) followed by sodium borohydride (70 mg, 1.84 mmol). The resulting mixture was stirred at RT for 2 h. The reaction was quenched with aqueous saturated sodium bicarbonate solution (10 mL) and extracted with ethyl acetate (40 mL×2). The combined organic layers were washed with brine (50 mL), dried over anhydrous sodium sulfate, filtered and concentrated under reduced pressure. The residue obtained was purified by silica gel column chromatography to yield 176 mg of the titled product. 1H NMR (300 MHz, CDCl₃) δ 3.95 (t, J=13.2 Hz, 2H), 7.40 (d, J=8.4 Hz, 2H), 7.58 (d, J=8.1 Hz, 2H).

Step 3:
1-Bromo-4-(1,1-difluoro-2-methoxyethyl)benzene

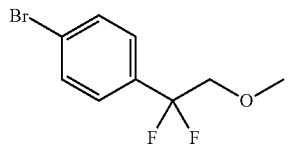

The titled compound was prepared by the reaction of Step 2 intermediate (170 mg, 0.71 mmol) with methyl iodide (68 μL, 1.07 mmol) using sodium hydride (60% w/w, 37 mg, 0.93 mmol) in anhydrous DMF (20 mL) as per the procedure described in step 2 of Intermediate 1 to yield 141 mg of the product. ¹H NMR (300 MHz, CDCl₃) δ 3.42 (s, 3H), 3.78 (t, J=12.6 Hz, 2H), 7.39 (d, J=8.1 Hz, 2H), 7.56 (d, J=8.4 Hz, 2H).

Step 4: tert-Butyl 2-(4-(1,1-difluoro-2-methoxyethyl)phenyl)acetate

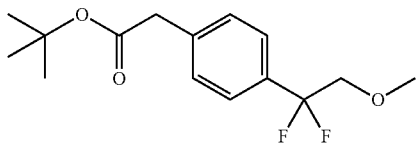 [SMILES: COCC(F)(F)c1ccc(CC(=O)OC(C)(C)C)cc1]

The titled compound was prepared by the reaction of Step 3 intermediate (506 mg, 2.01 mmol) with tert-butyl acetate (272 μL, 2.01 mmol) in the presence of n-butyl lithium (1.51 mL, 2.41 mmol), tri-tert-butyl phosphonium tetrafluoroborate (58 mg, 0.20 mmol) and bis(dibenzylidene)acetone palladium (0) (58 mg, 0.10 mmol) using dicyclohexylamine (782 μL, 2.41 mmol) in toluene (10 mL) as per the procedure described in Step 3 of Intermediate 3 to yield 398 mg of the product. ¹H NMR (300 MHz, CDCl₃) δ 1.44 (s, 9H), 3.43 (s, 3H), 3.55 (s, 2H), 3.79 (t, J=13.2 Hz, 2H), 7.34 (d, J=7.8 Hz, 2H), 7.46 (d, J=8.4 Hz, 2H).

Step 5:
2-(4-(1,1-Difluoro-2-methoxyethyl)phenyl)acetic acid

The titled compound was prepared by the reaction of Step 4 intermediate (386 mg, 1.38 mmol) with trifluoroacetic acid (3.0 mL) in dichloromethane (6.0 mL) as per the procedure described in Step 4 of Intermediate 3 to afford 161 mg of the product. ¹H NMR (300 MHz, DMSO-d₆) δ 3.31 (s, 3H), 3.62 (s, 2H), 3.86 (t, J=14.1 Hz, 2H), 7.35 (d, J=7.8 Hz, 2H), 7.46 (d, J=8.1 Hz, 2H), 12.41 (br s, 1H).

Intermediate 8

4-Amino-N-(3,5-dimethylphenyl)-N-methylbenzamide

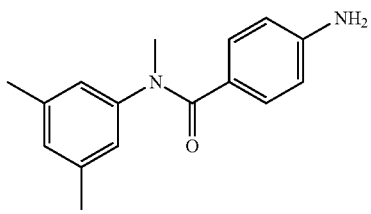

Step 1: N-(3,5-Dimethylphenyl)-4-nitrobenzamide

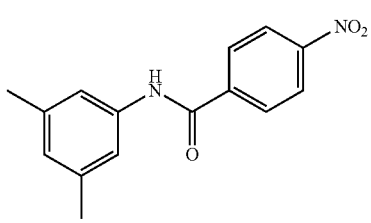 [SMILES: Cc1cc(C)cc(NC(=O)c2ccc([N+](=O)[O-])cc2)c1]

The titled compound was prepared by the reaction of 3,5-dimethylaniline (2.0 g, 16.50 mmol) and 4-nitrobenzoyl chloride (3.06 mg, 16.50 mmol) using N,N'-diisopropylethylamine (5.7 mL, 33.00 mmol) in dichloromethane (40 mL) as per the procedure described in Step 1 of Intermediate 1 to yield 3.4 g of the product. $^1$H NMR (300 MHz, DMSO-$d_6$) δ 2.27 (s, 6H), 6.78 (s, 1H), 7.40 (s, 2H), 8.16 (d, J=8.1 Hz, 2H), 8.36 (d, J=8.7 Hz, 2H), 10.41 (s, 1H).

Step 2: N-(3,5-Dimethylphenyl)-N-methyl-4-nitrobenzamide

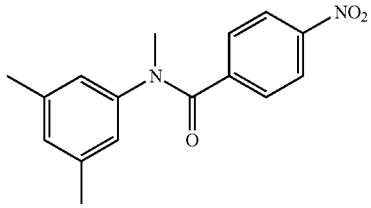 [SMILES: Cc1cc(C)cc(N(C)C(=O)c2ccc([N+](=O)[O-])cc2)c1]

The titled compound was prepared by the reaction of Step 1 intermediate (2.0 g, 7.39 mmol) with methyl iodide (600 μL, 9.61 mmol) using sodium hydride (60% w/w, 390 mg, 9.61 mmol) in anhydrous DMF (15 mL) as per the procedure described in step 2 of Intermediate 1 to yield 1.9 g of the product. $^1$H NMR (300 MHz, CDCl$_3$) δ 2.19 (s, 6H), 3.47 (s, 3H), 6.63 (s, 2H), 6.80 (s, 1H), 7.46 (d, J=8.4 Hz, 2H), 8.02 (d, J=8.7 Hz, 2H).

Step 3: 4-Amino-N-(3,5-dimethylphenyl)-N-methylbenzamide

The titled compound was prepared by the reduction of Step 2 intermediate (1.9 g, 6.68 mmol) using iron powder (1.2 g, 20.04 mmol) and ammonium chloride (3.6 g, 66.82 mmol) in a mixture of ethanol and water (5:1, 40 mL) as per the procedure described in step 3 of Intermediate 1 to obtain 1.6 g of the product. $^1$H NMR (300 MHz, CDCl$_3$) δ 2.21 (s, 6H), 3.42 (s, 3H), 6.46 (d, J=7.2 Hz, 2H), 6.66 (s, 2H), 6.77 (s, 1H), 7.17 (d, J=8.4 Hz, 2H).

Intermediate 9

4-Amino-N-(2'-fluoro-5-methylbiphenyl-3-yl)-N-methylbenzamide

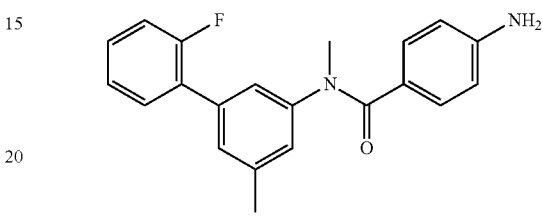

Step 1: 2'-Fluoro-5-methylbiphenyl-3-amine

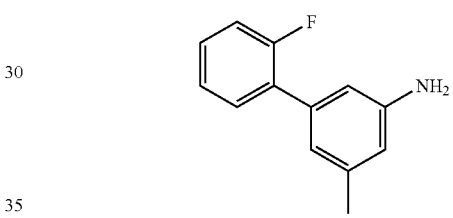

To a stirred solution of 3-bromo-5-methylaniline (504 mg, 2.68 mmol), 2-fluorophenyl boronic acid (413 mg, 2.95 mmol) and potassium carbonate (1.1 g, 8.04 mmol) in a mixture of DMF (15 mL) and water (5.0 mL) was added tetrakis(triphenylphosphine)palladium(0) (155 mg, 0.13 mmol) at RT. The reaction mixture was evacuated, flushed with nitrogen and stirred at 80° C. for 16 h. The reaction mixture was cooled to RT, diluted with ethyl acetate (30 mL), washed with water (30 mL) and brine (30 mL). The organic layer was concentrated under reduced pressure and purified by silica gel column chromatography to obtain 400 mg of the titled product. $^1$H NMR (300 MHz, DMSO-$d_6$) δ 2.18 (s, 3H), 5.07 (s, 2H), 6.38-6.51 (m, 3H), 7.18-7.25 (m, 2H), 7.30-7.41 (m, 2H); APCI-MS (m/z) 202 (M+H)$^+$.

Step 2: N-(2'-Fluoro-5-methylbiphenyl-3-yl)-4-nitrobenzamide

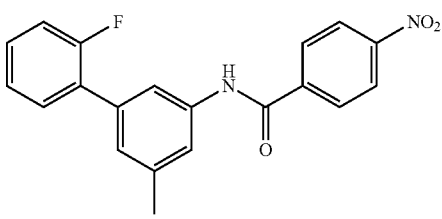 [SMILES: Cc1cc(NC(=O)c2ccc([N+](=O)[O-])cc2)cc(-c2ccccc2F)c1]

The titled compound was prepared by the reaction of Step 1 intermediate (375 mg, 1.86 mmol) and 4-nitrobenzoyl chloride (380 mg, 2.05 mmol) using triethylamine (510 μL, 3.72 mmol) in dichloromethane (10 mL) as per the procedure described in Step 1 of Intermediate 1 to yield 500 mg of the product. ¹H NMR (300 MHz, DMSO-d₆) δ 2.36 (s, 3H), 7.12 (s, 1H), 7.26-7.33 (m, 2H), 7.40-7.52 (m, 2H), 7.66 (s, 1H), 7.78 (s, 1H), 8.08 (d, J=8.4 Hz, 2H), 8.35 (d, J=8.4 Hz, 2H), 10.58 (s, 1H).

Step 3: N-(2'-Fluoro-5-methylbiphenyl-3-yl)-N-methyl-4-nitrobenzamide

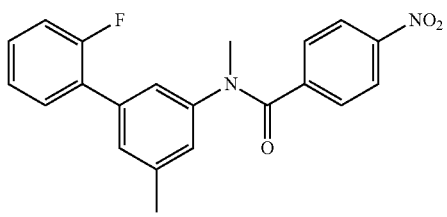 [SMILES: Cc1cc(-c2ccccc2F)cc(N(C)C(=O)c2ccc([N+](=O)[O-])cc2)c1]

The titled compound was prepared by the reaction of Step 2 intermediate (500 mg, 1.42 mmol) with methyl iodide (133 μL, 2.14 mmol) using sodium hydride (60% w/w, 85 mg, 2.14 mmol) in anhydrous DMF (10 mL) as per the procedure described in step 2 of Intermediate 1 to yield 430 mg of the product. The product obtained was used as such without characterization.

Step 4: 4-Amino-N-(2'-fluoro-5-methylbiphenyl-3-yl)-N-methylbenzamide

The titled compound was prepared by the reduction of Step 3 intermediate (405 mg, 1.11 mmol) using iron powder (310 mg, 5.55 mmol) and ammonium chloride (588 mg, 11.00 mmol) in a mixture of ethanol and water (2:1, 15 mL) as per the procedure described in step 3 of Intermediate 1 to obtain 305 mg of the product. ¹H NMR (300 MHz, DMSO-d₆) δ 2.28 (s, 3H), 3.34 (s, 3H), 5.45 (s, 2H), 6.32 (d, J=8.4 Hz, 2H), 7.01 (d, J=7.8 Hz, 4H), 7.14 (s, 1H), 7.23-7.40 (m, 4H); ESI-MS (m/z) 337 (M+H)⁺.

Intermediate 10

4-Amino-N-(3-chlorophenyl)-N-(2,2,2-trifluoroethyl)benzamide

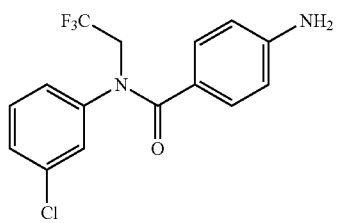 [SMILES: Nc1ccc(C(=O)N(CC(F)(F)F)c2cccc(Cl)c2)cc1]

Step 1: N-(3-Chlorophenyl)-2,2,2-trifluoroacetamide

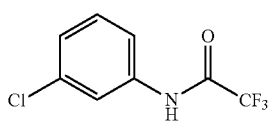 [SMILES: O=C(Nc1cccc(Cl)c1)C(F)(F)F]

To a cooled (−78° C.), stirred solution of 3-chloroaniline (2.0 g, 15.68 mmol) and triethylamine (2.2 mL, 15.68 mmol) in dichloromethane (40 mL) was added trifluoroacetic anhydride (2.2 mL, 15.68 mmol). The mixture was warmed to RT and stirred for 1 h. The mixture was diluted with dichloromethane (200 mL) and washed with water (100 mL) followed by brine (100 mL). The organic layer was dried over anhydrous sodium sulfate, filtered and concentrated under reduced pressure. The residue obtained was purified by silica gel column chromatography to yield 2.29 g of the titled product. ¹H NMR (300 MHz, DMSO-d₆) δ 7.30 (d, J=7.8 Hz, 1H), 7.44 (t, J=8.4 Hz, 1H), 7.62 (t, J=7.8 Hz, 1H), 7.80 (s, 1H), 11.43 (s, 1H).

Step 2: 3-Chloro-N-(2,2,2-trifluoroethyl)aniline

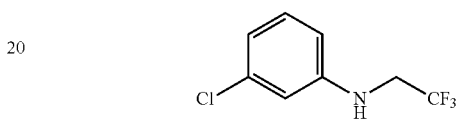

To a stirred solution of Step 1 intermediate (2.2 g, 9.84 mmol) in THF (75 mL) at 0° C. was added borane dimethylsulfide complex (2.05 mL, 21.65 mmol). The reaction mixture was allowed to attain RT and then heated to reflux for 2 h. The mixture was cooled to 0° C., quenched with methanol (5 mL) and stirred at RT for 30 min. The reaction mixture was poured into water (20 mL) and extracted with ethyl acetate (50 mL×2). The combined organic layers were washed with brine (50 mL) and concentrated under reduced pressure to yield 1.7 g of the product. ¹H NMR (300 MHz, DMSO-d₆) δ 3.91-4.03 (m, 2H), 6.49-6.53 (m, 1H), 6.61-6.69 (m, 2H), 6.77 (s, 1H), 7.10 (t, J=7.8 Hz, 1H).

Step 3: N-(3-Chlorophenyl)-4-nitro-N-(2,2,2-trifluoroethyl)benzamide

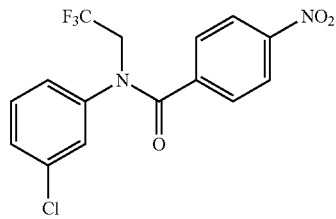 [SMILES: O=C(c1ccc([N+](=O)[O-])cc1)N(CC(F)(F)F)c1cccc(Cl)c1]

The titled compound was prepared by the reaction of Step 2 intermediate (1.8 g, 8.58 mmol) with 4-nitrobenzoyl chloride (1.6 g, 8.58 mmol) using triethylamine (3.6 mL, 25.76 mmol) in dichloromethane (30 mL) as per the procedure described in Step 1 of Intermediate 1 to yield 1.8 g of the product. ¹H NMR (300 MHz, DMSO-d₆) δ 4.78 (q, J=9.3 Hz, 2H), 7.14-7.17 (m, 1H), 7.26 (d, J=6.6 Hz, 2H), 7.53 (s, 1H), 7.56 (d, J=9.0 Hz, 2H), 8.08 (d, J=8.7 Hz, 2H).

Step 4: 4-Amino-N-(3-chlorophenyl)-N-(2,2,2-trifluoroethyl)benzamide

The titled compound was prepared by the reduction of Step 3 intermediate (1.8 g, 5.24 mmol) using iron powder (880 mg, 15.74 mmol) and ammonium chloride (2.8 g, 52.49 mmol) in a mixture of ethanol and water (5:1, 60 mL) as per the procedure described in step 3 of Intermediate 1 to obtain 1.43 g of the product. $^{1}$H NMR (300 MHz, DMSO-d$_{6}$) δ 4.68 (q, J=9.3 Hz, 2H), 5.62 (s, 2H), 6.32 (d, J=8.7 Hz, 2H), 6.97 (d, J=8.4 Hz, 2H), 7.07 (s, 1H), 7.26-7.32 (m, 3H).

Intermediate 11

(R)-4-Amino-N-(1-(4-chlorophenyl)ethyl)-N-methylbenzamide

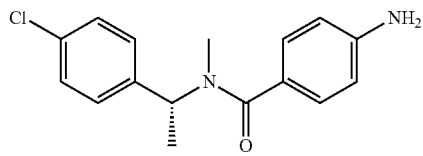 [SMILES: C[C@H](c1ccc(Cl)cc1)N(C)C(=O)c1ccc(N)cc1]

Step 1: (R)—N-(1-(4-Chlorophenyl)ethyl)-4-nitrobenzamide

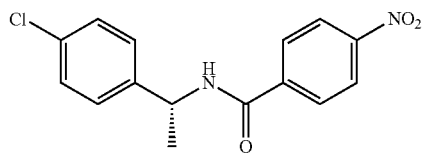 [SMILES: C[C@@H](NC(=O)c1ccc([N+](=O)[O-])cc1)c1ccc(Cl)cc1]

The titled compound was prepared by the reaction of (R)-(+)-α-methylbenzylamine (507 mg, 3.25 mmol) with 4-nitrobenzoyl chloride (725 mg, 3.90 mmol) using triethylamine (988 mg, 9.77 mmol) and DMAP (39 mg, 0.32 mmol) in dichloromethane (5.0 mL) as per the procedure described in Step 1 of Intermediate 1 to yield 603 mg of the product. $^{1}$H NMR (300 MHz, CDCl$_{3}$) δ 1.60 (d, J=7.5 Hz, 3H), 5.27 (t, J=8.7 Hz, 1H), 6.56 (s, 1H), 7.25-7.32 (m, 4H), 7.91 (d, J=8.1 Hz, 2H), 8.24 (d, J=8.7 Hz, 2H); ESI-MS (m/z) 290 (M+H)$^{+}$.

Step 2: (R)—N-(1-(4-Chlorophenyl)ethyl)-N-methyl-4-nitrobenzamide

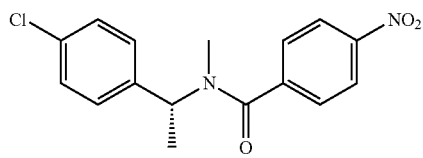 [SMILES: C[C@H](c1ccc(Cl)cc1)N(C)C(=O)c1ccc([N+](=O)[O-])cc1]

The titled compound was prepared by the reaction of Step 1 intermediate (253 mg, 0.83 mmol) with methyl iodide (176 mg, 1.24 mmol) using sodium hydride (60% w/w, 43 mg, 1.07 mmol) in anhydrous DMF (5.0 mL) as per the procedure described in step 2 of Intermediate 1 to yield 231 mg of the product. $^{1}$H NMR (300 MHz, DMSO-d$_{6}$) δ 1.55 (s, 3H), 2.70 (s, 3H), 4.73, 5.87 (br s, 1H, rotamer), 7.29 (s, 1H), 7.43 (s, 3H), 7.73 (d, J=7.2 Hz, 2H), 8.29 (d, J=7.2 Hz, 2H); ESI-MS (m/z) 317 (M−H)$^{+}$.

Step 3: (R)-4-Amino-N-(1-(4-chlorophenyl)ethyl)-N-methylbenzamide

The titled compound was prepared by the reduction of Step 2 intermediate (201 mg, 0.63 mmol) using iron powder (106 mg, 1.90 mmol) and ammonium chloride (339 mg, 6.33 mmol) in a mixture of ethanol and water (3:1, 10 mL) as per the procedure described in step 3 of Intermediate 1 to obtain 131 mg of the product. $^{1}$H NMR (300 MHz, DMSO-d$_{6}$) δ 1.54 (d, J=7.5 Hz, 3H), 2.61 (s, 3H), 5.50 (s, 3H), 6.54 (d, J=8.7 Hz, 2H), 7.15 (d, J=8.1 Hz, 2H), 7.29 (d, J=7.8 Hz, 2H), 7.43 (d, J=8.4 Hz, 2H); ESI-MS (m/z) 289 (M+H)$^{+}$.

Intermediate 12

(S)-4-Amino-N-(1-(4-chlorophenyl)ethyl)-N-methylbenzamide

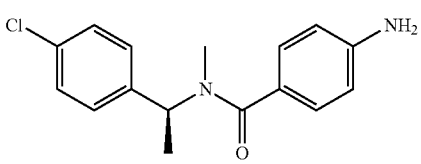 [SMILES: C[C@@H](c1ccc(Cl)cc1)N(C)C(=O)c1ccc(N)cc1]

Step 1: (S)—N-(1-(4-Chlorophenyl)ethyl)-4-nitrobenzamide

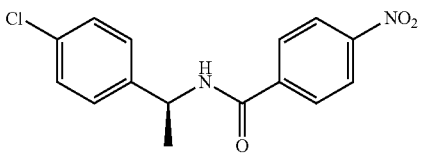 [SMILES: C[C@H](NC(=O)c1ccc([N+](=O)[O-])cc1)c1ccc(Cl)cc1]

The titled compound was prepared by the reaction of (S)-4-chloro-α-methylbenzylamine (503 mg, 3.23 mmol) with 4-nitrobenzoyl chloride (599 mg, 3.23 mmol) using triethylamine (1.3 mL, 9.69 mmol) and DMAP (39 mg, 0.32 mmol) in dichloromethane (10 mL) as per the procedure described in Step 1 of Intermediate 1 to yield 511 mg of the product. $^{1}$H NMR (300 MHz, DMSO-d$_{6}$) δ 1.47 (d, J=7.2 Hz, 3H), 5.12-5.19 (m, 1H), 7.38-7.42 (m, 4H), 8.10 (d, J=8.1 Hz, 2H), 8.31 (d, J=8.1 Hz, 2H), 9.18 (d, J=7.8 Hz, 1H); APCI-MS (m/z) 305 (M+H)$^{+}$.

Step 2: (S)—N-(1-(4-Chlorophenyl)ethyl)-N-methyl-4-nitrobenzamide

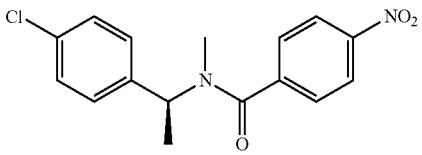 [SMILES: C[C@@H](c1ccc(Cl)cc1)N(C)C(=O)c1ccc([N+](=O)[O-])cc1]

The titled compound was prepared by the reaction of Step 1 intermediate (253 mg, 0.83 mmol) with methyl iodide (176 mg, 1.24 mmol) using sodium hydride (60% w/w, 43 mg, 1.07 mmol) in anhydrous DMF (5.0 mL) as per the procedure described in step 2 of Intermediate 1 to yield 214 mg of the product. $^{1}$H NMR (300 MHz, DMSO-d$_{6}$) δ 1.53 (d, J=7.2 Hz, 3H), 2.53 (s, 3H), 5.81-5.85 (m, 1H), 7.25-7.30 (m, 1H), 7.38-7.43 (m, 3H), 7.71 (d, J=7.8 Hz, 2H), 8.26 (d, J=8.4 Hz, 2H); APCI-MS (m/z) 319 (M+H)$^{+}$.

Step 3: (S)-4-Amino-N-(1-(4-chlorophenyl)ethyl)-N-methylbenzamide

The titled compound was prepared by the reduction of Step 2 intermediate (201 mg, 0.63 mmol) using iron powder (106 mg, 1.90 mmol) and ammonium chloride (339 mg, 6.33 mmol) in a mixture of ethanol and water (3:1, 10 mL) as per the procedure described in step 3 of Intermediate 1 to obtain 131 mg of the product. $^1$H NMR (300 MHz, DMSO-$d_6$) δ 1.50 (d, J=6.6 Hz, 3H), 2.60 (s, 3H), 5.44-5.48 (m, 3H), 6.52 (d, J=8.4 Hz, 2H), 7.13 (d, J=8.4 Hz, 2H), 7.27 (d, J=8.1 Hz, 2H), 7.40 (d, J=8.4 Hz, 2H).

Intermediate 13

(R)-4-Amino-N-((4-chlorophenyl)(cyclopropyl)methyl)-N-methylbenzamide

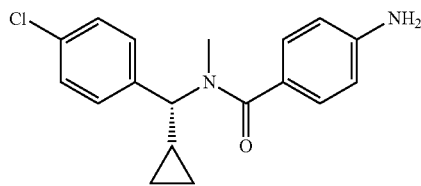 [SMILES: CN(C(=O)c1ccc(N)cc1)[C@@H](c1ccc(Cl)cc1)C1CC1]

Step 1: (4-Chlorophenyl)(cyclopropyl)methanone

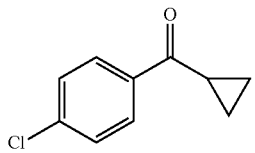 [SMILES: O=C(c1ccc(Cl)cc1)C1CC1]

To a stirred solution of cyclopropylcarbonitrile (607 mg, 9.04 mmol) in anhydrous diethyl ether (25 mL) was slowly added 4-chlorophenylmagnessium bromide (1M, 11 mL, 11.76 mmol) at 0° C. The reaction mixture was gradually warmed up to RT in duration of 2 h and continued to stir for another 6 h at RT. To that mixture were added 1N HCl (11 mL) and THF (11 mL) and continued to stir overnight at RT. The reaction mixture was cooled to 0° C. and quenched with saturated aqueous solution of ammonium chloride (50 mL) and ethyl acetate (50 mL). The layers were separated and the aqueous layer was extracted with ethyl acetate (50 mL×2). The combined organic layers were washed with brine (50 mL) and concentrated under reduced pressure. The residue obtained was purified by silica gel column chromatography to yield 705 mg of the titled product. $^1$H NMR (300 MHz, CDCl$_3$) δ 1.03-1.09 (m, 2H), 1.22-1.28 (m, 2H), 2.57-2.67 (m, 1H), 7.45 (d, J=8.4 Hz, 2H), 7.95 (d, J=8.4 Hz, 2H).

Step 2: N—((R)-(4-Chlorophenyl)(cyclopropyl)methyl)-2-methylpropane-2-sulfinamide

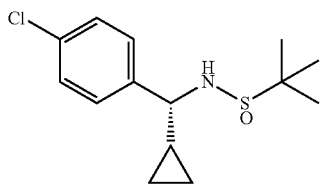

To a stirred solution of Step 1 intermediate (705 mg, 3.90 mmol) in THF (10 mL) were added titanium (VI) isopropoxide (1.7 mL, 8.19 mmol) and (R)-(+)-2-methyl-2-propanesulfinamide (520 mg, 4.29 mmol) at RT under inert atmosphere. The reaction mixture was stirred at 70° C. for 18 h. The mixture was cooled to 0° C. and added sodium borohydride (474 mg, 12.4 mmol) and stirred at RT for 3 h. The reaction was quenched with methanol (20 mL) at 0° C. The precipitated solid was filtered off and washed with ethyl acetate (50 mL×2). The combined filtrates were washed with water (40 mL), dried over anhydrous sodium sulfate, filtered and concentrated. The residue obtained was purified by silica gel column chromatography to afford 459 mg of the titled compound. $^1$H NMR (300 MHz, CDCl$_3$) δ 0.16-0.24 (m, 1H), 0.33-0.39 (m, 1H), 0.43-0.53 (m, 1H), 0.55-0.67 (m, 1H), 0.68-0.77 (m, 1H), 3.55-5.28 (m, 1H, NH, rotamer), 7.27-7.31 (m, 4H)), 7.32 (d, J=8.7 Hz, 2H), 7.41 (d, J=8.7 Hz, 2H); ESI-MS (m/z) 286 (M+H)$^+$.

Step 3: ((R)-(4-Chlorophenyl)(cyclopropyl)methanamine hydrochloride

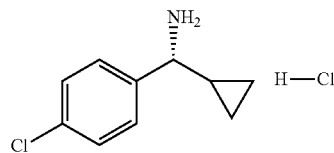

To an ice cold solution of Step 2 intermediate (454 mg, 1.58 mmol) in diethyl ether (10 mL) was added 4 M HCl in 1,4-dioxane (4.0 mL, 15.9 mmol) at RT. The resulting mixture was stirred at 0° C. for 1 h. The solvent was evaporated under reduced pressure and the residue thus obtained was dried under high vacuum to yield 340 mg of the titled compound. $^1$H NMR (300 MHz, DMSO-$d_6$) δ 0.34-0.37 (m, 1H), 0.45-0.50 (m, 1H), 0.59-0.65 (m, 2H), 1.27-1.31 (m, 1H), 3.59 (br s, 1H), 7.48 (d, J=8.4 Hz, 2H), 7.60 (d, J=8.4 Hz, 2H).

Step 4: (R)—N-((4-Chlorophenyl)(cyclopropyl)methyl)-4-nitrobenzamide

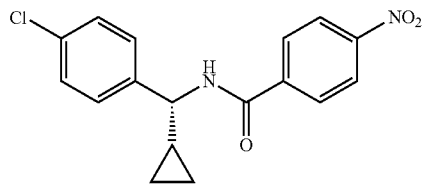 [SMILES: O=C(N[C@@H](c1ccc(Cl)cc1)C1CC1)c1ccc([N+](=O)[O-])cc1]

The titled compound was prepared by the reaction of Step 3 intermediate (327 mg, 1.49 mmol) with 4-nitrobenzoyl-chloride (305 mg, 1.64 mmol) in the presence triethylamine (625 μL, 4.49 mmol) in dichloromethane (10 mL) as per the procedure described in step 1 of Intermediate 1 to yield 315 mg of the product. $^1$H NMR (300 MHz, DMSO-$d_6$) δ 0.42-0.45 (m, 2H), 0.53-0.59 (m, 2H), 1.27-1.34 (m, 1H), 4.35 (t, J=8.7 Hz, 1H), 7.40 (d, J=8.1 Hz, 2H), 7.48 (d, J=7.5 Hz, 2H), 8.11 (d, J=8.7 Hz, 2H), 8.32 (d, J=8.7 Hz, 2H), 9.38 (d, J=7.8 Hz, 1H); ESI-MS (m/z) 331 (M+H)$^+$.

Step 5: (R)—N-((4-Chlorophenyl)(cyclopropyl)methyl)-N-methyl-4-nitrobenzamide

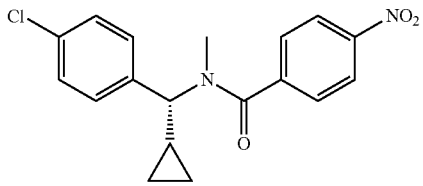 [SMILES: CN(C(=O)c1ccc([N+](=O)[O-])cc1)[C@@H](c1ccc(Cl)cc1)C1CC1]

The titled compound was prepared by the reaction of Step 4 intermediate (307 mg, 0.92 mmol) with methyl iodide (87 μL, 1.37 mmol) using sodium hydride (60% w/w, 48 mg, 2.02 mmol) in anhydrous DMF (10 mL) as per the procedure described in step 2 of Intermediate 1 to yield 283 mg of the desired product. ESI-MS (m/z) 344 (M)$^+$.

Step 6: (R)-4-Amino-N-((4-chlorophenyl)(cyclopropyl)methyl)-N-methylbenzamide

The titled compound was prepared by the reduction of Step 5 intermediate (273 mg, 0.79 mmol) using iron powder (132 mg, 2.37 mmol) and ammonium chloride (423 mg, 7.91 mmol) in a mixture of ethanol and water (2:1, 12 mL) as per the procedure described in step 3 of Intermediate 1 to obtain 174 mg of the product. $^1$H NMR (300 MHz, DMSO-d$_6$) δ 0.39 (br s, 1H), 0.57 (br s, 2H), 0.79 (br s, 2H), 1.28-1.41 (m, 1H), 2.77 (s, 3H), 5.47 (s, 2H), 6.50 (d, J=7.8 Hz, 2H), 7.10 (d, J=7.2 Hz, 2H), 7.44 (s, 4H); ESI-MS (m/z) 315 (M+H)$^+$.

Intermediate 14

4-Amino-N-(3,5-dichlorophenyl)-N-methylbenzamide

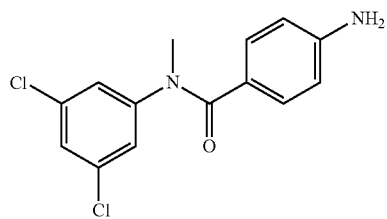

Step 1: N-(3,5-Dichlorophenyl)-4-nitrobenzamide

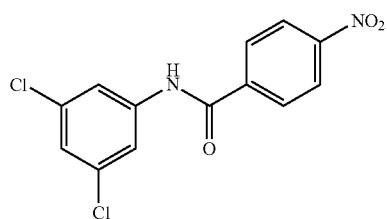 [SMILES: O=C(Nc1cc(Cl)cc(Cl)c1)c1ccc([N+](=O)[O-])cc1]

The titled compound was prepared by the reaction of 3,5-dichloroaniline (2.0 g, 12.42 mmol) with 4-nitrobenzoylchloride (2.42 g, 13.04 mmol) in the presence of triethylamine (5.2 mL, 37.26 mmol) in dichloromethane (20 mL) as per the procedure described in Step 1 of Intermediate 1 to yield 2.59 g of the product. $^1$H NMR (300 MHz, DMSO-d$_6$) δ 7.37 (s, 1H), 7.89 (s, 2H), 8.17 (d, J=8.7 Hz, 2H), 8.38 (d, J=8.7 Hz, 2H), 10.82 (s, 1H).

Step 2: N-(3,5-Dichlorophenyl)-N-methyl-4-nitrobenzamide

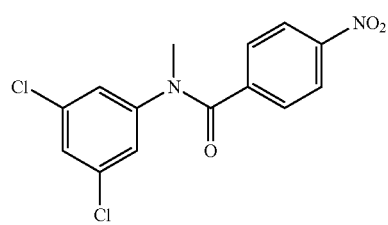 [SMILES: CN(C(=O)c1ccc([N+](=O)[O-])cc1)c1cc(Cl)cc(Cl)c1]

The titled compound was prepared by the reaction of Step 1 intermediate (2.51 g, 8.06 mmol) with methyl iodide (656 μL, 10.48 mmol) using sodium hydride (60% w/w, 388 mg, 9.68 mmol) in anhydrous DMF (25 mL) as per the procedure described in Step 2 of Intermediate 1 to yield 2.38 g of the product. $^1$H NMR (300 MHz, DMSO-d$_6$) δ 3.34 (s, 3H), 7.45 (s, 3H), 7.60 (d, J=8.7 Hz, 2H), 8.16 (d, J=8.4 Hz, 2H).

Step 3: 4-Amino-N-(3,5-dichlorophenyl)-N-methylbenzamide

The titled compound was prepared by the reduction of Step 2 intermediate (2.3 g, 7.07 mmol) using iron powder (1.18 g, 21.21 mmol) and ammonium chloride (3.77 g, 70.73 mmol) in a mixture of ethanol and water (5:1, 60 mL) as per the procedure described in Step 3 of Intermediate 1 to obtain 1.75 g of the product. $^1$H NMR (300 MHz, DMSO-d$_6$) δ 3.29 (s, 3H), 5.55 (s, 2H), 6.35 (d, J=8.4 Hz, 2H), 6.98 (d, J=8.4 Hz, 2H), 7.20 (s, 2H), 7.34 (s, 1H).

Intermediate 15

4-Amino-N-(3-chloro-5-fluorophenyl)-N-methylbenzamide

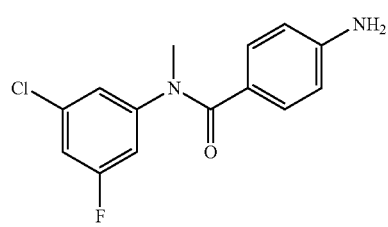

Step 1: N-(3-Chloro-5-fluorophenyl)-4-nitrobenzamide

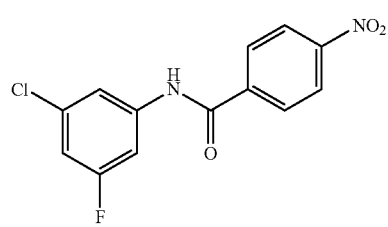 [SMILES: O=C(Nc1cc(F)cc(Cl)c1)c1ccc([N+](=O)[O-])cc1]

The titled compound was prepared by the reaction of 3-chloro-5-fluoroaniline (1.0 g, 6.86 mmol) with 4-nitrobenzoylchloride (1.27 g, 6.86 mmol) in the presence of triethylamine (1.9 mL, 13.73 mmol) in dichloromethane (20 mL) as per the procedure described in Step 1 of Intermediate 1 to yield 933 mg of the product. $^1$H NMR (300 MHz, DMSO-$d_6$) δ 7.21 (d, J=8.1 Hz, 1H), 7.65-7.76 (m, 2H), 8.17 (d, J=9.0 Hz, 2H), 8.40 (d, J=9.0 Hz, 2H), 10.86 (s, 1H).

Step 2: N-(3-Chloro-5-fluorophenyl)-N-methyl-4-nitrobenzamide

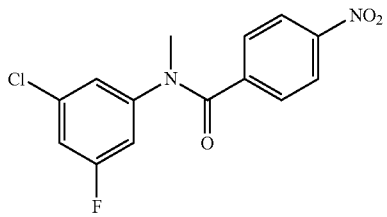 [SMILES: CN(C(=O)c1ccc([N+](=O)[O-])cc1)c1cc(F)cc(Cl)c1]

The titled compound was prepared by the reaction of Step 1 intermediate (924 mg, 3.13 mmol) with methyl iodide (238 μL, 3.76 mmol) using sodium hydride (60% w/w, 150 mg, 3.76 mmol) in anhydrous DMF (10 mL) as per the procedure described in Step 2 of Intermediate 1 to yield 1.04 g of the product. $^1$H NMR (300 MHz, DMSO-$d_6$) δ 3.33 (s, 3H), 7.24-7.35 (m, 3H), 7.60 (d, J=8.4 Hz, 2H), 8.16 (d, J=8.4 Hz, 2H).

Step 3: 4-Amino-N-(3-chloro-5-fluorophenyl)-N-methylbenzamide

The titled compound was prepared by the reduction of Step 2 intermediate (1.03 g, 3.33 mmol) using iron powder (559 mg, 10.00 mmol) and ammonium chloride (1.78 g, 33.36 mmol) in a mixture of ethanol and water (5:1, 30 mL) as per the procedure described in Step 3 of Intermediate 1 to yield 732 mg of the product. $^1$H NMR (300 MHz, DMSO-$d_6$) δ 3.31 (s, 3H), 5.57 (s, 2H), 6.37 (d, J=8.4 Hz, 2H), 6.98-7.10 (m, 4H), 7.20 (d, J=8.1 Hz, 1H).

Intermediate 16

4-Amino-N-(2-chloro-4-methylphenyl)-N-methylbenzamide

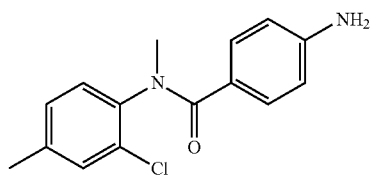

Step 1: N-(2-Chloro-4-methylphenyl)-4-nitrobenzamide

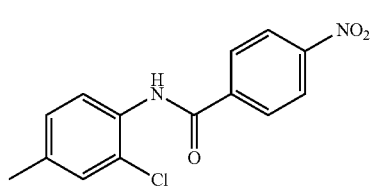

The titled compound was prepared by the reaction of 2-chloro-4-methylaniline (1.0 g, 7.06 mmol) with 4-nitrobenzoylchloride (1.3 g, 7.06 mmol) in the presence of triethylamine (3.0 mL, 21.18 mmol) in dichloromethane (20 mL) as per the procedure described in Step 1 of Intermediate 1 to yield 2.03 g of the product. $^1$H NMR (300 MHz, DMSO-$d_6$) δ 2.33 (s, 3H), 7.20 (d, J=7.8 Hz, 1H), 7.39-7.45 (m, 2H), 8.20 (d, J=8.1 Hz, 2H), 8.36 (d, J=9.0 Hz, 2H), 10.43 (s, 1H).

Step 2: N-(2-Chloro-4-methylphenyl)-N-methyl-4-nitrobenzamide

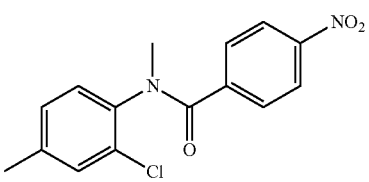 [SMILES: Cc1ccc(N(C)C(=O)c2ccc(N)cc2)c(Cl)c1]

The titled compound was prepared by the reaction of Step 1 intermediate (2.0 g, 6.87 mmol) with methyl iodide (516 μL, 8.25 mmol) using sodium hydride (60% w/w, 330 mg, 8.25 mmol) in anhydrous DMF (20 mL) as per the procedure described in Step 2 of Intermediate 1 to yield 2.04 g of the product. $^1$H NMR (300 MHz, DMSO-$d_6$) δ 2.21 (s, 3H), 3.26 (s, 3H), 7.11 (d, J=8.1 Hz, 1H), 7.27 (s, 1H), 7.44 (d, J=7.8 Hz, 1H), 7.54 (d, J=8.7 Hz, 2H), 8.07 (d, J=8.4 Hz, 2H).

Step 3: 4-Amino-N-(2-chloro-4-methylphenyl)-N-methylbenzamide

The titled compound was prepared by the reduction of Step 2 intermediate (2.01 g, 6.59 mmol) using iron powder (1.1 g, 19.78 mmol) and ammonium chloride (3.52 g, 65.96 mmol) in a mixture of ethanol and water (5:1, 30 mL) as per the procedure described in Step 3 of Intermediate 1 to obtain 1.63 g of the product. $^1$H NMR (300 MHz, DMSO-$d_6$) δ 2.23 (s, 3H), 3.13 (s, 3H), 5.42 (s, 2H), 6.26 (d, J=7.8 Hz, 2H), 6.94 (d, J=7.8 Hz, 2H), 7.06 (d, J=8.4 Hz, 1H), 7.18 (d, J=7.8 Hz, 1H), 7.26 (s, 1H).

Intermediate 17

4-Amino-N-(4-chloro-2-methylphenyl)-N-methylbenzamide

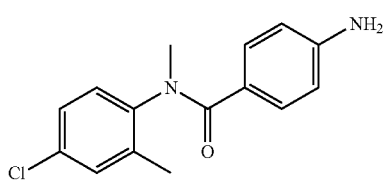 [SMILES: Cc1cc(Cl)ccc1N(C)C(=O)c1ccc(N)cc1]

Step 1: N-(4-Chloro-2-methylphenyl)-4-nitrobenzamide

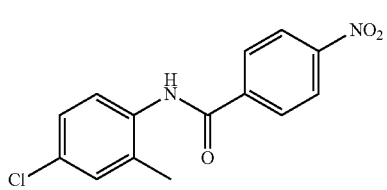 [SMILES: Cc1cc(Cl)ccc1NC(=O)c1ccc([N+](=O)[O-])cc1]

The titled compound was prepared by the reaction of 4-chloro-2-methylaniline (1.0 g, 7.06 mmol) with 4-nitrobenzoylchloride (1.3 g, 7.06 mmol) in a mixture of pyridine and dichloromethane (1:1, 20 mL) as per the procedure described in Step 1 of Intermediate 1 to yield 2.03 g of the product. ¹H NMR (300 MHz, DMSO-d₆) δ 2.22 (s, 3H), 7.28 (d, J=8.4 Hz, 1H), 7.38 (d, J=6.6 Hz, 2H), 8.17 (d, J=8.7 Hz, 2H), 8.35 (d, J=8.7 Hz, 2H), 10.24 (s, 1H).

Step 2: N-(4-Chloro-2-methylphenyl)-N-methyl-4-nitrobenzamide

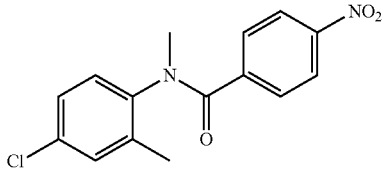 [SMILES: Cc1cc(Cl)ccc1N(C)C(=O)c1ccc([N+](=O)[O-])cc1]

The titled compound was prepared by the reaction of Step intermediate (2.0 g, 6.87 mmol) with methyl iodide (560 μL, 8.94 mmol) using sodium hydride (60% w/w, 357 mg, 8.94 mmol) in anhydrous DMF (20 mL) as per the procedure described in Step 2 of Intermediate 1 to yield 2.1 g of the product. ¹H NMR (300 MHz, DMSO-d₆) δ 2.18 (s, 3H), 3.26 (s, 3H), 7.17 (d, J=8.1 Hz, 1H), 7.31 (d, J=8.7 Hz, 2H), 7.50 (d, J=8.4 Hz, 2H), 8.06 (d, J=8.7 Hz, 2H).

Step 3: 4-Amino-N-(4-chloro-2-methylphenyl)-N-methylbenzamide

The titled compound was prepared by the reduction of Step 2 intermediate (2.1 g, 6.89 mmol) using iron powder (1.15 g, 20.63 mmol) and ammonium chloride (3.68 g, 68.91 mmol) in a mixture of ethanol and water (5:1, 30 mL) as per the procedure described in Step 3 of Intermediate 1 to obtain 1.7 g of the product. ¹H NMR (300 MHz, DMSO-d₆): δ 2.08 (s, 3H), 3.15 (s, 3H), 5.46 (s, 2H), 6.28-6.33 (m, 2H), 6.89-6.94 (m, 2H), 7.15-7.20 (m, 2H), 7.28 (s, 1H).

Intermediate 18

4-Amino-N-(2,4-dichlorophenyl)-N-methylbenzamide

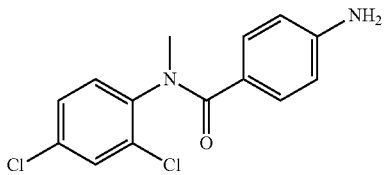 [SMILES: CN(C(=O)c1ccc(N)cc1)c1ccc(Cl)cc1Cl]

Step 1: N-(2,4-Dichlorophenyl)-4-nitrobenzamide

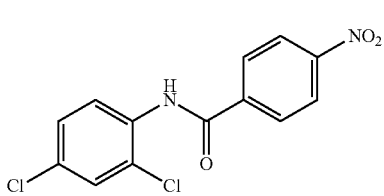 [SMILES: O=C(Nc1ccc(Cl)cc1Cl)c1ccc([N+](=O)[O-])cc1]

The titled compound was prepared by the reaction of 2,4-dichloroaniline (2.0 g, 12.42 mmol) with 4-nitrobenzoylchloride (2.4 g, 13.04 mmol) in a mixture of pyridine and dichloromethane (1:1, 20 mL) as per the procedure described in Step 1 of Intermediate 1 to yield 2.9 g of the product. ¹H NMR (300 MHz, DMSO-d₆) δ 7.50 (d, J=8.1 Hz, 1H), 7.63 (d, J=8.7 Hz, 1H), 7.76 (s, 1H), 8.20 (d, J=8.4 Hz, 2H), 8.38 (d, J=8.7 Hz, 2H), 10.51 (s, 1H).

Step 2:
N-(2,4-Dichlorophenyl)-N-methyl-4-nitrobenzamide

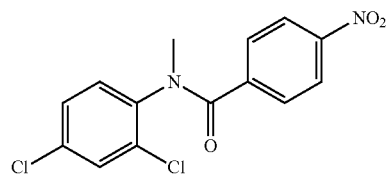 [SMILES: CN(C(=O)c1ccc([N+](=O)[O-])cc1)c1ccc(Cl)cc1Cl]

The titled compound was prepared by the reaction of Step 1 intermediate (2.5 g, 8.03 mmol) with methyl iodide (605 μL, 9.64 mmol) using sodium hydride (60% w/w, 386 mg, 9.64 mmol) in anhydrous DMF (20 mL) as per the procedure described in Step 2 of Intermediate 1 to yield 2.4 g of the product. ¹H NMR (300 MHz, DMSO-d₆) δ 3.28 (s, 3H), 7.41 (d, J=8.4 Hz, 1H), 7.53 (d, J=8.1 Hz, 2H), 7.64 (d, J=7.5 Hz, 2H), 8.10 (d, J=9.0 Hz, 2H).

Step 3:
4-Amino-N-(2,4-dichlorophenyl)-N-methylbenzamide

The titled compound was prepared by the reduction of Step 2 intermediate (2.4 g, 7.65 mmol) using iron powder (1.3 g, 22.95 mmol) and ammonium chloride (4.03 g, 76.51 mmol) in a mixture of ethanol and water (5:1, 30 mL) as per the procedure described in Step 3 of Intermediate 1 to obtain 1.9 g of the product. ¹H NMR (300 MHz, DMSO-d₆) δ 3.17 (s, 3H), 5.50 (s, 2H), 6.31 (d, J=7.8 Hz, 2H), 6.96 (d, J=7.5 Hz, 2H), 7.39 (s, 2H), 7.65 (s, 1H).

Intermediate 19

4-Amino-N-(3-chloro-2-fluorophenyl)-N-methylbenzamide

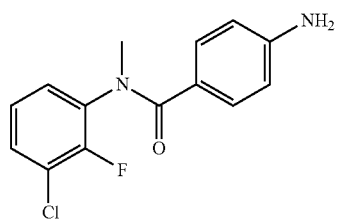

Step 1:
N-(3-Chloro-2-fluorophenyl)-4-nitrobenzamide

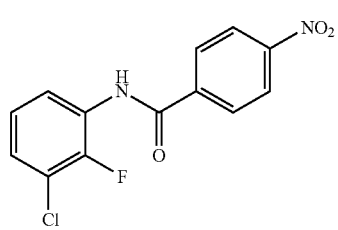 [SMILES: O=C(Nc1cccc(Cl)c1F)c1ccc([N+](=O)[O-])cc1]

The titled compound was prepared by the reaction of 3-chloro-2-fluoroaniline (2.0 g, 13.73 mmol) with 4-nitrobenzoylchloride (2.54 g, 13.73 mmol) in a mixture of pyridine and dichloromethane (1:1, 20 mL) as per the procedure described in Step 1 of Intermediate 1 to yield 2.1 g of the product. $^1$H NMR (300 MHz, DMSO-$d_6$) δ 8.01 (t, J=6.9 Hz, 2H), 8.21 (d, J=8.7 Hz, 2H), 8.38 (d, J=8.7 Hz, 2H), 8.50-8.54 (m, 1H), 10.73 (s, 1H); ESI-MS (m/z) 293 (M−H)$^-$.

Step 2: N-(3-Chloro-2-fluorophenyl)-N-methyl-4-nitrobenzamide

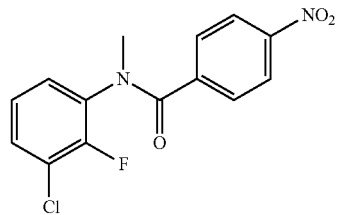 [SMILES: CN(C(=O)c1ccc([N+](=O)[O-])cc1)c1cccc(Cl)c1F]

The titled compound was prepared by the reaction of Step 1 intermediate (2.0 g, 4.78 mmol) with methyl iodide (523 μL, 8.14 mmol) using sodium hydride (60% w/w, 325 mg, 8.14 mmol) in anhydrous DMF (20 mL) as per the procedure described in Step 2 of Intermediate 1 to yield 1.4 g of the product. $^1$H NMR (300 MHz, DMSO-$d_6$): δ 3.32 (s, 3H), 7.16-7.21 (m, 1H), 7.45-7.53 (m, 4H), 8.10-8.16 (m, 2H).

Step 3: 4-Amino-N-(3-chloro-2-fluorophenyl)-N-methylbenzamide

The titled compound was prepared by the reduction of Step 2 intermediate (1.3 g, 4.21 mmol) using iron powder (705 mg, 12.63 mmol) and ammonium chloride (2.25 g, 42.11 mmol) in a mixture of ethanol and water (5:1, 60 mL) as per the procedure described in Step 3 of Intermediate 1 to obtain 890 mg of the product. $^1$H NMR (300 MHz, DMSO-$d_6$) δ 3.24 (s, 3H), 5.53 (s, 2H), 6.32 (d, J=8.4 Hz, 2H), 6.98 (d, J=8.4 Hz, 2H), 7.18 (t, J=8.4 Hz, 1H), 7.33-7.46 (m, 2H).

Intermediate 20

4-Amino-N-(2-chloro-5-methylphenyl)-N-methyl-benzamide

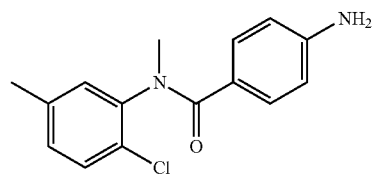 [SMILES: Cc1ccc(Cl)c(N(C)C(=O)c2ccc(N)cc2)c1]

Step 1:
N-(2-Chloro-5-methylphenyl)-4-nitrobenzamide

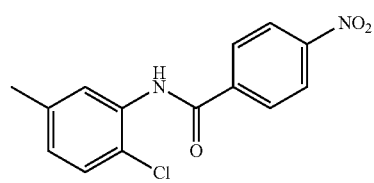 [SMILES: Cc1ccc(Cl)c(NC(=O)c2ccc([N+](=O)[O-])cc2)c1]

The titled compound was prepared by the reaction of 2-chloro-5-methylaniline (2.0 g, 14.12 mmol) with 4-nitrobenzoylchloride (2.62 g, 14.12 mmol) in a mixture of pyridine and dichloromethane (1:1, 20 mL) as per the procedure described in Step 1 of Intermediate 1 to yield 3.4 g of the product. $^1$H NMR (300 MHz, DMSO-$d_6$) δ 2.31 (s, 3H), 7.13 (d, J=7.2 Hz, 1H), 7.37-7.45 (m, 2H), 8.18 (d, J=8.7 Hz, 2H), 8.36 (d, J=8.7 Hz, 2H), 10.39 (s, 1H); APCI-MS (m/z) 289 (M−H)$^-$.

Step 2: N-(2-Chloro-5-methylphenyl)-N-methyl-4-nitrobenzamide

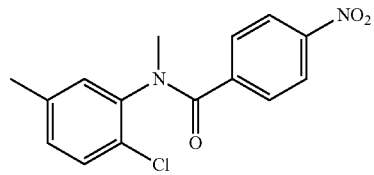

The titled compound was prepared by the reaction of Step 1 intermediate (2.0 g, 6.87 mmol) with methyl iodide (560 μL, 8.94 mmol) using sodium hydride (60% w/w, 358 mg, 8.94 mmol) in anhydrous DMF (20 mL) as per the procedure described in Step 2 of Intermediate 1 to yield 1.7 g of the product. $^1$H NMR (300 MHz, DMSO-$d_6$) δ 2.21 (s, 3H), 3.28 (s, 3H), 7.09 (d, J=7.8 Hz, 1H), 7.28 (d, J=7.8 Hz, 1H), 7.43 (s, 1H), 7.54 (d, J=8.4 Hz, 2H), 8.06 (d, J=9.0 Hz, 2H).

Step 3: 4-Amino-N-(2-chloro-5-methylphenyl)-N-methylbenzamide

The titled compound was prepared by the reduction of Step 2 intermediate (1.6 g, 5.25 mmol) using iron powder (880 mg, 15.75 mmol) and ammonium chloride (2.8 g, 52.50 mmol) in a mixture of ethanol and water (5:1, 60 mL) as per the procedure described in Step 3 of Intermediate 1 to obtain 1.2 g of the product. $^1$H NMR (300 MHz, DMSO-$d_6$) δ 2.22 (s, 3H), 3.16 (s, 3H), 5.46 (s, 2H), 6.28 (d, J=7.8 Hz, 2H), 6.98 (d, J=7.8 Hz, 3H), 7.18 (s, 1H), 7.32 (d, J=8.4 Hz, 1H).

Intermediate 21

4-Amino-N-(2-fluoro-5-methylphenyl)-N-methyl-benzamide

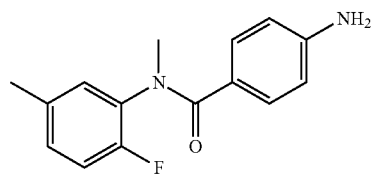

Step 1:
N-(2-Fluoro-5-methylphenyl)-4-nitrobenzamide

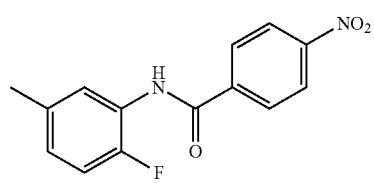 [SMILES: Cc1ccc(F)c(NC(=O)c2ccc([N+](=O)[O-])cc2)c1]

The titled compound was prepared by the reaction of 2-fluoro-5-methylaniline (1.0 g, 7.99 mmol) with 4-nitrobenzoylchloride (1.48 g, 7.99 mmol) in a mixture of pyridine and dichloromethane (1:1, 20 mL) as per the procedure described in Step 1 of Intermediate 1 to yield 1.7 g of the product. $^1$H NMR (300 MHz, DMSO-d$_6$) δ 2.30 (s, 3H), 7.08-7.24 (m, 2H), 7.42 (d, J=6.0 Hz, 1H), 8.18 (d, J=9.0 Hz, 2H), 8.36 (d, J=9.0 Hz, 2H), 10.42 (s, 1H).

Step 2: N-(2-Fluoro-5-methylphenyl)-N-methyl-4-nitrobenzamide

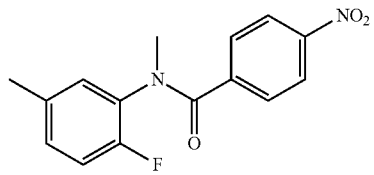 [SMILES: Cc1ccc(F)c(N(C)C(=O)c2ccc([N+](=O)[O-])cc2)c1]

The titled compound was prepared by the reaction of Step 1 intermediate (1.64 g, 6.00 mmol) with methyl iodide (457 µL, 7.20 mmol) using sodium hydride (60% w/w, 288 mg, 7.20 mmol) in anhydrous DMF (10 mL) as per the procedure described in Step 2 of Intermediate 1 to yield 1.8 g of the product. $^1$H NMR (300 MHz, DMSO-d$_6$) δ 2.21 (s, 3H), 3.33 (s, 3H), 7.01-7.09 (m, 2H), 7.34 (d, J=7.8 Hz, 1H), 7.54 (d, J=7.8 Hz, 2H), 8.10 (d, J=8.4 Hz, 2H).

Step 3: 4-Amino-N-(2-fluoro-5-methylphenyl)-N-methylbenzamide

The titled compound was prepared by the reduction of Step 2 intermediate (1.74 g, 6.03 mmol) using iron powder (1.01 g, 18.10 mmol) and ammonium chloride (3.22 g, 60.36 mmol) in a mixture of ethanol and water (5:1, 60 mL) as per the procedure described in Step 3 of Intermediate 1 to obtain 1.4 g of the product. $^1$H NMR (300 MHz, DMSO-d$_6$) δ 2.22 (s, 3H), 3.21 (s, 3H), 5.46 (s, 2H), 6.30 (d, J=8.1 Hz, 2H), 6.95-7.05 (m, 4H), 7.16 (d, J=7.8 Hz, 1H); APCI-MS (m/z) 260 (M+H)$^+$.

Intermediate 22

4-Amino-N-(2-chloro-6-methylphenyl)-N-methylbenzamide

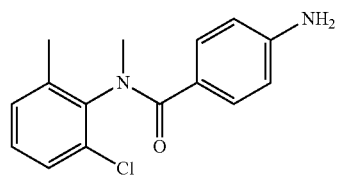

Step 1:
N-(2-Chloro-6-methylphenyl)-4-nitrobenzamide

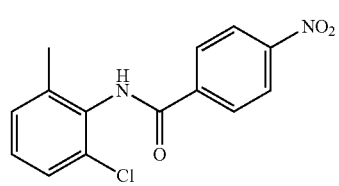 [SMILES: Cc1cccc(Cl)c1NC(=O)c1ccc([N+](=O)[O-])cc1]

The titled compound was prepared by the reaction of 2-chloro-6-methylaniline (502 mg, 3.54 mmol) with 4-nitrobenzoylchloride (657 mg, 3.54 mmol) in a mixture of pyridine and dichloromethane (1:2, 15 mL) as per the procedure described in Step 1 of Intermediate 1 to yield 751 mg of the product. $^1$H NMR (300 MHz, DMSO-d$_6$) δ 2.24 (s, 3H), 7.28-7.33 (m, 2H), 7.42 (d, J=6.0 Hz, 1H), 8.22 (d, J=8.7 Hz, 2H), 8.40 (d, J=8.7 Hz, 2H), 10.40 (s, 1H); APCI-MS (m/z) 291 (M+H)$^+$.

Step 2: N-(2-Chloro-6-methylphenyl)-N-methyl-4-nitrobenzamide

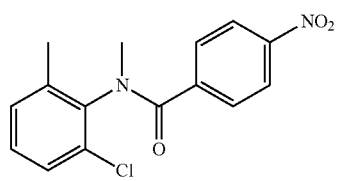 [SMILES: Cc1cccc(Cl)c1N(C)C(=O)c1ccc([N+](=O)[O-])cc1]

The titled compound was prepared by the reaction of Step 1 intermediate (742 mg, 2.55 mmol) with methyl iodide (191 µL, 3.06 mmol) using sodium hydride (60% w/w, 122 mg, 3.06 mmol) in anhydrous DMF (15 mL) as per the procedure described in Step 2 of Intermediate 1 to yield 620 mg of the product. $^1$H NMR (300 MHz, DMSO-d$_6$) δ 2.30 (s, 3H), 3.23 (s, 3H), 7.18-7.23 (m, 2H), 7.26-7.30 (m, 1H), 7.52 (d, J=9.0 Hz, 2H), 8.06 (d, J=8.7 Hz, 2H); APCI-MS (m/z) 305 (M+H)$^+$.

Step 3: 4-Amino-N-(2-chloro-6-methylphenyl)-N-methylbenzamide

The titled compound was prepared by the reduction of Step 2 intermediate (610 mg, 2.00 mmol) using iron powder (335 mg, 6.00 mmol) and ammonium chloride (1.06 g, 20.0 mmol) in a mixture of ethanol and water (5:1, 30 mL) as per the procedure described in Step 3 of Intermediate 1 to obtain 481 mg of the product. $^1$H NMR (300 MHz, DMSO-d$_6$) δ 2.14 (s, 3H), 3.10 (s, 3H), 5.46 (s, 2H), 6.26 (d, J=8.7 Hz, 2H), 6.93 (d, J=8.7 Hz, 2H), 7.18 (d, J=5.4 Hz, 2H), 7.30-7.34 (m, 1H); APCI-MS (m/z) 275 (M+H)$^+$.

Intermediate 23

4-Amino-N-mesityl-N-methylbenzamide

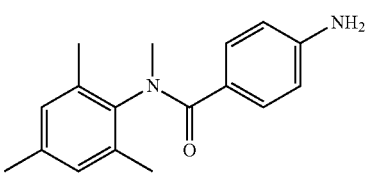

Step 1: N-Mesityl-4-nitrobenzamide

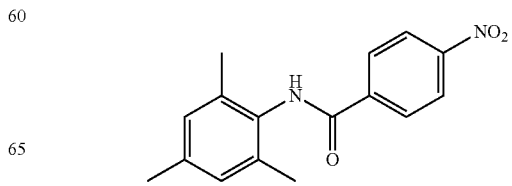

The titled compound was prepared by the reaction of 2,4,6-trimethylaniline (503 mg, 3.72 mmol) with 4-nitrobenzoylchloride (650 mg, 3.72 mmol) in a mixture of pyridine and dichloromethane (1:2, 15 mL) as per the procedure described in Step 1 of Intermediate 1 to yield 936 mg of the product. $^1$H NMR (300 MHz, DMSO-$d_6$) δ 2.14 (s, 6H), 2.25 (s, 3H), 6.94 (s, 2H), 8.20 (d, J=8.7 Hz, 2H), 8.37 (d, J=8.7 Hz, 2H), 10.02 (s, 1H); APCI-MS (m/z) 285 (M+H)$^+$.

Step 2: N-Mesityl-N-methyl-4-nitrobenzamide

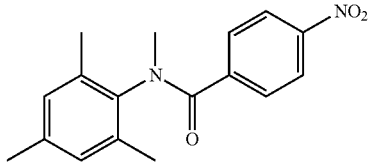 [SMILES: Cc1cc(C)c(N(C)C(=O)c2ccc([N+](=O)[O-])cc2)c(C)c1]

The titled compound was prepared by the reaction of Step 1 intermediate (923 mg, 3.25 mmol) with methyl iodide (245 μL, 3.90 mmol) using sodium hydride (60% w/w, 156 mg, 3.85 mmol) in anhydrous DMF (10 mL) as per the procedure described in Step 2 of Intermediate 1 to yield 899 mg of the product. $^1$H NMR (300 MHz, DMSO-$d_6$) δ 2.14 (s, 9H), 3.19 (s, 3H), 6.83 (s, 2H), 7.45 (d, J=8.4 Hz, 2H), 8.03 (d, J=8.1 Hz, 2H); APCI-MS (m/z) 299 (M+H)$^+$.

Step 3: 4-Amino-N-mesityl-N-methylbenzamide

The titled compound was prepared by the reduction of Step 2 intermediate (893 mg, 2.99 mmol) using iron powder (501 mg, 8.98 mmol) and ammonium chloride (1.6 g, 29.9 mmol) in a mixture of ethanol and water (5:1, 35 mL) as per the procedure described in Step 3 of Intermediate 1 to obtain 610 mg of the product. $^1$H NMR (300 MHz, DMSO-$d_6$) δ 2.06 (s, 6H), 2.18 (s, 3H), 3.06 (s, 3H), 5.40 (s, 2H), 6.24 (d, J=8.4 Hz, 2H), 6.84 (s, 2H), 6.89 (d, J=8.1 Hz, 2H).

Intermediate 24

4-Amino-N-(2-chloro-4,6-dimethylphenyl)-N-methylbenzamide

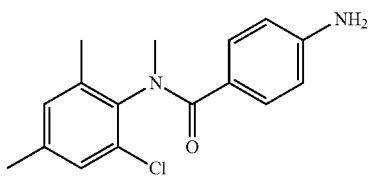 [SMILES: Cc1cc(C)c(N(C)C(=O)c2ccc(N)cc2)c(Cl)c1]

Step 1:
N-(2-Chloro-4,6-dimethylphenyl)-4-nitrobenzamide

The titled compound was prepared by the reaction of 2-chloro-4,6-dimethylaniline (1.0 g, 6.42 mmol) with 4-nitrobenzoylchloride (1.19 g, 6.42 mmol) in a mixture of pyridine and dichloromethane (1:2, 20 mL) as per the procedure described in Step 1 of Intermediate 1 to yield 1.1 g of the product. $^1$H NMR (300 MHz, DMSO-$d_6$) δ 2.19 (s, 3H), 2.31 (s, 3H), 7.12 (s, 1H), 7.25 (s, 1H), 8.21 (d, J=8.7 Hz, 2H), 8.38 (d, J=8.7 Hz, 2H), 10.29 (s, 1H); APCI-MS (m/z) 304 (M−H)$^-$.

Step 2: N-(2-Chloro-4,6-dimethylphenyl)-N-methyl-4-nitrobenzamide

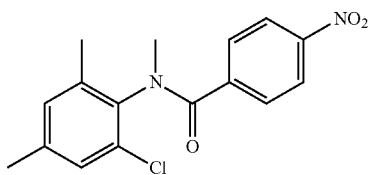 [SMILES: Cc1cc(C)c(N(C)C(=O)c2ccc([N+](=O)[O-])cc2)c(Cl)c1]

The titled compound was prepared by the reaction of Step 1 intermediate (1.00 g, 3.28 mmol) with methyl iodide (246 μL, 3.93 mmol) using sodium hydride (60% w/w, 158 mg, 3.93 mmol) in anhydrous DMF (15 mL) as per the procedure described in Step 2 of Intermediate 1 to yield 1.0 g of the product. $^1$H NMR (300 MHz, DMSO-$d_6$) δ 2.18 (s, 3H), 2.25 (s, 3H), 3.20 (s, 3H), 7.02 (s, 1H), 7.13 (s, 1H), 7.52 (d, J=8.4 Hz, 2H), 8.08 (d, J=8.7 Hz, 2H); APCI-MS (m/z) 319 (M+H)$^+$.

Step 3: 4-Amino-N-(2-chloro-4,6-dimethylphenyl)-N-methylbenzamide

The titled compound was prepared by the reduction of Step 2 intermediate (1.00 g, 3.13 mmol) using iron powder (525 mg, 9.39 mmol) and ammonium chloride (1.67 g, 31.37 mmol) in a mixture of ethanol and water (5:1, 60 mL) as per the procedure described in Step 3 of Intermediate 1 to obtain 731 mg of the product. $^1$H NMR (300 MHz, DMSO-$d_6$) δ 2.09 (s, 3H), 2.21 (s, 3H), 3.08 (s, 3H), 5.43 (s, 2H), 6.27 (d, J=8.7 Hz, 2H), 6.92-6.99 (m, 3H), 7.15 (s, 1H); APCI-MS (m/z) 289 (M+H)$^+$.

Intermediate 25

4-Amino-N-(2-cyclopropyl-4-methylphenyl)-N-methylbenzamide

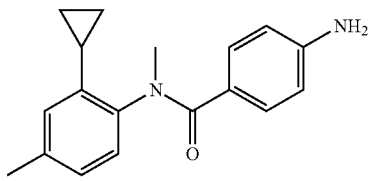

Step 1:
N-(2-Cyclopropyl-4-methylphenyl)-4-nitrobenzamide

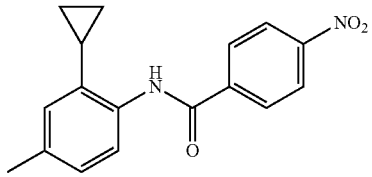 [SMILES: Cc1ccc(NC(=O)c2ccc([N+](=O)[O-])cc2)c(C2CC2)c1]

The titled compound was prepared by the reaction of 2-cyclopropyl-4-methylaniline (271 mg, 1.84 mmol) with 4-nitrobenzoylchloride (341 mg, 1.84 mmol) in a mixture of pyridine and dichloromethane (1:2, 12 mL) as per the procedure described in Step 1 of Intermediate 1 to yield 421 mg of the product. $^1$H NMR (300 MHz, DMSO-$d_6$) δ 0.56-0.60 (m, 2H), 0.82-0.88 (m, 2H), 1.95-1.99 (m, 1H), 2.26 (s, 3H), 6.80 (s, 1H), 7.00 (d, J=7.8 Hz, 1H), 7.22 (d, J=7.8 Hz, 1H), 8.19 (d, J=8.7 Hz, 2H), 8.34 (d, J=8.7 Hz, 2H), 10.17 (s, 1H).

Step 2: N-(2-Cyclopropyl-4-methylphenyl)-N-methyl-4-nitrobenzamide

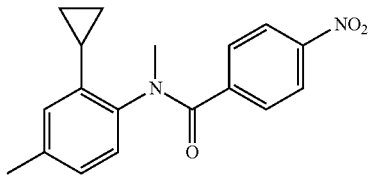 [SMILES: Cc1ccc(N(C)C(=O)c2ccc([N+](=O)[O-])cc2)c(C2CC2)c1]

The titled compound was prepared by the reaction of Step 1 intermediate (411 mg, 1.38 mmol) with methyl iodide (104 µL, 1.66 mmol) using sodium hydride (60% w/w, 67 mg, 1.66 mmol) in anhydrous DMF (8.0 mL) as per the procedure described in Step 2 of Intermediate 1 to yield 440 mg of the product. $^1$H NMR (300 MHz, DMSO-$d_6$) δ 0.50-0.55 (m, 1H), 0.64-0.69 (m, 1H), 0.95-1.02 (m, 2H), 1.82-1.87 (m, 1H), 2.14 (s, 3H), 3.31 (s, 3H), 6.55 (s, 1H), 6.85 (d, J=8.7 Hz, 1H), 7.10 (d, J=7.8 Hz, 1H), 7.53 (d, J=9.0 Hz, 2H), 8.04 (d, J=8.7 Hz, 2H).

Step 3: 4-Amino-N-(2-cyclopropyl-4-methylphenyl)-N-methylbenzamide

The titled compound was prepared by the reduction of Step 2 intermediate (434 mg, 1.39 mmol) using iron powder (232 mg, 4.17 mmol) and ammonium chloride (473 mg, 13.98 mmol) in a mixture of ethanol and water (5:1, 12 mL) as per the procedure described in Step 3 of Intermediate 1 to obtain 320 mg of the product. $^1$H NMR (300 MHz, DMSO-$d_6$) δ 0.57-0.62 (m, 2H), 0.84-0.96 (m, 2H), 1.78-1.84 (m, 1H), 2.20 (s, 3H), 3.20 (s, 3H), 5.36 (s, 2H), 6.25-6.31 (m, 2H), 6.62 (s, 1H), 6.88-6.93 (m, 2H), 6.95-6.99 (m, 2H).

Intermediate 26

4-Amino-N-(4-chloro-2-fluoro-5-methylphenyl)-N-methylbenzamide

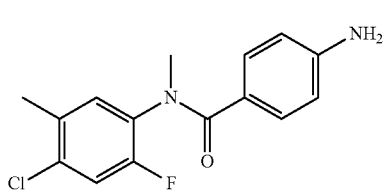 [SMILES: Cc1cc(N(C)C(=O)c2ccc(N)cc2)c(F)cc1Cl]

Step 1: N-(4-Chloro-2-fluoro-5-methylphenyl)-4-nitrobenzamide

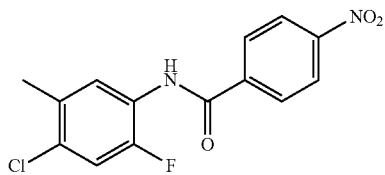 [SMILES: Cc1cc(NC(=O)c2ccc([N+](=O)[O-])cc2)c(F)cc1Cl]

The titled compound was prepared by the reaction of 4-chloro-2-fluoro-5-methylaniline (252 mg, 1.57 mmol) with 4-nitrobenzoylchloride (293 mg, 1.57 mmol) in a mixture of pyridine and dichloromethane (1:2, 6.0 mL) as per the procedure described in Step 1 of Intermediate 1 to yield 398 mg of the product. $^1$H NMR (300 MHz, DMSO-$d_6$) δ 2.32 (s, 3H), 7.53 (d, J=10.2 Hz, 1H), 7.62 (d, J=8.4 Hz, 1H), 8.19 (d, J=9.0 Hz, 2H), 8.37 (d, J=8.7 Hz, 2H), 10.51 (s, 1H).

Step 2: N-(4-Chloro-2-fluoro-5-methylphenyl)-N-methyl-4-nitrobenzamide

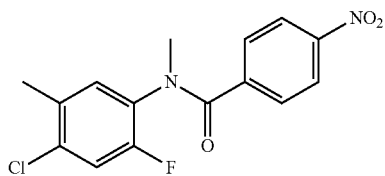 [SMILES: Cc1cc(N(C)C(=O)c2ccc([N+](=O)[O-])cc2)c(F)cc1Cl]

The titled compound was prepared by the reaction of Step 1 intermediate (391 mg, 1.26 mmol) with methyl iodide (95 µL, 1.51 mmol) using sodium hydride (60% w/w, 61 mg, 1.51 mmol) in anhydrous DMF (8.0 mL) as per the procedure described in Step 2 of Intermediate 1 to yield 396 mg of the product. The intermediate was as such used for the next step without characterization.

Step 3: 4-Amino-N-(4-chloro-2-fluoro-5-methylphenyl)-N-methylbenzamide

The titled compound was prepared by the reduction of Step 2 intermediate (390 mg, 1.20 mmol) using iron powder (202 mg, 3.62 mmol) and ammonium chloride (647 mg, 12.08 mmol) in a mixture of ethanol and water (5:1, 12 mL) as per the procedure described in Step 3 of Intermediate 1 to obtain 260 mg of the product. $^1$H NMR (300 MHz, DMSO-$d_6$) δ 2.42 (s, 3H), 3.21 (s, 3H), 5.49 (s, 2H), 6.34 (d, J=8.1 Hz, 2H), 6.99 (d, J=8.4 Hz, 2H), 7.34-7.44 (m, 2H); ESI-MS (m/z) 293 (M+H)$^+$.

Intermediate 27

4-Amino-N-(2-chloro-4-cyclopropylphenyl)-N-methylbenzamide

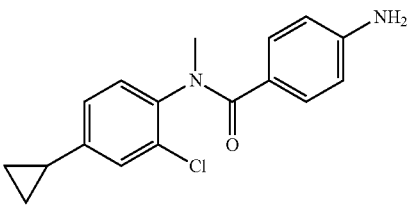

Step 1:
N-(2-Chloro-4-cyclopropylphenyl)-4-nitrobenzamide

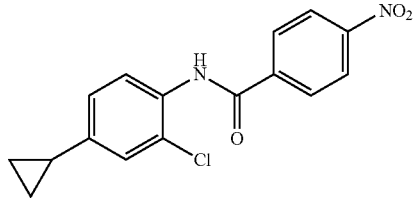 [SMILES: O=C(Nc1ccc(C2CC2)cc1Cl)c1ccc([N+](=O)[O-])cc1]

The titled compound was prepared by the reaction of 2-chloro-4-cyclopropylaniline (252 mg, 1.50 mmol) with 4-nitrobenzoylchloride (279 mg, 1.50 mmol) in a mixture of pyridine and dichloromethane (1:2, 9.0 mL) as per the procedure described in Step 1 of Intermediate 1 to yield 362 mg of the product. $^1$H NMR (300 MHz, DMSO-$d_6$) δ 0.68-0.75 (m, 2H), 0.93-1.01 (m, 2H), 1.93-1.97 (m, 1H), 7.08 (d, J=7.8 Hz, 1H), 7.26 (s, 1H), 7.40 (d, J=7.8 Hz, 1H), 8.18 (d, J=8.4 Hz, 2H), 8.36 (d, J=8.7 Hz, 2H), 10.34 (s, 1H).

Step 2: N-(2-Chloro-4-cyclopropylphenyl)-N-methyl-4-nitrobenzamide

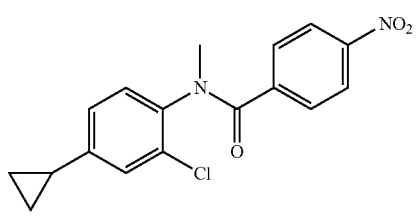 [SMILES: CN(C(=O)c1ccc([N+](=O)[O-])cc1)c1ccc(C2CC2)cc1Cl]

The titled compound was prepared by the reaction of Step 1 intermediate (356 mg, 1.12 mmol) with methyl iodide (85 μL, 1.34 mmol) using sodium hydride (60% w/w, 54 mg, 1.35 mmol) in anhydrous DMF (8.0 mL) as per the procedure described in Step 2 of Intermediate 1 to yield 364 mg of the product. $^1$H NMR (300 MHz, DMSO-$d_6$) δ 0.60-0.66 (m, 2H), 0.89-0.95 (m, 2H), 1.83-1.87 (m, 1H), 3.25 (s, 3H), 6.98 (d, J=6.9 Hz, 1H), 7.13 (s, 1H), 7.41 (d, J=8.1 Hz, 1H), 7.52 (d, J=8.7 Hz, 2H), 8.06 (d, J=8.7 Hz, 2H).

Step 3: 4-Amino-N-(2-chloro-4-cyclopropylphenyl)-N-methylbenzamide

The titled compound was prepared by the reduction of Step 2 intermediate (352 mg, 1.06 mmol) using iron powder (178 mg, 3.19 mmol) and ammonium chloride (570 mg, 10.64 mmol) in a mixture of ethanol and water (5:1, 12 mL) as per the procedure described in Step 3 of Intermediate 1 to obtain 230 mg of the product. $^1$H NMR (300 MHz, DMSO-$d_6$) δ 0.65-0.71 (m, 2H), 0.92-0.96 (m, 2H), 1.87-1.92 (m, 1H), 3.14 (s, 3H), 5.44 (s, 2H), 6.29 (d, J=7.8 Hz, 2H), 6.94-6.99 (m, 3H), 7.17 (d, J=7.2 Hz, 2H).

Intermediate 28
4-Amino-N-(5-cyclopropyl-2-methylphenyl)-N-methylbenzamide

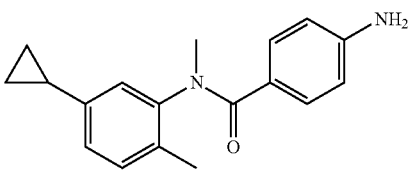

Step 1:
N-(5-Cyclopropyl-2-methylphenyl)-4-nitrobenzamide

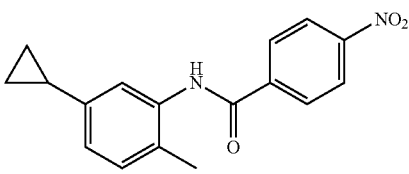 [SMILES: Cc1ccc(C2CC2)cc1NC(=O)c1ccc([N+](=O)[O-])cc1]

The titled compound was prepared by the reaction of 5-cyclopropyl-2-methylaniline (558 mg, 3.79 mmol) with 4-nitrobenzoylchloride (703 mg, 3.79 mmol) in a mixture of pyridine and dichloromethane (1:2, 15 mL) as per the procedure described in Step 1 of Intermediate 1 to yield 1.1 g of the product. $^1$H NMR (300 MHz, DMSO-$d_6$) δ 0.60-0.64 (m, 2H), 0.89-0.96 (m, 2H), 1.88-1.92 (m, 1H), 2.17 (s, 3H), 6.91 (d, J=7.8 Hz, 1H), 7.05 (s, 1H), 7.15 (d, J=7.8 Hz, 1H), 8.19 (d, J=8.7 Hz, 2H), 8.36 (d, J=8.7 Hz, 2H), 10.17 (s, 1H); APCI-MS (m/z) 297 (M+H)$^+$.

Step 2: N-(5-Cyclopropyl-2-methylphenyl)-N-methyl-4-nitrobenzamide

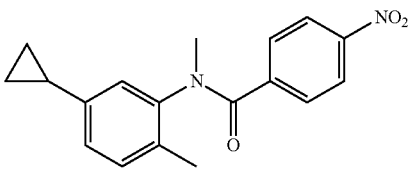 [SMILES: Cc1ccc(C2CC2)cc1N(C)C(=O)c1ccc([N+](=O)[O-])cc1]

The titled compound was prepared by the reaction of Step 1 intermediate (1.02 g, 3.44 mmol) with methyl iodide (260 μL, 4.13 mmol) using sodium hydride (60% w/w, 165 mg, 4.13 mmol) in anhydrous DMF (10 mL) as per the procedure described in Step 2 of Intermediate 1 to yield 1.0 g of the product. $^1$H NMR (300 MHz, DMSO-$d_6$) δ 0.39-0.42 (m, 1H), 0.60-0.65 (m, 1H), 0.84-0.88 (m, 2H), 1.74-1.78 (m, 1H), 2.11 (s, 3H), 3.25 (s, 3H), 6.85-6.93 (m, 2H), 7.01 (d, J=7.8 Hz, 1H), 7.49 (d, J=7.8 Hz, 2H), 8.03 (d, J=7.2 Hz, 2H).

Step 3: 4-Amino-N-(5-cyclopropyl-2-methylphenyl)-N-methylbenzamide

The titled compound was prepared by the reduction of Step 2 intermediate (1.0 g, 3.22 mmol) using iron powder (540 mg, 9.66 mmol) and ammonium chloride (1.7 g, 32.22 mmol) in a mixture of ethanol and water (5:1, 20 mL) as per the procedure described in Step 3 of Intermediate 1 to obtain 782 mg of the product. $^1$H NMR (300 MHz, DMSO-$d_6$) δ 0.41-0.46 (m, 1H), 0.60-0.65 (m, 1H), 0.84-0.90 (m, 2H), 1.78-1.82 (m, 1H), 2.00 (s, 3H), 3.15 (s, 3H), 5.39 (s, 2H), 6.24-6.28 (m, 2H), 6.82 (d, J=7.2 Hz, 2H), 6.90-6.95 (m, 2H), 6.98-6.03 (m, 1H); APCI-MS (m/z) 281 (M+H)$^+$.

Intermediate 29

4-Amino-N-(2-chloro-5-cyclopropylphenyl)-N-methylbenzamide

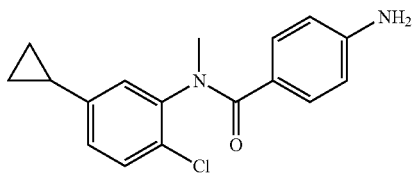 [SMILES: CN(C(=O)c1ccc(N)cc1)c1cc(C2CC2)ccc1Cl]

Step 1: N-(2-Chloro-5-cyclopropylphenyl)-4-nitrobenzamide

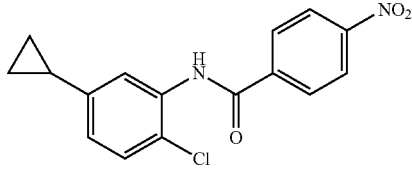 [SMILES: O=C(Nc1cc(C2CC2)ccc1Cl)c1ccc([N+](=O)[O-])cc1]

The titled compound was prepared by the reaction of 2-chloro-5-cyclopropylaniline (728 mg, 4.34 mmol) with 4-nitrobenzoylchloride (806 mg, 4.34 mmol) in a mixture of pyridine and dichloromethane (1:2, 10 mL) as per the procedure described in Step 1 of Intermediate 1 to yield 1.08 g of the product. $^1$H NMR (300 MHz, DMSO-$d_6$) δ 0.65-0.69 (m, 2H), 0.95-098 (m, 2H), 1.93-1.97 (m, 1H), 7.02 (d, J=8.4 Hz, 1H), 7.27 (s, 1H), 7.40 (d, J=8.4 Hz, 1H), 8.18 (d, J=8.7 Hz, 2H), 8.36 (d, J=8.7 Hz, 2H), 10.36 (s, 1H).

Step 2: N-(2-Chloro-5-cyclopropylphenyl)-N-methyl-4-nitrobenzamide

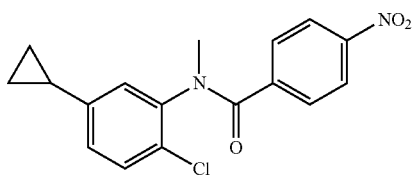 [SMILES: CN(C(=O)c1ccc([N+](=O)[O-])cc1)c1cc(C2CC2)ccc1Cl]

The titled compound was prepared by the reaction of Step 1 intermediate (829 mg, 2.61 mmol) with methyl iodide (196 μL, 3.14 mmol) using sodium hydride (60% w/w, 126 mg, 3.14 mmol) in anhydrous DMF (8.0 mL) as per the procedure described in Step 2 of Intermediate 1 to yield 841 mg of the product. $^1$H NMR (300 MHz, DMSO-$d_6$) δ 0.48-0.52 (m, 1H), 0.68-0.72 (m, 1H), 0.89-0.95 (m, 2H), 1.80-1.85 (m, 1H), 3.28 (s, 3H), 7.01 (d, J=9.0 Hz, 1H), 7.22-7.28 (m, 2H), 7.53 (d, J=9.0 Hz, 2H), 8.07 (d, J=8.4 Hz, 2H).

Step 3: 4-Amino-N-(2-chloro-5-cyclopropylphenyl)-N-methylbenzamide

The titled compound was prepared by the reduction of Step 2 intermediate (830 mg, 2.50 mmol) using iron powder (419 mg, 7.51 mmol) and ammonium chloride (1.3 g, 25.09 mmol) in a mixture of ethanol and water (5:1, 15 mL) as per the procedure described in Step 3 of Intermediate 1 to obtain 521 mg of the product. $^1$H NMR (300 MHz, DMSO-$d_6$) δ 0.65-0.70 (m, 2H), 0.88-0.95 (m, 2H), 1.83-1.87 (m, 1H), 3.16 (s, 3H), 5.43 (s, 2H), 6.29-6.33 (m, 2H), 6.95-7.03 (m, 4H), 7.25-7.29 (m, 1H); APCI-MS (m/z) 301 (M+H)$^+$.

EXAMPLES

General Procedures for the Synthesis of Examples 1□40
Method A

Preparation of N-(4-chlorophenyl)-4-(2-(4-(1,1-difluoro-2-hydroxyethyl)phenyl)acetamido)-N-methylbenzamide (Example 3)

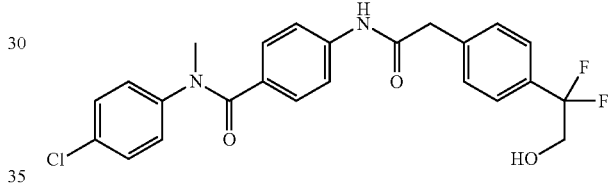

Step 1: Ethyl 2-(4-(2-((4-((4-chlorophenyl)(methyl)carbamoyl)phenyl)amino)-2-oxoethyl)phenyl)-2,2-difluoroacetate (Example 1)

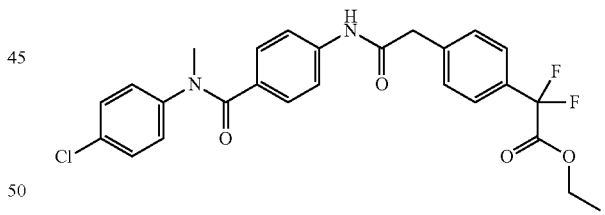

To a stirred solution of Intermediate 1 (161 mg, 0.62 mmol) and Intermediate 2 (177 mg, 0.68 mmol) in DMF (8.0 mL) were added EDCI.HCl (179 mg, 0.93 mmol), HOBt (126 mg, 0.93 mmol) and triethylamine (261 μL, 1.86 mmol) at RT. The reaction was stirred overnight at RT. The reaction mixture was poured into water (20 mL) and extracted with ethyl acetate (70 mL×3). The combined organic layers were washed with brine (50 mL), dried over anhydrous sodium sulfate and concentrated. The crude material obtained was purified by silica gel column chromatography to obtain 30 mg of the product. $^1$H NMR (300 MHz, DMSO-$d_6$) δ 1.21 (t, J=6.9 Hz, 3H), 3.33 (s, 3H), 3.70 (s, 2H), 4.30 (q, J=7.2 Hz, 2H), 7.17 (t, J=9.3 Hz, 4H), 7.31 (d, J=8.7 Hz, 2H), 7.42-7.55 (m, 6H), 10.32 (s, 1H); ESI-MS (m/z) 501 (M+H)$^+$.

Step 2: N-(4-Chlorophenyl)-4-(2-(4-(1,1-difluoro-2-hydroxyethyl)phenyl)acetamido)-N-methylbenzamide To a stirred solution of Step 1 intermediate (81 mg, 0.16 mmol) in methanol (5.0 mL) at 0° C. was added sodium borohydride (13 mg, 0.33 mmol). The reaction mixture was stirred at 0° C. for 1 h. The reaction was quenched with aqueous ammonium chloride (20 mL), poured into water (20 mL) and extracted with ethyl acetate (70 mL×2). The combined organic layers were dried over anhydrous sodium sulfate and concentrated under reduced pressure. The crude material obtained was purified by flash chromatography to obtain 23 mg of the desired product. $^1$H NMR (300 MHz, DMSO-$d_6$) δ 3.34 (s, 3H), 3.67 (s, 2H), 3.78-3.84 (m, 2H), 5.58-5.62 (m, 1H), 7.17 (t, J=9.3 Hz, 4H), 7.32 (d, J=8.4 Hz, 3H), 7.39-7.45 (m, 5H), 10.31 (s, 1H); ESI-MS (m/z) 459 (M+H)$^+$.

Method B

Preparation of 4-(2-(4-(2-amino-1,1-difluoro-2-oxo-ethyl)phenyl)acetamido)-N-(4-chlorophenyl)-N-methylbenzamide (Example 2)

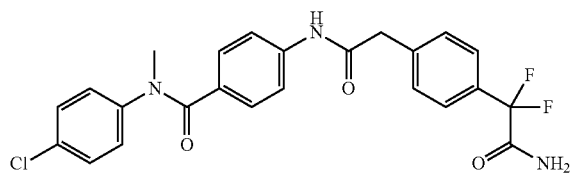 [SMILES: CN(C(=O)c1ccc(NC(=O)Cc2ccc(C(F)(F)C(N)=O)cc2)cc1)c1ccc(Cl)cc1]

To a stirred solution of ethyl 2-(4-(2-((4-((4-chlorophenyl)(methyl)carbamoyl)phenyl)amino)-2-oxoethyl)phenyl)-2,2-difluoroacetate (Example 1) (83 mg, 0.16 mmol) in 1,4-dioxane (5.0 mL) was added aqueous ammonia (10 mL) and the reaction was stirred overnight at RT under sealed condition. The reaction was diluted with ethyl acetate (50 mL) and washed with brine (30 ml). The organic layer was concentrated under reduced pressure and triturated with diethyl ether and n-pentane to yield 26 mg of the desired product. $^1$H NMR (300 MHz, DMSO-$d_6$) δ 3.33 (s, 3H), 3.69 (s, 2H), 7.15-7.19 (m, 4H), 7.32 (d, J=8.4 Hz, 2H), 7.42-7.51 (m, 6H), 7.99 (s, 1H), 8.33 (s, 1H), 10.32 (s, 1H); ESI-MS (m/z) 472 (M+H)$^+$.

Method C

Preparation of N-(2,5-Dichlorophenyl)-4-(2-(4-(1,1-difluoro-2-hydroxypropyl)phenyl)acetamido)-N-methylbenzamide (Example 5)

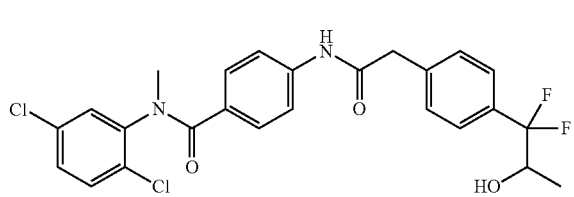 [SMILES: CC(O)C(F)(F)c1ccc(CC(=O)Nc2ccc(C(=O)N(C)c3cc(Cl)ccc3Cl)cc2)cc1]

Step 1: Preparation of N-(2,5-dichlorophenyl)-4-(2-(4-(1,1-difluoro-2-oxopropyl)phenyl)acetamido)-N-methylbenzamide

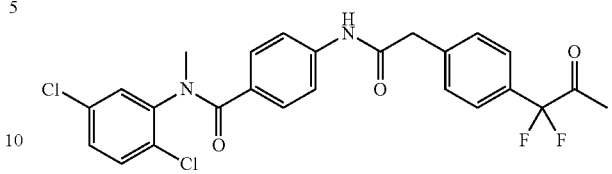

To a stirred solution of Intermediate 4 (120 mg, 0.52 mmol) and Intermediate 5 (138 mg, 0.47 mmol) in DMF (5.0 mL) at 0° C. were added N,N'-diisopropylethylamine (269 μL, 1.57 mmol) and propylphosphonic anhydride (624 μL, 1.05 mmol). The mixture was stirred overnight at RT. The reaction mixture was diluted with water (20 mL) and extracted with ethyl acetate (70 mL×2). The combined organic layers were washed with brine (100 mL), dried over anhydrous sodium sulfate and concentrated under reduced pressure. The crude material obtained was purified by silica gel column chromatography to obtain 157 mg of the desired product. $^1$H NMR (300 MHz, CDCl$_3$) δ 1.93 (s, 3H), 2.32 (s, 3H), 3.70 (s, 2H), 7.10-7.13 (m, 2H), 7.23-7.27 (m, 5H), 7.39 (d, J=8.1 Hz, 2H), 7.52 (d, J=7.8 Hz, 2H); APCI-MS (m/z) 504 (M−H)$^-$.

Step 2: N-(2,5-Dichlorophenyl)-4-(2-(4-(1,1-difluoro-2-hydroxypropyl)phenyl)acetamido)-N-methylbenzamide The titled compound was prepared by the reduction of Step 1 intermediate (137 mg, 0.27 mmol) using sodium borohydride (12 mg, 0.32 mmol) in methanol (5.0 mL) as per the procedure described in step 2 of Method A to yield 49 mg of the product. $^1$H NMR (300 MHz, DMSO-$d_6$) δ 1.08 (d, J=6.3 Hz, 3H), 3.23 (s, 3H), 3.66 (s, 2H), 3.99-4.05 (m, 1H), 5.49 (d, J=6.3 Hz, 1H), 7.24 (br s, 2H), 7.36-7.44 (m, 8H), 7.71 (s, 1H), 10.30 (s, 1H); APCI-MS (m/z) 506 (M−H)$^-$.

Method D

Preparation of 4-(2-(4-(1,1-difluoro-2-hydroxy-2-methylpropyl)phenyl)acetamido)-N-(3,5-dimethylphenyl)-N-methylbenzamide (Example 9)

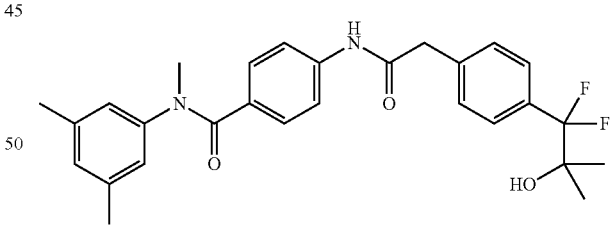

Step 1: 4-(2-(4-(1,1-Difluoro-2-oxopropyl)phenyl)acetamido)-N-(3,5-dimethylphenyl)-N-methylbenzamide

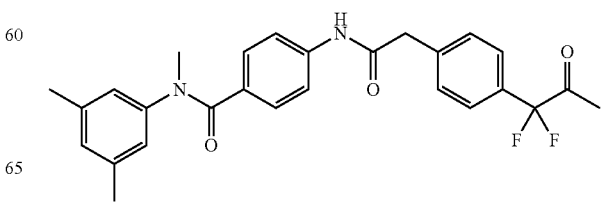

The titled compound was prepared by the reaction of Intermediate 8 (346 mg, 1.36 mmol) with Intermediate 4 (373 mg, 1.63 mmol) in the presence of EDCI.HCl (391 mg, 2.04 mmol), HOBt (276 mg, 2.04 mmol) and triethylamine (570 μL, 4.08 mmol) in DMF (10 mL) as per the procedure described in Step 1 of Method A to yield 194 mg of the desired product. 1H NMR (300 MHz, DMSO-$d_6$) δ 2.12 (s, 6H), 2.33 (s, 3H), 3.27 (s, 3H), 3.68 (s, 2H), 6.73 (s, 2H), 6.77 (s, 1H), 7.18 (d, J=9.0 Hz, 2H), 7.40-7.52 (m, 6H), 10.27 (s, 1H).

Step 2: 4-(2-(4-(1,1-Difluoro-2-hydroxy-2-methylpropyl)phenyl)acetamido)-N-(3,5-dimethylphenyl)-N-methylbenzamide To a stirred solution of Step 1 intermediate (81 mg, 0.17 mmol) in THF (15 mL) at 0° C. was added methylmagnesium bromide (50 μL, 0.43 mmol) and the mixture was stirred at 0° C. for 2 h. The mixture was quenched with aqueous ammonium chloride solution (20 mL) and extracted with ethyl acetate (50 mL×2). The combined organic layers were washed with brine (50 mL), concentrated and the residue obtained was purified by silica gel column chromatography to obtain 32 mg of the desired product. $^1$H NMR (300 MHz, DMSO-$d_6$) δ 1.14 (s, 6H), 2.14 (s, 6H), 3.29 (s, 3H), 3.66 (s, 2H), 5.25 (s, 1H), 6.75 (s, 2H), 6.78 (s, 1H), 7.21 (d, J=7.8 Hz, 2H), 7.35-7.42 (m, 6H), 10.27 (s, 1H); ESI-MS (m/z) 481 (M+H)$^+$.

Method E

Preparation of N-(3,5-dichlorophenyl)-4-(2-(4-(1,1-difluoro-2-hydroxypropyl)phenyl)acetamido)-N-methylbenzamide (Example 21)

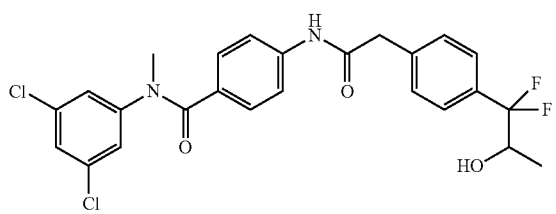 [SMILES: CC(O)C(F)(F)c1ccc(CC(=O)Nc2ccc(C(=O)N(C)c3cc(Cl)cc(Cl)c3)cc2)cc1]

Step 1: Ethyl 2-(4-(2-((4-((3,5-dichlorophenyl)(methyl)carbamoyl)phenyl)amino)-2-oxoethyl)phenyl)-2,2-difluoroacetate

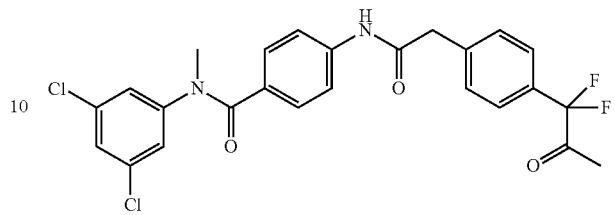

The titled compound was prepared by the reaction of Intermediate 14 (250 mg, 0.84 mmol) and Intermediate 2 (219 mg, 0.84 mmol) in DMF (8.0 mL) by following the procedure described in Step 1 of Method A or Step 1 of Method C to yield 173 mg of the product. 1H NMR (300 MHz, DMSO-$d_6$) δ 1.22 (t, J=7.5 Hz, 3H), 3.32 (s, 3H), 3.73 (s, 2H), 4.29 (q, J=7.2 Hz, 2H), 7.26 (d, J=8.1 Hz, 2H), 7.31 (s, 2H), 7.40 (s, 1H), 7.40-7.54 (m, 6H), 10.35 (s, 1H).

Step 2: N-(3,5-Dichlorophenyl)-4-(2-(4-(1,1-difluoro-2-oxopropyl)phenyl)acetamido)-N-methylbenzamide

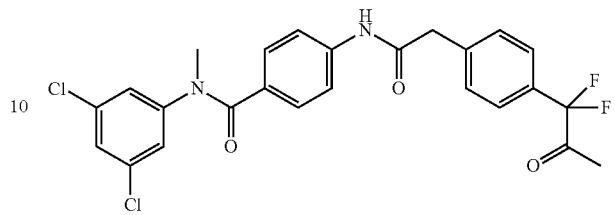

To a stirred solution of Step 1 intermediate (167 mg, 0.31 mmol) in THF (10 mL) at −78° C. was added methyl lithium (260 μL, 0.78 mmol) and the mixture was gradually allowed to attain −50° C. The reaction mixture was quenched with aqueous ammonium chloride (25 mL) and extracted with ethyl acetate (70 mL×2). The combined organic layers were washed with brine and concentrated under reduced pressure. Crude was purified by flash chromatography to obtain 89 mg of the product. $^1$H NMR (300 MHz, DMSO-$d_6$) δ 1.11 (s, 3H), 3.32 (s, 3H), 3.70 (s, 2H), 7.23 (d, J=8.7 Hz, 2H), 7.29 (s, 2H), 7.31-7.37 (m, 1H), 7.42-7.52 (m, 6H), 10.32 (s, 1H).

Step 3: N-(3,5-Dichlorophenyl)-4-(2-(4-(1,1-difluoro-2-hydroxypropyl)phenyl)acetamido)-N-methylbenzamide The titled compound was prepared by the reduction of Step 2 intermediate (81 mg, 0.16 mmol) using sodium borohydride (7.0 mg, 0.92 mmol) in methanol (6.0 mL) as per the procedure described in step 2 of Method A to yield 38 mg of the product. $^1$H NMR (300 MHz, DMSO-$d_6$) δ 1.06 (d, J=6.0 Hz, 3H), 3.32 (s, 3H), 3.68 (s, 2H), 3.99-4.04 (m, 1H), 5.49 (br s, 1H), 7.23-7.25 (d, J=8.7 Hz, 2H), 7.28-7.33 (m, 3H), 7.38-7.43 (m, 4H), 7.50 (d, J=8.7 Hz, 2H), 10.32 (s, 1H); APCI-MS (m/z) 505 (M−H)$^−$.

Method F

Preparation of (R)—N-(2-Chloro-4-methylphenyl)-4-(2-(4-(1,1-difluoro-2-hydroxypropyl)phenyl)acetamido)-N-methylbenzamide (Example 29)

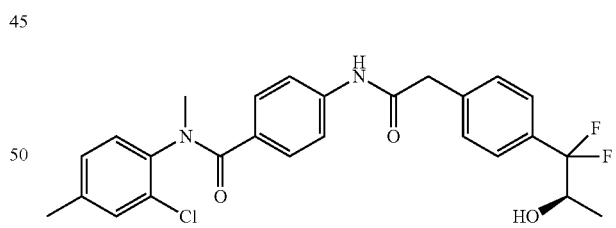

Step 1: N-(2-Chloro-4-methylphenyl)-4-(2-(4-(1,1-difluoro-2-oxopropyl)phenyl)acetamido)-N-methylbenzamide

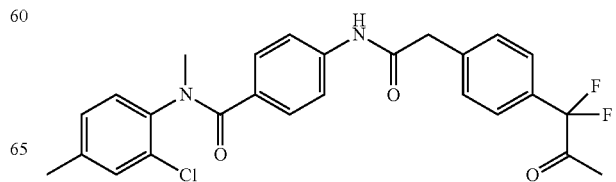

The titled compound was prepared by the reaction of 4-amino-N-(2-chloro-4-methylphenyl)-N-methylbenzamide (Intermediate 16) (11.25 g, 40.95 mmol) and 2-(4-(2-ethoxy-1,1-difluoro-2-oxoethyl)phenyl)acetic acid (Intermediate 2) (12.69 g, 49.14 mmol) using N,N'-diisopropylethylamine (21 mL, 123 mmol) and propylphosphonic anhydride (50% in EtOAc, 49 mL, 81.9 mmol) in DMF (150 mL) followed by reaction with methyl lithium (12.94 mL, 38.83 mmol) in THF (400 mL) as per the procedure described in Step 1 and Step 2 of Method E to yield 5.9 g of the product. $^1$H NMR (300 MHz, DMSO-$d_6$) δ 2.22 (s, 3H), 2.35 (s, 3H), 3.19 (s, 3H), 3.68 (s, 2H), 7.07-7.12 (m, 1H), 7.23 (d, J=8.7 Hz, 2H), 7.27 (d, J=9.6 Hz, 2H), 7.31 (s, 1H), 7.39 (d, J=7.5 Hz, 2H), 7.42-7.52 (m, 3H), 10.28 (s, 1H).

Step 2: (R)—N-(2-Chloro-4-methylphenyl)-4-(2-(4-(1,1-difluoro-2-hydroxypropyl)phenyl)acetamido)-N-methylbenzamide (Crude)

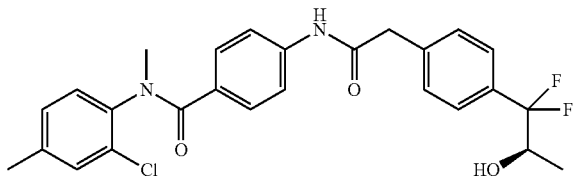 [SMILES: CC(=O)C(F)(F)c1ccc(CC(=O)Nc2ccc(C(=O)N(C)c3ccc(C)cc3Cl)cc2)cc1]

To a stirred solution of (S)-(+)-2-methyl-CBS-oxaborolidine (1M in toluene, 1.05 mL) [Ref: (i) Corey, E. J; Helal, C. J. Angew. Chem. Int. Ed. 1998, 37, 1986 □2012 (ii) Corey, E. J.; Bakshi, R. K.; Shibata, S. J. Am. Chem. Soc. 1987, 109 (18), 5551□553] in anhydrous THF (20 mL) was added borane dimethyl sulfide complex (214 μL, 2.25 mmol) at 0° C. and the mixture was stirred for 30 min at the same temperature. A solution of Step 1 Intermediate (1.0 g, 2.05 mmol) in THF (10 mL) was drop wise added to the reaction mixture over a period of 10 min at RT. The resultant mixture was stirred at RT for 20 min. The reaction mixture was quenched with methanol (10 mL) and concentrated under reduced pressure. The residue obtained was purified by flash silica gel column chromatography to yield 721 mg of the titled product. $^1$H NMR (300 MHz, DMSO-$d_6$) δ 1.05 (d, J=5.7 Hz, 3H), 2.22 (s, 3H), 3.20 (s, 3H), 3.65 (s, 2H), 3.98-4.03 (m, 1H), 5.49 (d, J=6.0 Hz, 1H), 7.05-7.11 (m, 2H), 7.19 (d, J=8.1 Hz, 2H), 7.23-7.27 (m, 2H), 7.35-7.42 (m, 5H), 10.26 (s, 1H); chiral HPLC purity: 91.40%.

Step 3: (S)—(R)-1-(4-(2-((4-((2-Chloro-4-methylphenyl)(methyl)carbamoyl)phenyl)amino)-2-oxoethyl)phenyl)-1,1-difluoropropan-2-yl 2-(((benzyloxy)carbonyl)amino)-3-phenylpropanoate

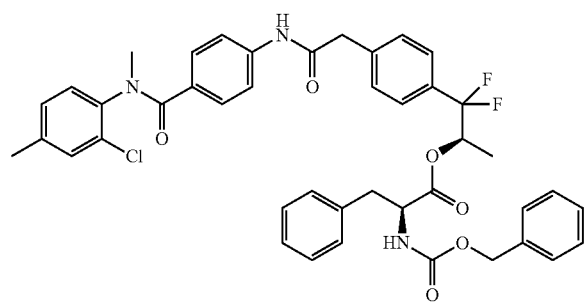 [SMILES: Cc1ccc(N(C)C(=O)c2ccc(NC(=O)Cc3ccc(C(F)(F)[C@@H](C)OC(=O)[C@H](Cc4ccccc4)NC(=O)OCc4ccccc4)cc3)cc2)c(Cl)c1]

To a stirred solution of Step 2 product (502 mg, 1.03 mmol), N-benzyloxycarbonyl-L-phenylalanine (487 mg, 1.54 mmol) and DIPEA (0.7 mL, 4.12 mmol) in dichloromethane (20 mL) were added BOP (911 mg, 2.06 mmol) and DMAP (63 mg, 0.51 mmol) at 0° C. The resultant mixture was warmed up to RT and stirred for 16 h. The reaction mixture was diluted with ethyl acetate (200 mL) and washed with saturated aqueous solution of ammonium chloride (100 mL), saturated aqueous sodium bicarbonate solution (100 mL), water (100 mL) and brine (100 mL). The organic layer was dried over anhydrous sodium sulfate, concentrated and the residue thus obtained was purified by flash silica gel column chromatography to yield 655 mg of the titled product. The intermediate was as such carried forward to the next step without any characterization.

Step 4: (R)—N-(2-Chloro-4-methylphenyl)-4-(2-(4-(1,1-difluoro-2-hydroxypropyl)phenyl)acetamido)-N-methylbenzamide To a stirred solution of Step 3 Intermediate (215 mg, 0.31 mmol) in a mixture of THF (6.0 mL), methanol (4.0 mL) and water (2.0 mL) was added lithium hydroxide monohydrate (39 mg, 0.93 mmol) and the mixture was stirred at RT for 30 min. The reaction mixture was quenched with 1N HCl (10 mL) and the product was extracted in ethyl acetate (2×20 mL). The combined organic layers were washed with water (20 mL) and brine (10 mL). The organic layer was dried over anhydrous sodium sulfate and concentrated under reduced pressure. The residue obtained was purified by flash silica gel column chromatography to yield 93 mg of the titled product. $^1$H NMR (300 MHz, DMSO-$d_6$) δ 1.05 (d, J=5.7 Hz, 3H), 2.22 (s, 3H), 3.19 (s, 3H), 3.65 (s, 2H), 3.98-4.03 (m, 1H), 5.49 (d, J=6.0 Hz, 1H), 7.03-7.09 (m, 2H), 7.19 (d, J=8.1 Hz, 2H), 7.23-7.27 (m, 2H), 7.35-7.41 (m, 5H), 10.26 (s, 1H); APCI-MS (m/z) 485 (M−H)$^-$; Chiral HPLC purity: 94.76%.

Method G

Preparation of (S)—N-(2-Chloro-4-methylphenyl)-4-(2-(4-(1,1-difluoro-2-hydroxypropyl)phenyl)acetamido)-N-methylbenzamide (Example 30)

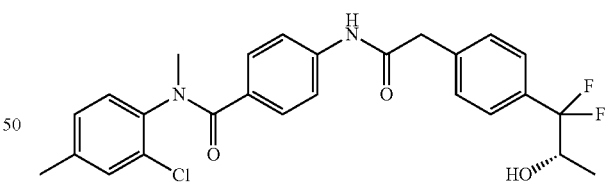

Step 1: (S)—N-(2-Chloro-4-methylphenyl)-4-(2-(4-(1,1-difluoro-2-hydroxypropyl)phenyl)acetamido)-N-methylbenzamide (Crude)

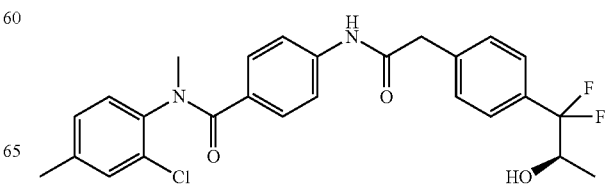

To a stirred solution of (R)-(+)-2-methyl-CBS-oxaborolidine (1M in toluene, 1.05 mL) [Ref: (i) Corey, E. J; Helal, C. J. Angew. Chem. Int. Ed. 1998, 37, 1986 □012 (ii) Corey, E. J.; Bakshi, R. K.; Shibata, S. J. Am. Chem. Soc. 1987, 109 (18), 5551□553] in anhydrous THF (20 mL) was added borane dimethyl sulfide complex (214 µL, 2.25 mmol) at 0° C. and the mixture was stirred for 30 min at the same temperature. A solution of N-(2-chloro-4-methylphenyl)-4-(2-(4-(1,1-difluoro-2-oxopropyl)phenyl)acetamido)-N-methylbenzamide (Step 1 intermediate of Example 29) (1.0 g, 2.05 mmol) in THF (10 mL) was drop wise added to the reaction mixture over a period of 10 min at RT. The resultant mixture was stirred at RT for 20 min. The reaction mixture was quenched with methanol (10 mL) and concentrated under reduced pressure. The residue obtained was purified by flash silica gel column chromatography to yield 672 mg of the titled product. $^1$H NMR (300 MHz, DMSO-$d_6$) δ 1.06 (d, J=6.3 Hz, 3H), 2.22 (s, 3H), 3.20 (s, 3H), 3.65 (s, 2H), 3.98-4.05 (m, 1H), 5.48 (d, J=6.0 Hz, 1H), 6.98-7.12 (m, 1H), 7.20 (d, J=8.1 Hz, 2H), 7.24-7.30 (m, 2H), 7.35-7.42 (m, 6H), 10.26 (s, 1H); chiral HPLC purity: 90.76%.

Step 2: (S)—(S)-1-(4-(2-((4-((2-Chloro-4-methylphenyl)(methyl)carbamoyl)phenyl)amino)-2-oxoethyl)phenyl)-1,1-difluoropropan-2-yl 2-(((benzyloxy)carbonyl)amino)-3-phenylpropanoate

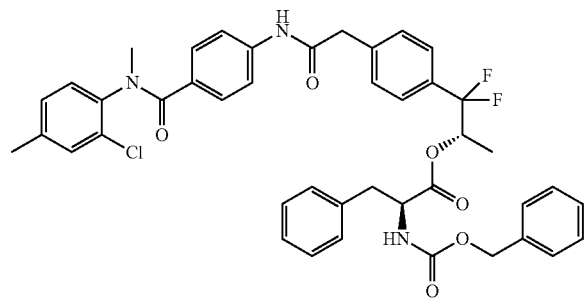

To a stirred solution of Step 1 product (502 mg, 1.03 mmol), N-benzyloxycarbonyl-L-phenylalanine (487 mg, 1.54 mmol) and DIPEA (0.7 mL, 4.12 mmol) in dichloromethane (20 mL) were added BOP (911 mg, 2.06 mmol) and DMAP (63 mg, 0.51 mmol) at 0° C. The resultant mixture was warmed up to RT and stirred for 16 h. The reaction mixture was diluted with ethyl acetate (200 mL) and washed with saturated aqueous solution of ammonium chloride (100 mL), saturated aqueous sodium bicarbonate solution (100 mL), water (100 mL) and brine (100 mL). The organic layer was dried over anhydrous sodium sulfate, concentrated and the residue thus obtained was purified by flash silica gel column chromatography to yield 655 mg of the titled product. The intermediate was as such carried forward to the next step without any characterization.

Step 3: (S)—N-(2-Chloro-4-methylphenyl)-4-(2-(4-(1,1-difluoro-2-hydroxypropyl)phenyl)acetamido)-N-methylbenzamide To a stirred solution of Step 2 Intermediate (270 mg, 0.39 mmol) in a mixture of THF (6.0 mL), methanol (4.0 mL) and water (2.0 mL) was added lithium hydroxide monohydrate (49 mg, 1.17 mmol) and the mixture was stirred at RT for 30 min. The reaction mixture was quenched with 1N HCl (10 mL) and the product was extracted in ethyl acetate (2×20 mL). The combined organic layers were washed with water (20 mL) and brine (10 mL). The organic layer was dried over anhydrous sodium sulfate and concentrated under reduced pressure. The residue obtained was purified by flash silica gel column chromatography to yield 122 mg of the titled product. $^1$H NMR (300 MHz, DMSO-$d_6$) δ 1.06 (d, J=6.3 Hz, 3H), 2.22 (s, 3H), 3.20 (s, 3H), 3.65 (s, 2H), 3.98-4.05 (m, 1H), 5.48 (d, J=6.0 Hz, 1H), 6.98-7.12 (m, 1H), 7.20 (d, J=8.1 Hz, 2H), 7.24-7.29 (m, 2H), 7.35-7.41 (m, 6H), 10.26 (s, 1H); APCI-MS (m/z) 485 (M−H)$^-$; Chiral HPLC purity: 92.55%.

All the examples were prepared by following the methods described above from the combination of appropriate intermediates. Name, structure, Intermediate/method used and characterization data for Example 4, 6□8, 10120, 10□20, 22□28 and 31□40 are given in Table 1.

TABLE 1

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 4 | N-(2,5-Dichlorophenyl)-4-(2-(4-(1,1-difluoropropyl)phenyl)acetamido)-N-methylbenzamide | Intermediate 3 and Intermediate 5 Method C-Step 1 | $^1$H NMR (300 MHz, DMSO-$d_6$) δ 0.88 (t, J = 7.2 Hz, 3H), 2.11-2.25 (m, 2H), 3.23 (s, 3H), 3.67 (s, 2H), 7.20-7.24 (m, 2H), 7.34-7.44 (m, 8H), 7.72 (s, 1H), 10.30 (br s, 1H); APCI-MS (m/z) 490 (M − H)$^-$. |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 6 | 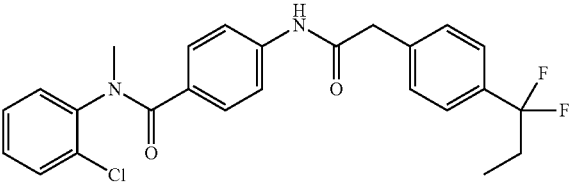<br>N-(2-Chlorophenyl)-4-(2-(4-(1,1-difluoropropyl)phenyl)acetamido)-N-methylbenzamide | Intermediate 3 and Intermediate 6 Method C Step 1 | $^1$H NMR (300 MHz, DMSO-d$_6$) δ 0.87 (t, J = 7.2 Hz, 3H), 2.08-2.25 (m, 2H), 3.21 (s, 3H), 3.64 (s, 2H), 7.16-7.28 (m, 4H), 7.36-7.43 (m, 8H), 10.23 (s, 1H); ESI-MS (m/z) 457 (M + H)$^+$. |
| Example 7 | 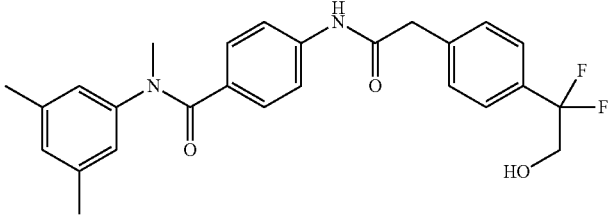<br>4-(2-(4-(1,1-Difluoro-2-hydroxyethyl)phenyl)acetamido)-N-(3,5-dimethylphenyl)-N-methylbenzamide | Intermediate 2 and Intermediate 8 Method A | $^1$H NMR (300 MHz, DMSO-d$_6$) δ 2.14 (s, 6H), 3.29 (s, 3H), 3.67 (s, 2H), 3.75-3.87 (m, 2H), 5.62 (br s, 1H), 6.75 (s, 2H), 6.78 (s, 1H), 7.21 (d, J = 8.1 Hz, 2H), 7.37-7.48 (m, 5H), 10.27 (s, 1H); APCI-MS (m/z) 453 (M + H)$^+$. |
| Example 8 | 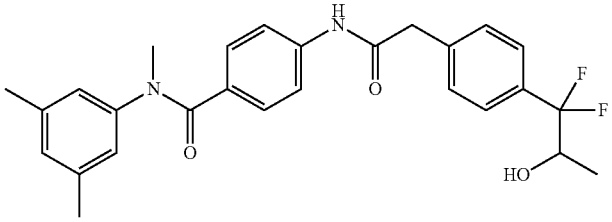<br>4-(2-(4-(1,1-Difluoro-2-hydroxypropyl)phenyl)acetamido)-N-(3,5-dimethylphenyl)-N-methylbenzamide | Intermediate 4 and Intermediate 8 Method C | $^1$H NMR (300 MHz, DMSO-d$_6$) δ 1.06 (d, J = 6.0 Hz, 3H), 2.14 (s, 6H), 3.29 (s, 3H), 3.66 (s, 2H), 4.00-4.06 (m, 1H), 6.75 (s, 2H), 6.78 (s, 1H), 7.20 (d, J = 8.7 Hz, 2H), 7.38-7.46 (m, 6H), 10.26 (s, 1H); ESI-MS (m/z) 467 (M + H)$^+$. |
| Example 10 | 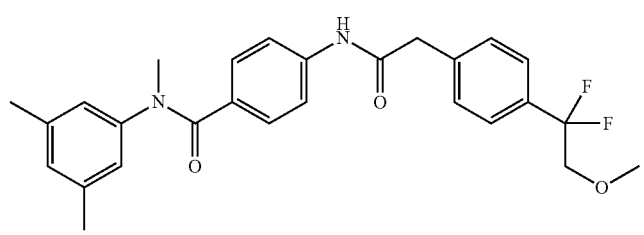<br>4-(2-(4-(1,1-Difluoro-2-methoxyethyl)phenyl)acetamido)-N-(3,5-dimethylphenyl)-N-methylbenzamide | Intermediate 7 and Intermediate 8 Method A Step 1 | $^1$H NMR (300 MHz, DMSO-d$_6$) δ 2.14 (s, 6H), 3.27-3.35 (m, 6H), 3.68 (s, 2H), 3.82-3.91 (m, 2H), 6.76 (d, J = 10.5 Hz, 3H), 6.75 (s, 2H), 6.78 (s, 1H), 7.41-7.50 (m, 6H), 10.30 (s, 1H); APCI-MS (m/z) 468 (M + H)$^+$. |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 11 | 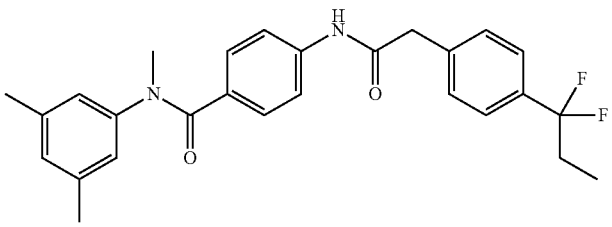<br>4-(2-(4-(1,1-Difluoropropyl)phenyl)acetamido)-N-(3,5-dimethylphenyl)-N-methylbenzamide | Intermediate 3 and Intermediate 8 Method A Step 1 | $^1$H NMR (300 MHz, DMSO-$d_6$) δ 0.88 (t, J = 7.2 Hz, 3H), 2.14 (s, 6H), 2.15-2.20 (m, 2H), 3.29 (s, 3H), 3.67 (s, 2H), 6.75 (s, 2H), 6.78 (s, 2H), 7.21 (d, J = 8.1 Hz, 2H), 7.37-7.47 (m, 6H), 10.26 (s, 1H); APCI-MS (m/z) 451 (M + H)$^+$. |
| Example 12 | 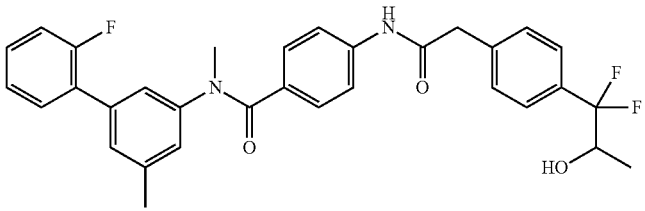<br>4-(2-(4-(1,1-Difluoro-2-hydroxypropyl)phenyl)acetamido)-N-(2'-fluoro-5-methyl-[1,1'-biphenyl]-3-yl)-N-methylbenzamide | Intermediate 4 and Intermediate 9 Method C | $^1$H NMR (300 MHz, CDCl$_3$) δ 1.22 (d, J = 6.3 Hz, 3H), 2.29 (s, 3H), 3.48 (s, 3H), 3.69 (s, 2H), 4.13-4.17 (m, 1H), 6.85 (s, 1H), 7.01 (s, 1H), 7.11-7.16 (m, 3H), 7.21-7.38 (m, 7H), 7.45-7.51 (m, 3H); APCI-MS (m/z) 548 (M + H)$^+$. |
| Example 13 | 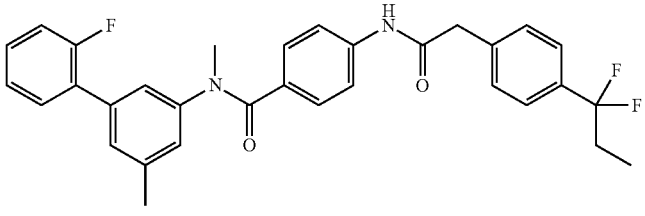<br>4-(2-(4-(1,1-Difluoropropyl)phenyl)acetamido)-N-(2'-fluoro-5-methyl-[1,1'-biphenyl]-3-yl)-N-methylbenzamide | Intermediate 3 and Intermediate 9 Method C Step 1 | $^1$H NMR (300 MHz, DMSO-$d_6$) δ 0.88 (t, J = 6.3 Hz, 3H), 2.18-2.23 (m, 2H), 2.26 (s, 3H), 3.36 (s, 3H), 3.67 (s, 2H), 7.05 (s, 2H), 7.15-7.28 (m, 6H), 7.39-7.47 (m, 7H), 10.27 (s, 1H); APCI-MS (m/z) 531 (M + H)$^+$. |
| Example 14 | 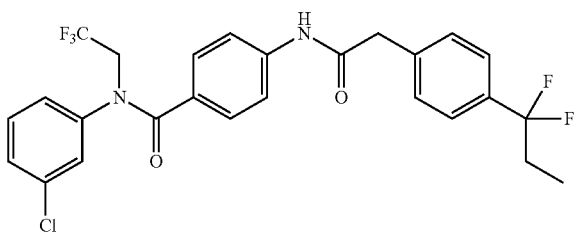<br>N-(3-Chlorophenyl)-4-(2-(4-(1,1-difluoropropyl)phenyl)acetamido)-N-(2,2,2-trifluoroethyl)benzamide | Intermediate 3 and Intermediate 10 Method C Step 1 | $^1$H NMR (300 MHz, DMSO-$d_6$) δ 0.87 (t, J = 7.8 Hz, 3H), 2.14-2.19 (m, 2H), 3.66 (s, 2H), 4.72 (q, J = 8.7 Hz, 2H), 7.05 (br s, 1H), 7.19-7.27 (m, 4H), 7.35-7.47 (m, 7H), 10.31 (s, 1H). |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 15 | 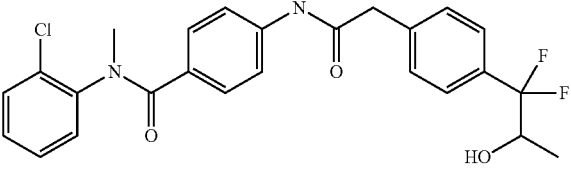<br>N-(2-Chlorophenyl)-4-(2-(4-(1,1-difluoro-2-hydroxypropyl)phenyl)acetamido)-N-methylbenzamide | Intermediate 4 and Intermediate 6 Method C | $^1$H NMR (300 MHz, DMSO-$d_6$) δ 1.05 (d, J = 6.3 Hz, 3H), 3.23 (s, 3H), 3.65 (s, 2H), 3.92-4.04 (m, 1H), 5.48 (d, J = 6.0 Hz, 1H), 7.19-7.28 (m, 4H), 7.36-7.42 (m, 8H), 10.26 (s, 1H); APCI-MS (m/z) 473 (M + H)$^+$. |
| Example 16 | 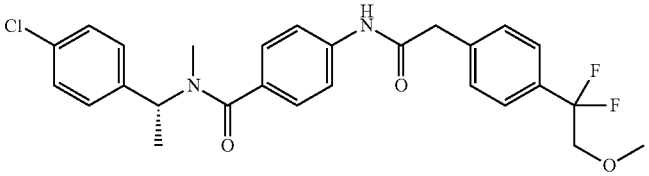<br>(R)-N-(1-(4-Chlorophenyl)ethyl)-4-(2-(4-(1,1-difluoro-2-methoxyethyl)phenyl)acetamido)-N-methylbenzamide | Intermediate 7 and Intermediate 11 Method A Step 1 | $^1$H NMR (300 MHz, DMSO-$d_6$) δ 1.53 (d, J = 6.9 Hz, 3H), 2.61 (s, 3H), 3.31 (s, 3H), 3.72 (s, 2H), 3.83-3.92 (m, 2H), 7.31-7.54 (m, 10H), 7.66 (d, J = 8.1 Hz, 2H), 10.39 (s, 1H); APCI-MS (m/z) 502 (M + H)$^+$. |
| Example 17 | 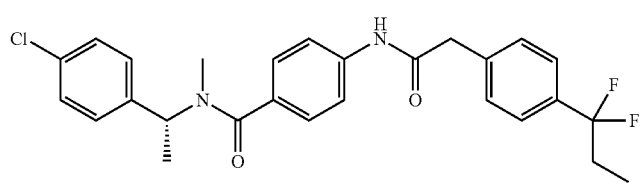<br>(R)-N-(1-(4-Chlorophenyl)ethyl)-4-(2-(4-(1,1-difluoropropyl)phenyl)acetamido)-N-methylbenzamide | Intermediate 3 and Intermediate 11 Method A Step 1 | $^1$H NMR (300 MHz, DMSO-$d_6$) δ 0.89 (t, J = 7.5 Hz, 3H), 1.52 (d, J = 6.6 Hz, 3H), 2.10-2.21 (m, 2H), 2.60 (s, 3H), 3.71 (s, 2H), 7.31-7.48 (m, 10H), 7.65 (d, J = 8.7 Hz, 2H), 10.39 (s, 1H); APCI-MS (m/z) 485 (M + H)$^+$. |
| Example 18 | 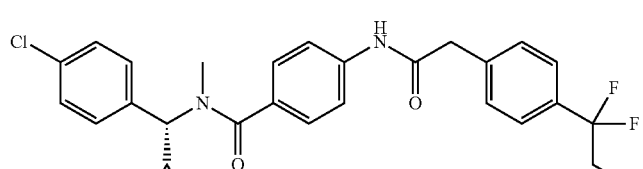<br>(R)-N-((4-chlorophenyl)(cyclopropyl)methyl)-4-(2-(4-(1,1-difluoropropyl)phenyl)acetamido)-N-methylbenzamide | Intermediate 3 and Intermediate 13 Method C Step 1 | $^1$H NMR (300 MHz, DMSO-$d_6$) δ 0.74-0.77 (m, 2H), 0.79-0.83 (m, 2H), 0.89 (t, J = 7.2 Hz, 3H), 1.13 (s, 1H), 1.15-1.25 (m, 1H), 2.11-2.23 (m, 2H), 2.78 (s, 3H), 3.71 (s, 2H), 7.34-7.40 (m, 2H), 7.41-7.50 (m, 8H), 7.65 (d, J = 7.5 Hz, 2H), 10.38 (s, 1H). |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 19 | 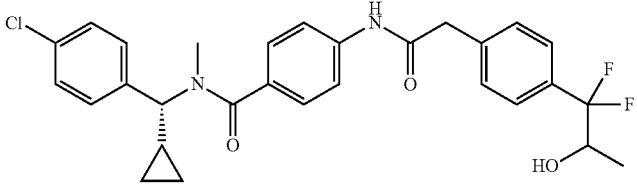<br>N-((R)-(4-chlorophenyl)(cyclopropyl)methyl)-4-(2-(4-(1,1-difluoro-2-hydroxypropyl)phenyl)acetamido)-N-methylbenzamide | Intermediate 4 and Intermediate 13 Method C | $^1$H NMR (300 MHz, DMSO-$d_6$) δ 0.40-0.51 (m, 2H), 0.55-0.65 (m, 1H), 0.72-0.81 (m, 1H), 1.03 (d, J = 6.0 Hz, 3H), 1.40-1.45 (m, 1H), 1.87 (br s, 0.5H, rotamer), 2.15 (br s, 0.5H, rotamer), 2.76 (s, 3H), 3.69 (s, 2H), 4.01 (br s, 1H), 5.49 (d, J = 6.0 Hz, 1H), 7.10-7.45 (m, 10H), 7.63 (d, J = 6.3 Hz, 2H), 10.37 (s, 1H); APCI-MS (m/z) 527 (M + H)$^+$. |
| Example 20 | 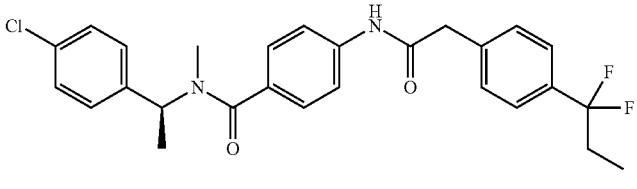<br>(S)-N-(1-(4-Chlorophenyl)ethyl)-4-(2-(4-(1,1-difluoropropyl)phenyl)acetamido)-N-methylbenzamide | Intermediate 3 and Intermediate 12 Method A Step 1 | $^1$H NMR (300 MHz, DMSO-$d_6$) δ 0.89 (t, J = 7.2 Hz, 3H), 1.52 (d, J = 6.3 Hz, 3H), 2.10-2.21 (m, 2H), 2.61 (s, 3H), 3.72 (s, 2H), 7.30-7.45 (m, 10H), 7.66 (d, J = 8.1 Hz, 2H), 10.39 (s, 1H); APCI-MS (m/z) 485 (M + H)$^+$. |
| Example 22 | 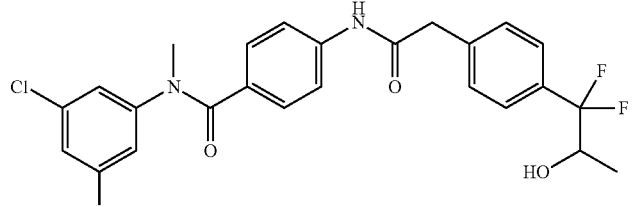<br>N-(3-Chloro-5-fluorophenyl)-4-(2-(4-(1,1-difluoro-2-hydroxypropyl)phenyl)acetamido)-N-methylbenzamide | Intermediate 2 and Intermediate 15 Method E | $^1$H NMR (300 MHz, DMSO-$d_6$) δ 2.35 (s, 3H), 3.33 (s, 3H), 3.72 (s, 2H), 7.10-7.28 (m, 5H), 7.50 (d, J = 7.8 Hz, 6H), 10.35 (s, 1H); APCI-MS (m/z) 489 (M + H)$^+$. |
| Example 23 | 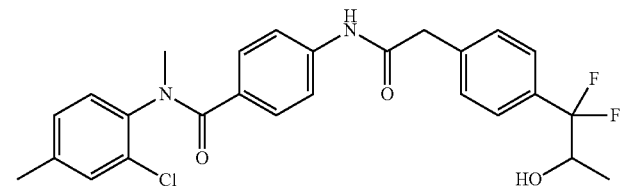 [SMILES: Cc1ccc(N(C)C(=O)c2ccc(NC(=O)Cc3ccc(C(F)(F)[C@H](C)O)cc3)cc2)c(Cl)c1]<br>N-(2-Chloro-4-methylphenyl)-4-(2-(4-(1,1-difluoro-2-hydroxypropyl)phenyl)acetamido)-N-methylbenzamide | Intermediate 2 and Intermediate 16 Method E | $^1$H NMR (300 MHz, DMSO-$d_6$) δ 1.05 (d, J = 5.7 Hz, 3H), 2.22 (s, 3H), 3.20 (s, 3H), 3.65 (s, 2H), 3.98-4.05 (m, 1H), 5.50 (d, J = 5.7 Hz, 1H), 7.08-7.11 (m, 1H), 7.20-7.30 (m, 4H), 7.32-7.40 (m, 6H), 10.27 (s, 1H); APCI-MS (m/z) 487 (M + H)$^+$. |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 24 | 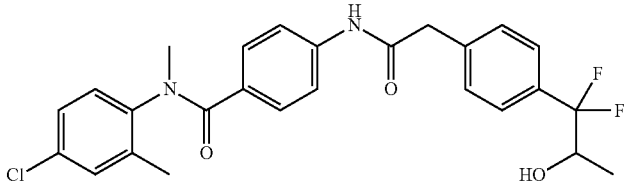<br>N-(4-Chloro-2-methylphenyl)-4-(2-(4-(1,1-difluoro-2-hydroxypropyl)phenyl)acetamido)-N-methylbenzamide | Intermediate 2 and Intermediate 17 Method E | $^1$H NMR (300 MHz, DMSO-$d_6$) δ 1.05 (d, J = 6.0 Hz, 3H), 2.08 (s, 3H), 3.18 (s, 3H), 3.63 (s, 2H), 3.97-4.01 (m, 1H), 5.46 (d, J = 6.0 Hz, 1H), 7.10-7.26 (m, 5H), 7.35-7.42 (m, 6H), 10.24 (s, 1H); APCI-MS (m/z) 487 (M + H)$^+$. |
| Example 25 | 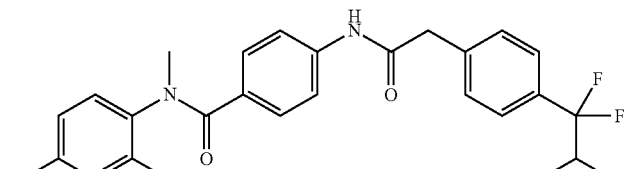<br>N-(2,4-Dichlorophenyl)-4-(2-(4-(1,1-difluoro-2-hydroxypropyl)phenyl)acetamido)-N-methylbenzamide | Intermediate 2 and Intermediate 18 Method E | $^1$H NMR (300 MHz, DMSO-$d_6$) δ 1.06 (d, J = 6.0 Hz, 3H), 3.21 (s, 3H), 3.66 (s, 2H), 3.99-4.06 (m, 1H), 5.50 (d, J = 6.0 Hz, 1H), 7.19-7.24 (m, 2H), 7.37-7.45 (m, 8H), 7.63 (s, 1H), 10.29 (s, 1H); ESI-MS (m/z) 507 (M + H)$^+$. |
| Example 26 | 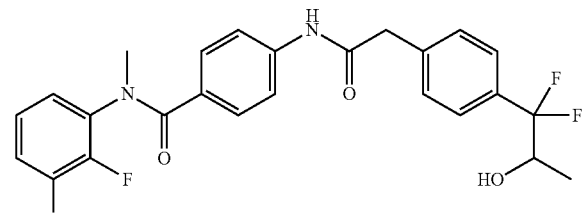<br>N-(3-Chloro-2-fluorophenyl)-4-(2-(4-(1,1-difluoro-2-hydroxypropyl)phenyl)acetamido)-N-methylbenzamide | Intermediate 2 and Intermediate 19 Method E | $^1$H NMR (300 MHz, DMSO-$d_6$) δ 1.06 (d, J = 6.0 Hz, 3H), 3.29 (s, 3H), 3.67 (s, 2H), 3.99-4.06 (m, 1H), 5.50 (d, J = 6.0 Hz, 1H), 7.17-7.26 (m, 3H), 7.37-7.48 (m, 8H), 10.31 (s, 1H); ESI-MS (m/z) 491 (M + H)$^+$. |
| Example 27 | 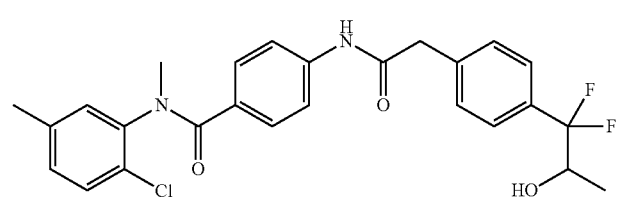<br>N-(2-Chloro-5-methylphenyl)-4-(2-(4-(1,1-difluoro-2-hydroxypropyl)phenyl)acetamido)-N-methylbenzamide | Intermediate 2 and Intermediate 20 Method E | $^1$H NMR (300 MHz, DMSO-$d_6$) δ 1.05 (d, J = 5.7 Hz, 3H), 2.21 (s, 3H), 3.21 (s, 3H), 3.65 (s, 2H), 3.98-4.03 (m, 1H), 5.49 (d, J = 6.0 Hz, 1H), 7.04-7.10 (m, 1H), 7.21-7.28 (m, 4H), 7.30-7.44 (m, 6H), 10.27 (s, 1H); APCI-MS (m/z) 487 (M + H)$^+$. |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 28 | 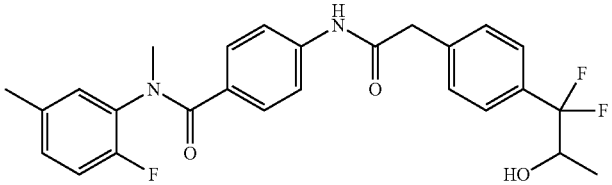 [SMILES: Cc1ccc(F)c(N(C)C(=O)c2ccc(NC(=O)Cc3ccc(C(F)(F)C(C)O)cc3)cc2)c1]<br>4-(2-(4-(1,1-Difluoro-2-hydroxypropyl)phenyl)acetamido)-N-(2-fluoro-5-methylphenyl)-N-methylbenzamide | Intermediate 2 and Intermediate 21 Method E | $^1$H NMR (300 MHz, DMSO-$d_6$) δ 1.06 (d, J = 6.3 Hz, 3H), 2.21 (s, 3H), 3.26 (s, 3H), 3.66 (s, 2H), 3.99-4.05 (m, 1H), 5.49 (d, J = 6.0 Hz, 1H), 6.96-7.05 (m, 2H), 7.22 (t, J = 8.1 Hz, 3H), 7.35-7.47 (m, 6H), 10.29 (s, 1H); APCI-MS (m/z) 472 (M + H)$^+$. |
| Example 31 | 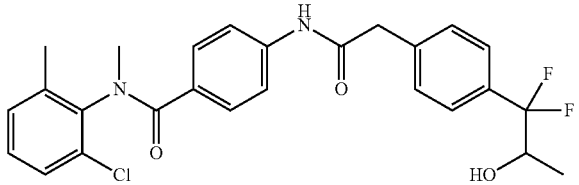<br>N-(2-Chloro-6-methylphenyl)-4-(2-(4-(1,1-difluoro-2-hydroxypropyl)phenyl)acetamido)-N-methylbenzamide | Intermediate 4 and Intermediate 22 Method C | $^1$H NMR (300 MHz, DMSO-$d_6$) δ 1.05 (d, J = 6.3 Hz, 3H), 2.20 (s, 3H), 3.16 (s, 3H), 3.64 (s, 2H), 3.98-4.04 (m, 1H), 7.16-7.22 (m, 4H), 7.28-7.32 (m, 2H), 7.35-7.41 (m, 6H), 10.27 (s, 1H); APCI-MS (m/z) 487 (M + H)$^+$. |
| Example 32 | 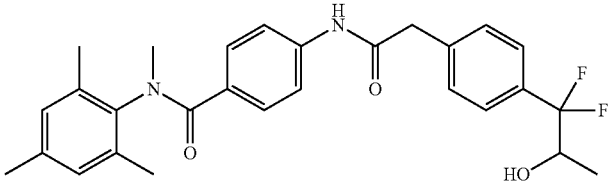<br>4-(2-(4-(1,1-Difluoro-2-hydroxypropyl)phenyl)acetamido)-N-mesityl-N-methylbenzamide | Intermediate 4 and Intermediate 23 Method C | $^1$H NMR (300 MHz, DMSO-$d_6$) δ 1.05 (d, J = 6.3 Hz, 3H), 2.08 (s, 6H), 2.15 (s, 3H), 3.11 (s, 3H), 3.64 (s, 2H), 4.01-4.06 (m, 1H), 5.48 (d, J = 6.0 Hz, 1H), 6.82 (s, 2H), 7.13 (t, J = 8.4 Hz, 2H), 7.35-7.45 (m, 6H), 10.26 (s, 1H); APCI-MS (m/z) 481 (M + H)$^+$. |
| Example 33 | 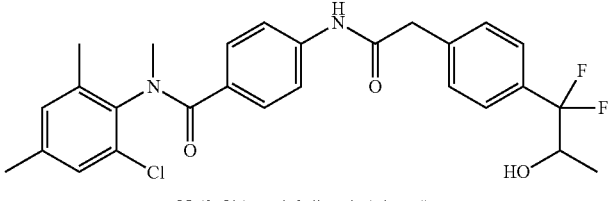<br>N-(2-Chloro-4,6-dimethylphenyl)-4-(2-(4-(1,1-difluoro-2-hydroxypropyl)phenyl)acetamido)-N-methylbenzamide | Intermediate 4 and Intermediate 24 Method C | $^1$H NMR (300 MHz, DMSO-$d_6$) δ 1.06 (d, J = 6.3 Hz, 3H), 2.15 (s, 3H), 2.19 (s, 3H), 3.13 (s, 3H), 3.65 (s, 2H), 3.98-4.04 (m, 1H), 5.49 (d, J = 6.0 Hz, 1H), 6.96-7.02 (m, 2H), 7.13 (s, 1H), 7.20 (d, J = 8.7 Hz, 2H), 7.35-7.45 (m, 5H), 10.27 (s, 1H); APCI-MS (m/z) 501 (M + H)$^+$. |
| Example 34 | 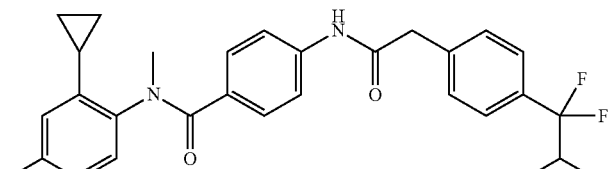<br>N-(2-Cyclopropyl-4-methylphenyl)-4-(2-(4-(1,1-difluoro-2-hydroxypropyl)phenyl)acetamido)-N-methylbenzamide | Intermediate 4 and Intermediate 25 Method C | $^1$H NMR (300 MHz, DMSO-$d_6$) δ 0.50-0.63 (m, 2H), 0.90-0.96 (m, 2H), 1.05 (d, J = 6.3 Hz, 3H), 1.78-1.82 (m, 1H), 2.16 (s, 3H), 3.25 (s, 3H), 3.64 (s, 2H), 3.99-4.06 (m, 1H), 5.48 (d, J = 6.0 Hz, 1H), 6.57 (s, 1H), 6.85 (d, J = 7.2 Hz, 1H), 6.96 (d, J = 7.2 Hz, 1H), 7.21 (d, J = 7.8 Hz, 2H), 7.35-7.41 (m, 6H), 10.23 (s, 1H). |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 35 | (S)-4-(2-(4-(1,1-difluoro-2-hydroxypropyl)phenyl)acetamido)-N-(3,5-dimethylphenyl)-N-methylbenzamide | Intermediate 4 and Intermediate 8 Method G | $^1$H NMR (300 MHz, DMSO-$d_6$) δ 1.05 (d, J = 6.3 Hz, 3H), 2.14 (s, 6H), 3.29 (s, 3H), 3.66 (s, 2H), 3.99-4.05 (m, 1H), 5.49 (br s, 1H), 6.75 (s, 2H), 6.78 (s, 1H), 7.20 (d, J = 8.7 Hz, 2H), 7.38-7.45 (m, 6H), 10.27 (s, 1H); APCI-MS (m/z) 467 (M + H)$^+$; chiral HPLC purity: 90.92%. |
| Example 36 | (R)-4-(2-(4-(1,1-Difluoro-2-hydroxypropyl)phenyl)acetamido)-N-(3,5-dimethylphenyl)-N-methylbenzamide | Intermediate 4 and Intermediate 8 Method F | $^1$H NMR (300 MHz, DMSO-$d_6$) δ 1.06 (d, J = 6.3 Hz, 3H), 2.14 (s, 6H), 3.29 (s, 3H), 3.66 (s, 2H), 3.99-4.05 (m, 1H), 5.49 (d, J = 6.0 Hz, 1H), 6.74-6.80 (m, 3H), 7.21 (d, J = 8.1 Hz, 2H), 7.38-7.45 (m, 6H), 10.27 (s, 1H); APCI-MS (m/z) 467 (M + H)$^+$, chiral HPLC purity: 92.88%. |
| Example 37 | N-(4-Chloro-2-fluoro-5-methylphenyl)-4-(2-(4-(1,1-difluoro-2-hydroxypropyl)phenyl)acetamido)-N-methylbenzamide | Intermediate 4 and Intermediate 26 Method C | $^1$H NMR (300 MHz, DMSO-$d_6$) δ 1.06 (d, J = 6.3 Hz, 3H), 2.23 (s, 3H), 3.26 (s, 3H), 3.67 (s, 2H), 4.03 (br s, 1H), 5.47 (d, J = 6.0 Hz, 1H), 7.24 (d, J = 7.2 Hz, 2H), 7.39-7.49 (m, 8H), 10.30 (s, 1H). |
| Example 38 | N-(2-Chloro-4-cyclopropyl phenyl)-4-(2-(4-(1,1-difluoro-2-hydroxypropyl)phenylacetamido)-N-methylbenzamide | Intermediate 4 and Intermediate 27 Method C | $^1$H NMR (300 MHz, DMSO-$d_6$) δ 0.61-0.65 (m, 2H), 0.82-0.92 (m, 2H), 1.04 (d, J = 6.0 Hz, 3H), 1.82-1.86 (m, 1H), 3.17 (s, 3H), 3.63 (s, 2H), 3.99-4.03 (m, 1H), 5.47 (d, J = 6.0 Hz, 1H), 6.94-6.98 (m, 2H), 7.10-7.25 (m, 4H), 7.35-7.39 (m, 5H), 10.24 (s, 1H). |

TABLE 1-continued

Chemical name, structure, Intermediate No., method of preparation and analytical data of Example 4, 6-8, 10-20, 22-28 and 31-40

| Example No. | Chemical Name and Structure | Intermediate/ Method | Analytical Data |
|---|---|---|---|
| Example 39 | 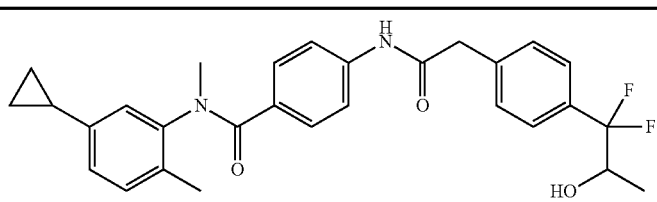<br>N-(5-Cyclopropyl-2-methylphenyl)-4-(2-(4-(1,1-difluoro-2-hydroxypropyl)phenyl)acetamido)-N-methylbenzamide | Intermediate 4 and Intermediate 28 Method C | $^1$H NMR (300 MHz, DMSO-$d_6$) δ 0.39-0.43 (m, 1H), 0.62-0.66 (m, 1H), 0.85-0.89 (m, 2H), 1.05 (d, J = 5.4 Hz, 3H), 1.77-1.83 (m, 1H), 2.03 (s, 3H), 3.20 (s, 3H), 3.64 (s, 2H), 4.02-4.05 (m, 1H), 5.48 (d, J = 6.0 Hz, 1H), 6.84-6.88 (m, 2H), 6.96-7.02 (m, 2H), 7.15-7.19 (m, 2H), 7.35-7.41 (m, 5H), 10.23 (s, 1H); APCI-MS (m/z) 493 (M + H)$^+$. |
| Example 40 | 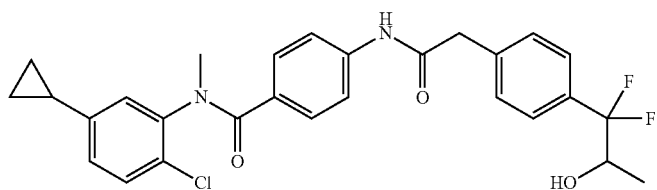<br>N-(2-Chloro-5-cyclopropyl phenyl)-4-(2-(4-(1,1-difluoro-2-hydroxypropyl)phenyl)acetamido)-N-methylbenzamide | Intermediate 2 and Intermediate 29 Method E | $^1$H NMR (300 MHz, DMSO-$d_6$) δ 0.45-0.49 (m, 1H), 0.65-0.69 (m, 1H), 0.88-0.94 (m, 2H), 1.05 (d, J = 5.7 Hz, 3H), 1.82-1.86 (m, 1H), 3.21 (s, 3H), 3.66 (s, 2H), 4.01-4.05 (m, 1H), 5.48 (d, J = 6.0 Hz, 1H), 6.95-6.99 (m, 2H), 7.10-7.22 (m, 4H), 7.38-7.43 (m, 5H), 10.25 (s, 1H). |

PHARMACOLOGICAL ACTIVITY

Biological Assay

The compounds described herein were screened for ROR gamma modulator activity using the TR-FRET assay (LanthaScreen™ available from Invitrogen of Carlsbad, Calif.) as described in *JBC* 2011, 286, 26: 22707-10; and *Drug Metabolism and Disposition* 2009, 37, 10: 2069-78.

TR-FRET Assay for ROR Gamma

The assay is based on the principle that binding of the agonist to the ROR gamma causes a conformational change around helix 12 in the ligand binding domain, resulting in higher affinity for the co-activator peptide. ROR gamma being constitutively active, the Fluorescein-D22 co-activator peptide used in the assay is recruited in the absence of a ligand. Binding of the co-activator peptide, causes an increase in the TR-FRET signal while binding of an antagonist decreases the recruitment of the co-activator peptide, causing a decrease in the TR-FRET signal compared to control with no compound. The assay was performed using a two-step procedure, pre-incubation step with the compound followed by the detection step on addition of the anti-GST tagged terbium (Tb) and fluorescein tagged fluorophores as the acceptor.

Test compounds or reference compounds such as T0901317 (Calbiochem) were dissolved in dimethylsulfoxide (DMSO) to prepare 10.0 mM stock solutions and diluted to the desired concentration. The final concentration of DMSO in the reaction was 4% (v/v). The assay mixture was prepared by mixing 10 nM of the GST-tagged ROR gamma ligand binding domain (LBD) in the assay buffer containing 25 mM HEPES, 100 mM NaCl, 5 mM DTT and 0.01% BSA with or without the desired concentration of the compound.

The reaction was incubated at 22° C. for 1 hour. The pre-incubation step was terminated by addition of the detection mixture containing 300 nM Fluorescein-D22 co-activator peptide and 10 nM lantha screen Tb-anti GST antibody into the reaction mixture. After shaking for 5 minutes the reaction was further incubated for 1 hour at room temperature and read at 4° C. on an Infinite F500 reader as per the kit instructions (Invitrogen). The inhibition of test compound was calculated based on the TR-FRET ratio of 520/495. The activity was calculated as a percent of control reaction. IC$_{50}$ values were calculated from dose response curve by nonlinear regression analysis using GraphPad Prism software.

The compounds prepared were tested using the above assay procedure and the results obtained are given in Table 2. Percentage inhibition at concentrations of 1.0 μM and 10.0 μM are given in the table along with IC$_{50}$ (nM) details for selected examples. The compounds were found to have IC$_{50}$ less than 500 nM, preferably less than 100 nM, more preferably less than 50 nM.

The IC$_{50}$ (nM) values are set forth in Table 2 wherein "A" refers to an IC$_{50}$ value of less than 50 nM, "B" refers to IC$_{50}$ value in range of 50.01 to 100.0 nM and "C" refers to IC$_{50}$ values more than 100 nM.

TABLE 2

In-vitro screening results

| S. N. | Examples No. | % Inhibition at 1 μM | % Inhibition at 10 μM | IC$_{50}$ value (nM) |
|---|---|---|---|---|
| 1. | Example 1 | 27.65 | 64.47 | |
| 2. | Example 2 | 20.74 | 43.42 | |
| 3. | Example 3 | 74.99 | 85.85 | C |
| 4. | Example 4 | 88.49 | 91.12 | A |

TABLE 2-continued

In-vitro screening results

| S. N. | Examples No. | % Inhibition at 1 µM | % Inhibition at 10 µM | IC$_{50}$ value (nM) |
|---|---|---|---|---|
| 5. | Example 5 | 87.58 | 94.33 | A |
| 6. | Example 6 | 90.9 | 91.15 | A |
| 7. | Example 7 | 87.52 | 95.06 | A |
| 8. | Example 8 | 94.79 | 96.51 | A |
| 9. | Example 9 | 86.23 | 96.99 | C |
| 10. | Example 10 | 93.22 | 95.27 | A |
| 11. | Example 11 | 90.06 | 92.92 | A |
| 12. | Example 12 | 89.4 | 93.68 | B |
| 13. | Example 13 | 87.46 | 90.57 | B |
| 14. | Example 14 | 84.04 | 87.64 | A |
| 15. | Example 15 | 85.49 | 92.85 | A |
| 16. | Example 16 | 84.46 | 93.69 | C |
| 17. | Example 17 | 87.13 | 90.77 | A |
| 18. | Example 18 | 87.37 | 89.98 | A |
| 19. | Example 19 | 82.58 | 92.83 | B |
| 20. | Example 20 | 61.53 | 75.03 | — |
| 21. | Example 21 | 82.21 | 87.88 | A |
| 22. | Example 22 | 79.99 | 83.13 | A |
| 23. | Example 23 | 88.83 | 93.18 | A |
| 24. | Example 24 | 82.62 | 88.71 | A |
| 25. | Example 25 | 82.03 | 89.97 | A |
| 26. | Example 26 | 86.39 | 93.25 | A |
| 27. | Example 27 | 90.09 | 91.95 | A |
| 28. | Example 28 | 90.51 | 93.86 | A |
| 29. | Example 29 | 80.69 | 87.06 | A |
| 30. | Example 30 | 85.45 | 88.71 | A |
| 31. | Example 31 | 79.13 | 86.63 | B |
| 32. | Example 32 | 84.9 | 95.03 | B |
| 33. | Example 33 | 86.76 | 90.16 | A |
| 34. | Example 34 | 91.82 | 92.59 | A |
| 35. | Example 35 | 89.44 | 93.27 | A |
| 36. | Example 36 | 89.7 | 94.53 | A |
| 37. | Example 37 | 93.94 | 96.3 | A |
| 38. | Example 38 | 92.6 | 94.77 | A |
| 39. | Example 39 | 84.1 | 92.0 | A |
| 40. | Example 40 | 90.8 | 94.3 | A |

(—): Not determined

What is claimed is:

1. A compound of formula (I)

or a tautomer thereof, stereoisomer thereof or pharmaceutically acceptable salt thereof,
wherein
R$^1$ is selected from amino, hydroxyl, C$_{1-8}$alkyl and C$_{1-8}$alkoxy;
R$^2$ is selected from C$_{1-8}$alkyl, haloC$_{1-8}$alkyl, hydroxyC$_{1-8}$alkyl, C$_{3-6}$cycloalkyl and C$_{3-6}$cycloalkylC$_{1-8}$alkyl;
R$^3$ is selected from hydrogen, C$_{1-8}$alkyl, haloC$_{1-8}$alkyl and hydroxyC$_{1-8}$alkyl;
R$^4$ is selected from C$_{1-8}$alkyl, C$_{1-8}$alkoxy, haloC$_{1-8}$alkyl, hydroxyC$_{1-8}$alkyl, C$_{3-6}$cycloalkyl and C$_{3-6}$cycloalkylC$_{1-8}$alkyl;
each occurrence of R$^5$ is independently selected from halogen, hydroxyl, cyano, C$_{1-8}$alkyl, C$_{1-8}$alkoxy, haloC$_{1-8}$alkyl, haloC$_{1-8}$alkoxy, hydroxyC$_{1-8}$alkyl, C$_{3-6}$cycloalkyl and optionally substituted C$_{6-14}$aryl, wherein the substitution on C$_{6-14}$aryl is halogen;
each occurrence of R$^6$ is independently selected from halogen, cyano, hydroxyl, C$_{1-8}$alkyl and C$_{3-6}$cycloalkyl;
R$^a$ and R$^b$, which may be same or different, are each independently selected from hydrogen and C$_{1-8}$alkyl; or R$^a$ and R$^b$ together may form an oxo group;
'n' is 1, 2, 3 or 4;
'm' is 0, 1 or 2; and
'p' is 0 or 1.

2. The compound according to claim 1, wherein R$^1$ is amino, hydroxyl, methyl, methoxy or ethoxy.

3. The compound according to claim 1, wherein R$^2$ is methyl or 2,2,2-trifluoroethyl.

4. The compound according to claim 1, wherein each occurrence of R$^5$ is fluoro, chloro, methyl, cyclopropyl or 2-fluorophenyl.

5. The compound according to claim 1, wherein R$^a$ and R$^b$ are each independently selected from hydrogen and methyl.

6. The compound according to claim 1 seleted from
Ethyl 2-(4-(2-((4-((4-chlorophenyl)(methyl)carbamoyl)phenyl)amino)-2-oxoethyl)phenyl)-2,2-difluoroacetate,
N-(4-chlorophenyl)-4-(2-(4-(1,1-difluoro-2-hydroxyethyl)phenyl)acetamido)-N-methylbenzamide,
4-(2-(4-(2-amino-1,1-difluoro-2-oxoethyl)phenyl)acetamido)-N-(4-chlorophenyl)-N-methylbenzamide,
N-(2,5-Dichlorophenyl)-4-(2-(4-(1,1-difluoro-2-hydroxypropyl)phenyl)acetamido)-N-methylbenzamide,
4-(2-(4-(1,1-difluoro-2-hydroxy-2-methylpropyl)phenyl)acetamido)-N-(3,5-dimethylphenyl)-N-methylbenzamide,
N-(3,5-dichlorophenyl)-4-(2-(4-(1,1-difluoro-2-hydroxypropyl)phenyl)acetamido)-N-methylbenzamide,
(R)-N-(2-Chloro-4-methylphenyl)-4-(2-(4-(1,1-difluoro-2-hydroxypropyl)phenyl)acetamido)-N-methylbenzamide,
(S)-N-(2-Chloro-4-methylphenyl)-4-(2-(4-(1,1-difluoro-2-hydroxypropyl)phenyl)acetamido)-N-methylbenzamide,
N-(2,5-Dichlorophenyl)-4-(2-(4-(1,1-difluoropropyl)phenyl)acetamido)-N-methylbenzamide,
N-(2-Chlorophenyl)-4-(2-(4-(1,1-difluoropropyl)phenyl)acetamido)-N-methylbenzamide,
4-(2-(4-(1,1-Difluoro-2-hydroxyethyl)phenyl)acetamido)-N-(3,5-dimethylphenyl)-N-methylbenzamide,
4-(2-(4-(1,1-Difluoro-2-hydroxypropyl)phenyl)acetamido)-N-(3,5-dimethylphenyl)-N-methylbenzamide,
4-(2-(4-(1,1-Difluoro-2-methoxyethyl)phenyl)acetamido)-N-(3,5-dimethylphenyl)-N-methylbenzamide,
4-(2-(4-(1,1-Difluoropropyl)phenyl)acetamido)-N-(3,5-dimethylphenyl)-N-methylbenzamide,
4-(2-(4-(1,1-Difluoro-2-hydroxypropyl)phenyl)acetamido)-N-(2'-fluoro-5-methyl-[1,1'-biphenyl]-3-yl)-N-methylbenzamide,
4-(2-(4-(1,1-Difluoropropyl)phenyl)acetamido)-N-(2'-fluoro-5-methyl-[1,1'-biphenyl]-3-yl)-N-methylbenzamide,
N-(3-Chlorophenyl)-4-(2-(4-(1,1-difluoropropyl)phenyl)acetamido)-N-(2,2,2-trifluoroethyl)benzamide,
N-(2-Chlorophenyl)-4-(2-(4-(1,1-difluoro-2-hydroxypropyl)phenyl)acetamido)-N-methylbenzamide,
(R)-N-(1-(4-Chlorophenyl)ethyl)-4-(2-(4-(1,1-difluoro-2-methoxyethyl)phenyl)acetamido)-N-methylbenzamide, (R)-N-(1-(4-Chlorophenyl)ethyl)-4-(2-(4-(1,1-difluoropropyl)phenyl)acetamido)-N-methylbenzamide,
(R)-N-((4-chlorophenyl)(cyclopropyl)methyl)-4-(2-(4-(1,1-difluoropropyl)phenyl)acetamido)-N-methylbenzamide,
N-((R)-(4-chlorophenyl)(cyclopropyl)methyl)-4-(2-(4-(1,1-difluoro-2-hydroxypropyl)phenyl)acetamido)-N-methylbenzamide,
(S)-N-(1-(4-Chlorophenyl)ethyl)-4-(2-(4-(1,1-difluoropropyl)phenyl)acetamido)-N-methylbenzamide,
N-(3-Chloro-5-fluorophenyl)-4-(2-(4-(1,1-difluoro-2-hydroxypropyl)phenyl)acetamido)-N-methylbenzamide,
N-(2-Chloro-4-methylphenyl)-4-(2-(4-(1,1-difluoro-2-hydroxypropyl)phenyl)acetamido)-N-methylbenzamide,
N-(4-Chloro-2-methylphenyl)-4-(2-(4-(1,1-difluoro-2-hydroxypropyl)phenyl)acetamido)-N-methylbenzamide,
N-(2,4-Dichlorophenyl)-4-(2-(4-(1,1-difluoro-2-hydroxypropyl)phenyl)acetamido)-N-methylbenzamide,
N-(3-Chloro-2-fluorophenyl)-4-(2-(4-(1,1-difluoro-2-hydroxypropyl)phenyl)acetamido)-N-methylbenzamide,
N-(2-Chloro-5-methylphenyl)-4-(2-(4-(1,1-difluoro-2-hydroxypropyl)phenyl)acetamido)-N-methylbenzamide,
4-(2-(4-(1,1-Difluoro-2-hydroxypropyl)phenyl)acetamido)-N-(2-fluoro-5-methylphenyl)-N-methylbenzamide,
N-(2-Chloro-6-methylphenyl)-4-(2-(4-(1,1-difluoro-2-hydroxypropyl)phenyl)acetamido)-N-methylbenzamide,
4-(2-(4-(1,1-Difluoro-2-hydroxypropyl)phenyl)acetamido)-N-mesityl-N-methylbenzamide,
N-(2-Chloro-4,6-dimethylphenyl)-4-(2-(4-(1,1-difluoro-2-hydroxypropyl)phenyl)acetamido)-N-methylbenzamide,
N-(2-Cyclopropyl-4-methylphenyl)-4-(2-(4-(1,1-difluoro-2-hydroxypropyl)phenyl)acetamido)-N-methylbenzamide,
(S)-4-(2-(4-(1,1-difluoro-2-hydroxypropyl)phenyl)acetamido)-N-(3,5-dimethylphenyl)-N-methylbenzamide,
(R)-4-(2-(4-(1,1-Difluoro-2-hydroxypropyl)phenyl)acetamido)-N-(3,5-dimethylphenyl)-N-methylbenzamide,
N-(4-Chloro-2-fluoro-5-methylphenyl)-4-(2-(4-(1,1-difluoro-2-hydroxypropyl)henyl)acetamido)-N-methylbenzamide,
N-(2-Chloro-4-cyclopropylphenyl)-4-(2-(4-(1,1-difluoro-2-hydroxypropyl)phenyl)acetamido)-N-methylbenzamide,
N-(5-Cyclopropyl-2-methylphenyl)-4-(2-(4-(1,1-difluoro-2-hydroxypropyl)phenyl)acetamido)-N-methylbenzamide,
N-(2-Chloro-5-cyclopropylphenyl)-4-(2-(4-(1,1-difluoro-2-hydroxypropyl)phenyl)acetamido)-N-methylbenzamide,
and pharmaceutically acceptable salts thereof.

7. The compound according to claim 1 selected from
(R)-N-(2-Chloro-4-methylphenyl)-4-(2-(4-(1,1-difluoro-2-hydroxypropyl)phenyl)acetamido)-N-methylbenzamide,
(S)-N-(2-Chloro-4-methylphenyl)-4-(2-(4-(1,1-difluoro-2-hydroxypropyl)phenyl)acetamido)-N-methylbenzamide,
(R)-4-(2-(4-(1,1-Difluoro-2-hydroxypropyl)phenyl)acetamido)-N-(3,5-dimethylphenyl)-N-methylbenzamide,
(S)-4-(2-(4-(1,1-difluoro-2-hydroxypropyl)phenyl)acetamido)-N-(3,5-dimethylphenyl)-N-methylbenzamide,
and pharmaceutically acceptable salts thereof.

8. A compound of the formula

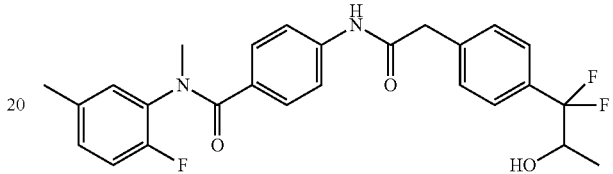

or a stereoisomer thereof, or a pharmaceutically acceptable salt thereof.

9. A pharmaceutical composition comprising a compound according to claim 1 and a pharmaceutically acceptable excipient.

10. The pharmaceutical composition according to claim 9, wherein the pharmaceutically acceptable excipient is a carrier or diluent.

11. A method of treating a RORγt mediated disease, disorder, syndrome, or condition in a subject having said disease, disorder, syndrome or condition comprising administering to the subject an effective amount of a compound according to claim 1.

12. The method according to claim 11, wherein the disease, disorder, syndrome or condition is an inflammatory or autoimmune disease.

13. The method according to claim 12, wherein the inflammatory or autoimmune disease is selected from rheumatoid arthritis, psoriasis, atopic dermatitis, chronic obstructive pulmonary disease (COPD), asthma, bronchospasm, cough, multiple sclerosis, colitis, ulcerative colitis and inflammatory bowel disease.

14. The method according to claim 13, wherein the disease, disorder, syndrome or condition is chronic obstructive pulmonary disease (COPD), asthma, bronchospasm or cough.

15. The method according to claim 13, wherein the disease, disorder, syndrome or condition is atopic dermatitis or psoriasis.

* * * * *